US010286084B2

(12) United States Patent
Cullen et al.

(10) Patent No.: US 10,286,084 B2
(45) Date of Patent: May 14, 2019

(54) COMPOSITIONS FOR THE INACTIVATION OF VIRUS REPLICATION AND METHODS OF MAKING AND USING THE SAME

(71) Applicants: DUKE UNIVERSITY, Durham, NC (US); EMORY UNIVERSITY, Atlanta, GA (US)

(72) Inventors: Bryan R. Cullen, Durham, NC (US); E. Matthew Kennedy, Durham, NC (US); Hal P. Bogerd, Durham, NC (US); Anand Kornepati, Durham, NC (US); Adam Mefferd, Durham, NC (US); Raymond F. Schinazi, Atlanta, GA (US)

(73) Assignees: Duke University, Durham, NC (US); Emory University, Atlanta, GA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/119,867

(22) PCT Filed: Feb. 18, 2015

(86) PCT No.: PCT/US2015/016354
§ 371 (c)(1),
(2) Date: Aug. 18, 2016

(87) PCT Pub. No.: WO2015/126927
PCT Pub. Date: Aug. 27, 2015

(65) Prior Publication Data
US 2017/0049909 A1 Feb. 23, 2017

Related U.S. Application Data

(60) Provisional application No. 61/940,883, filed on Feb. 18, 2014.

(51) Int. Cl.
*C07H 21/04* (2006.01)
*A61K 48/00* (2006.01)
*C12N 15/11* (2006.01)
*C12N 15/86* (2006.01)
*C12N 15/113* (2010.01)

(52) U.S. Cl.
CPC .......... *A61K 48/005* (2013.01); *C12N 15/111* (2013.01); *C12N 15/1131* (2013.01); *C12N 15/1132* (2013.01); *C12N 15/1133* (2013.01); *C12N 15/86* (2013.01); *C12N 2310/20* (2017.05); *C12N 2740/15043* (2013.01); *C12N 2750/14143* (2013.01)

(58) Field of Classification Search
None
See application file for complete search history.

(56) References Cited

U.S. PATENT DOCUMENTS

| 8,697,359 | B1 | 4/2014 | Zhang |
|---|---|---|---|
| 8,993,233 | B2 | 3/2015 | Zhang et al. |
| 9,637,739 | B2 | 5/2017 | Siksnys et al. |
| 2008/0193563 | A1 | 8/2008 | Stern et al. |
| 2008/0318210 | A1 | 12/2008 | Bentwich et al. |
| 2009/0029461 | A1 | 1/2009 | Choo et al. |
| 2009/0149409 | A1 | 6/2009 | Bohn et al. |
| 2011/0065100 | A1 | 3/2011 | Aldred et al. |
| 2012/0225477 | A1 | 9/2012 | Bentwich et al. |
| 2014/0068797 | A1 | 3/2014 | Doudna et al. |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0189896 | A1 | 7/2014 | Zhang et al. |
| 2014/0242664 | A1 | 8/2014 | Zhang et al. |
| 2014/0310830 | A1 | 10/2014 | Zhang et al. |

(Continued)

FOREIGN PATENT DOCUMENTS

| WO | WO-2009006584 A2 * | 1/2009 | ........... C12Q 1/6809 |
|---|---|---|---|
| WO | WO 2012/139122 A1 | 10/2012 | |

(Continued)

OTHER PUBLICATIONS

Jinek et al., A Programmable Dual-RNA-Guided DNA Endonuclease in Adaptive Bacterial Immunity. Science, 2012, 337:816-821.*
Makkerh et al., Comparative mutagenesis of nuclear localization signals reveals the importance of neutral and acidic amino acids. Current Bio, 1996, 6:1025-1027 (Year: 1996).*
Bogerd et al., A mammalian herpesvirus uses non-canonical expression and processing mechanisms to generate viral microRNAs. Mol Cell. Jan. 15, 2010; 37(1): 135. (Year: 2010).*
Aubert, M. et al., "In vitro Inactivation of Latent HSV by Targeted Mutagenesis Using an HSV-specific Homing Endonuclease," Molecular Therapy-Nucleic Acids 2014. 3:e146.

(Continued)

*Primary Examiner* — Christopher M Babic
*Assistant Examiner* — Arthur S Leonard
(74) *Attorney, Agent, or Firm* — Quarles & Brady LLP

(57) ABSTRACT

Provided herein are recombinant constructs, vectors and expression cassettes including a first promoter which is suitably a tRNA promoter operably connected to a first polynucleotide encoding a first single guide RNA and a second promoter operably connected to a second polynucleotide encoding a Cas9 polypeptide. The first single guide RNA includes a first portion complementary to a strand of a target sequence of a DNA virus and a second portion capable of interacting with the Cas9 polypeptide. Also provided are codon optimized *Staphylococcus aureus* derived Cas9 polynucleotides and polypeptides with nuclear localization signals and optionally an epitope tag. Also provided are constructs for production of sgRNAs including a tRNA. Methods of inhibiting viral replication, inhibiting expression of a target sequence from a virus or treating a viral infection or viral induced cancer using the compositions are also provided.

21 Claims, 25 Drawing Sheets
Specification includes a Sequence Listing.

(56) References Cited

U.S. PATENT DOCUMENTS

2014/0357530 A1 12/2014 Zhang et al.
2015/0284727 A1 10/2015 Kim et al.
2016/0017366 A1 1/2016 Chen et al.

FOREIGN PATENT DOCUMENTS

| WO | WO 2013/176772 A1 | 11/2013 | |
|---|---|---|---|
| WO | WO 2014/093622 A2 | 6/2014 | |
| WO | WO-2015089465 A1 * | 6/2015 | C12N 9/22 |

OTHER PUBLICATIONS

Bi, Y. et al., High-Efficiency Targeted Editing of Large Viral genomes by RNA-Guided Nucleases. PLOS Pathogens 2014. 10:1-11.

Caruntu, F.A. & Molagiv, V. "CccDNA persistence during natural evolutions of chronic VHB infection," Rom J Gastroenterol 2005, 14: 373-377.

Cong, L. et al., "Multiplex genome engineering using CRISPR/Cas systems," Science 2013, 339: 819-823.

Database geneseq Charpentier, et al. "Stphylococcus aureus CRISPR polypeptide SEQ:244" Database Accession No. BAZ4978. Jan. 16, 2014.

Ebina, H. et al., "Harnessing the CRISPR/Cas9 system to disrupt latent HIV-1 provirus," Scientific Reports 2013, 3:1-7.

European Search Report for European Patent Application No. EP15751819 dated Sep. 4, 2017 (12 pages).

Hou, Z. et al., "Efficient genome engineering in human pluripotent stem cells using Cas9 from Neisseria meningitidis," PNAS 2013, 110: 15644-15649.

Hsu, P.D., et al., "Development and Applications of CRISPR-Cas9 for Genome Engineering," Cell 2014, 157: 1263-1278.

Hu, W. et al., "RNA-mediated excision of the HIV-1 genome from latently infected cells in nervous system," Journal of Neurovirology 2013. S38.

Jinek, M. et al., "A programmable dual-RNA-guided DNA endonuclease in adaptive bacterial immunity," Science 2012, 337: 816-821.

Kennedy, E.M., et al., "Bacterial CRISPR/Cas DNA endonucleases: A revolutionary technology that could dramatically impact viral research and treatment," Virology 2015, 479-480: 213-220.

Kennedy, E.M., et al., "Inactivation of the human papillomavirus E6 or E7 gene in cervical carcinoma cells using a bacterial CRISPR/Cas RNA-guided endonuclease," Journal of Virology 2014, 88: 11965-11972.

Kennedy, E.M., et al., "Suppression of hepatitis B virus DNA accumulation in chronically infected cells using a bacterial CRISPR/Cas RNA-guided DNA endonuclease," Virology 2015, 476: 196-205.

Ma, W. et al., "A Significant Increase of RNAi Efficiency in Human Cells by the CMV Enhancer with a tRNAlys Promoter," Journal of Biomedicine and Biotechnology 2009, 2009:1-7.

Mali, P. et al., "RNA-guided human genome engineering via Cas9," Science 2013, 339: 823-826.

Mali, P. et al., "Cas9 as a versatile tool for engineering biology," Nature Methods 2013, 10:957-963.

Malmstrom, S. et al., "Hepatitis B viral DNA decline at loss of HBeAg is mainly explained by reduced cccDNA load—down-regulated transcription of PgRNA has limited impact," PLoS One 2012, 7: e36349.

Manjunath, N. et al., "Newer Gene Editing Technologies toward HIV Gene Therapy," Viruses 2013. 5:2748-2766.

Ran, F.A. "Double nicking by RNA-guided CRISPR Cas9 for enhanced genome editing specificity," Cell 2013, 154: 1380-1389.

Schiffer, J.T. et al., "Predictors of Hepatitis B Cure Using Gene Therapy to Deliver DNA Cleavage Enzymes: A Mathematical Modeling Approach," PLOS Computational Biology 2013. 9:1-16.

Shalem, O. et al., "Genome-scale CRISPR-Cas9 knockout screening in human cells," Science 2014, 343:84-87.

Zhang, Y., et al., "Processing-Independent CRISPR RNAs Limit Natural Transformation in Neisseria meningitidis," Mol Cell 2013, 50: 488-503.

* cited by examiner

Fig. 2
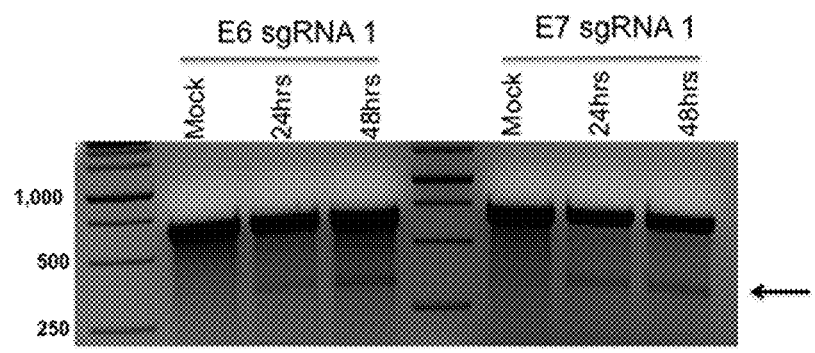
Fig. 3A
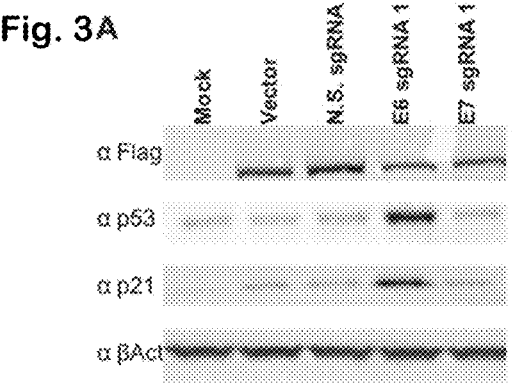
Fig. 3C
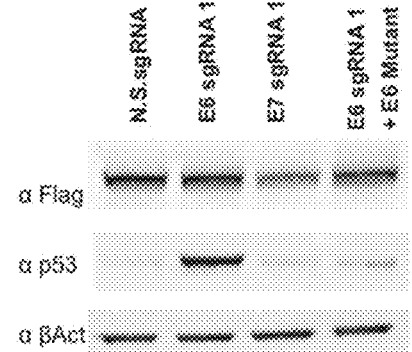
Fig. 3D
Fig. 3B
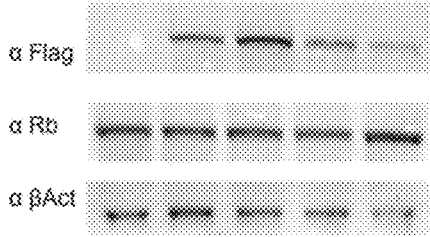

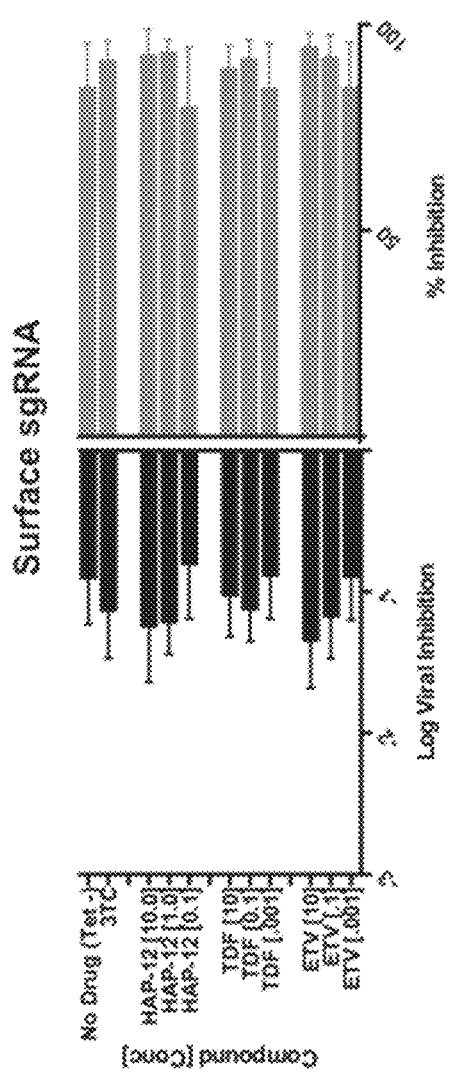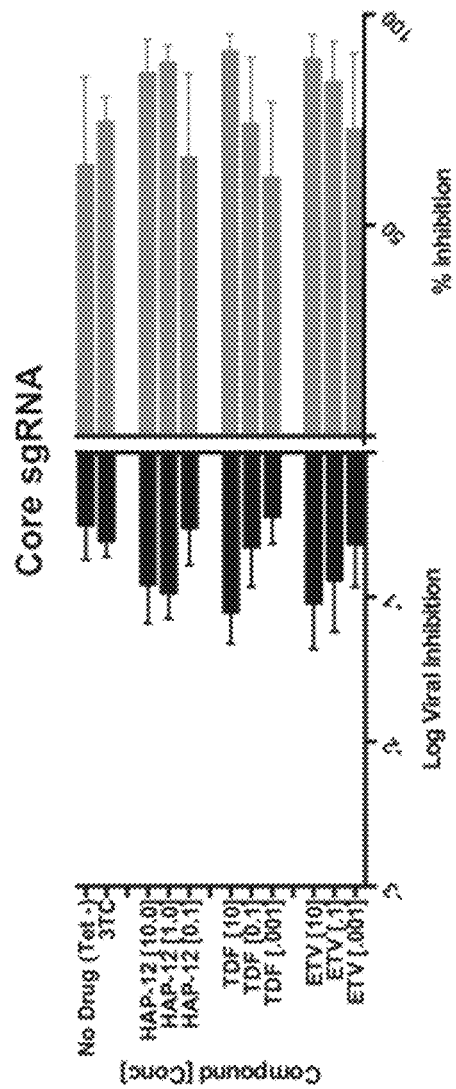

COMPOSITIONS FOR THE INACTIVATION OF VIRUS REPLICATION AND METHODS OF MAKING AND USING THE SAME

CROSS-REFERENCE TO RELATED APPLICATIONS

This patent application is a national stage filing under 35 U.S.C. 371 of International Application No. PCT/US2015/016354, filed Feb. 18, 2015, which claims the benefit of priority of U.S. Provisional Patent Application No. 61/940,883, filed Feb. 18, 2014, both of which are incorporated herein by reference in their entirety.

STATEMENT REGARDING FEDERALLY SPONSORED RESEARCH

This invention was made with United States government support awarded by the National Institutes of Health grant numbers R01 DA030086, R01 AI097376, T32 CA009111, P30 AI064518 and P30 AI050409. The United States has certain rights in this invention.

SEQUENCE LISTING

This application is being filed electronically via EFS-Web and includes an electronically submitted Sequence Listing in .txt format. The .txt file contains a sequence listing entitled "2015-02-18_5667-00184_ST25.txt" created on Feb. 18, 2015 and is 36,060 bytes in size. The Sequence Listing contained in this .txt file is part of the specification and is hereby incorporated by reference herein in its entirety.

INTRODUCTION

Current gene therapy approaches based upon targeted DNA endoculeases, such as zinc finger nucleases (ZFNs) and transcription activator-like effector nucleases (TALENs), are based upon custom built DNA binding domains. These technologies are unwieldy, difficult to execute, and are only capable of single target site cleavage. To target multiple DNA targets simultaneously, bacterial type II CRISPR/Cas9-based RNA-guided DNA endonucleases (RGNs) can be employed. These RGNs consist minimally of a Cas9 endonuclease loaded with a single guide RNA that is fully complementary to the desired DNA target sequence. In contrast to other targeted nucleases using custom engineered DNA binding domains designed to target a unique sequence, Cas9 proteins can be retargeted simply by expression of a distinct guide RNA. However, the *Streptococcus pyogenes* Cas9 RGN (SPCas9) greatly exceeds the packaging limit of ~4.8 kb for adeno-associated virus (AAV)-based vectors, which are currently the preferred gene delivery vectors for in vivo purposes. Thus smaller Cas9 proteins needed to be developed.

Although gene therapy with ZFNs has progressed through clinical trials in several cases, they are only capable of targeting a single locus and are known to have low specificity. The compositions of the present disclosure solve this problem by providing multiplex targeting to greatly extend editing efficiency beyond what is possible using ZFNs to permit not only gene disruption but also full gene deletion. In the context of virus-infected target cells, gene deletion could also be used for removal of a viral receptor or essential co-factor, rendering those cells refractory to infection. There are numerous tissues that are difficult to transduce where AAV is the sole capable option. It is in these tissues where CRISPR/Cas9/AAV will open up new gene therapy potentialities as an antiviral treatment option.

SUMMARY

CRISPR/Cas systems mediate bacterial adaptive immune responses that evolved to protect bacteria from bacteriophage and other horizontally transmitted genetic elements. Several CRISPR/Cas systems exist but the simplest variant, referred to as Type II, has a single effector DNA endonuclease, called Cas9, which is guided to its viral DNA target by two small RNAs, the crRNA and the tracrRNA. Initial efforts to adapt the CRISPR/Cas system for DNA editing in mammalian cells, which focused on the Cas9 protein from *Streptococcus pyogenes* (Spy), demonstrated that Spy Cas9 can be directed to DNA targets in mammalian cells by tracrRNA:crRNA fusion transcripts called single guide RNAs (sgRNA). Upon binding, Cas9 induces DNA cleavage leading to mutagenesis as a result of error prone non-homologous end joining (NHEJ). This system can be used to target DNA viruses for cleavage and eventual elimination of the virus from cells as shown and described herein.

Compositions for inactivation of viral replication, treating viral infection and treating viral induced cancer based on the CRISPR/Cas9 system and methods of making and using the compositions are provided herein. The compositions include recombinant constructs for generation of recombinant expression cassettes or vectors including viral vectors such as gene therapy vectors. The constructs include a first promoter operably connected to a first polynucleotide encoding a first single guide RNA and a second promoter operably connected to a second polynucleotide encoding a Cas9 polypeptide for targeting a sequence in a DNA virus or a virus with a DNA intermediate. The first single guide RNA includes a first portion complementary to a strand of a target sequence of a DNA virus and a second portion capable of interacting with the Cas9 polypeptide. The DNA viruses may be classified in a family selected from the group consisting of hepadnaviridae, herpesviridae, papillomaviridae and retroviridae.

Recombinant vectors and pharmaceutical compositions including viral vectors such as adeno-associated virus (AAV) or other viral vectors are also provided herein.

When the construct is introduced into cells harboring the DNA virus under conditions that allow expression of the first single guide RNA and the Cas9 polypeptide, the first single guide RNA targets the Cas9 polypeptide to the DNA virus and cleaves the target sequence. The double strand break in the DNA viral genome results in a reduction in gene expression of the gene encoded by the target sequence and may also result in inhibition of viral replication and loss of the viral genome from the cells.

In another aspect, methods of inhibiting viral replication or target sequence expression in a cell infected with a DNA virus are provided. The methods include contacting the cell with the recombinant vector or the constructs including polynucleotides encoding the single guide RNA and the Cas9 polypeptide in an amount effective to allow delivery of the recombinant vector to the cell and production of the single guide RNA and the Cas9 polypeptide. The single guide RNA and the Cas9 polypeptide mediate cleavage of the target sequence in the cell. The cleavage of the target sequence may result in loss of the DNA encompassing the target sequence, a reduction in gene expression of a gene encoded by the target sequence, reduction in expression of an unrelated gene product or introduction of a mutation in the target sequence. The methods may be used to treat a viral infection.

In still another aspect, a recombinant *Staphylococcus aureus* (Sau) Cas9 polypeptide of SEQ ID NO: 57 is provided and a codon optimized Sau Cas9 polynucleotide of SEQ ID NO: 55. The polynucleotide may include a polynucleotide encoding an affinity tag such as a FLAG tag. The polynucleotide may also include a poly (A) addition site and a nuclear localization signal. Other elements such as introns that may enhance expression of the polynucleotide may also be included in the polynucleotide. The Sau Cas9 polypeptide may include a nuclear localization signal or an affinity tag as described herein.

In yet a further aspect, recombinant constructs for expression of a single guide RNA are provided. In the constructs, a first polynucleotide encoding a mammalian or viral tRNA is operably connected to a second polynucleotide encoding the single guide RNA. This construct allows for the tRNA to direct RNA Polymerase III dependent production of a fusion RNA including the tRNA linked to the single guide RNA with a tRNase Z cleavage site. Action of the endogenous cellular tRNase Z enzyme cleaves the tRNA from the single guide RNA and allows for efficient production of the single guide RNA using a very small promoter element. Kits including these constructs are also included.

BRIEF DESCRIPTION OF THE DRAWINGS

FIG. 1 is a set of figures showing an Spy Cas9 HPV-18-specific sgRNA screen in which two sgRNAs were designed to target DNA sequences encoding the amino terminus of the HPV-18 E6 or E7 proteins, and screened to identify the most effective candidate.

FIG. 2 is a photograph of SURVEYOR assay showing HPV-18 E6 and E7-specific Spy Cas9 sgRNAs induce mutagenesis at the predicted cleavage site in the HPV-18 genome. E6 and E7 sgRNA and Spy Cas9 expression constructs were transfected and the SURVEYOR assay performed. The predicted size of the SURVEYOR cleavage product is indicated by an arrow. DNA markers (left lane) are indicated by base pairs.

FIG. 3 is a set of photographs showing that HPV-18 E6- and E7-specific RNA guided DNA endonucleases (RGNs) induce tumor suppressor gene expression in HeLa cells. HeLa cells were transfected with vectors expressing Spy Cas9 and HPV-18-specific sgRNAs, as indicated, and were processed for Western blot. These data are representative of 3 biological replicates. FIG. 3A shows a lysate that was probed for p53 and p21 expression, with endogenous β-actin used as a loading control. The Cas9 protein was detected by an antibody specific for the Flag epitope tag. FIG. 3B is similar to panel 3A, except this lysate was probed for the retinoblastoma protein (Rb). FIG. 3C shows the sequence of a mutant E6 expression construct designed to be resistant to cleavage by Spy Cas9 in the presence of E6sgRNA1. The mutations are in lowercase type and the PAM is underlined. The wild-type E6 partial sequence in FIG. 3C is presented as SEQ ID NO: 66 and the mutant E6 partial sequence showing the sequence changes is presented as SEQ ID NO: 67. FIG. 3D is a set of Western blots showing that expression of the cleavage resistant E6 gene reveals trans-complementation of p53 protein repression in the presence of Spy Cas9 and E6 sgRNA1. N.S., non-specific.

FIG. 4 is a set of figures showing that RGN-directed mutagenesis of either the E6 or E7 locus induces cell cycle arrest in G1.

FIG. 5 is a set of two graphs showing that lentiviral vectors expressing Spy Cas9 and sgRNAs specific for the HPV-18 E6 and E7 genes induce the death of cervical carcinoma cells. HeLa cells were transduced with a lentiviral vector expressing eGFP, to control for lentiviral toxicity (LCE) or a lentiviral vector expressing SpyCas9 and a non-specific sgRNA or E6- or E7-specific sgRNAs.

FIG. 6 is a set of Western blots showing that HPV-16-specific E6 and E7 RGNs rescue p21 and RB expression in the SiHa cervical carcinoma cell line. SiHa cells were transfected with an Spy Cas9 expression vector and the HPV-16 specific sgRNA constructs indicated and processed for Western blot.

FIG. 9 is a set of graphs showing antiviral activity of TDF, ETV, HAP12, and 3TC in HepAD38 cells. HepAD38 cells transduced with lentiviral vectors expressing various Cas9/sgRNA combinations were treated with 0.1 µM 3TC or with several concentrations (µM) of HAP12, TDF or ETV, as indicated in the y-axes. On day 7, total levels of secreted HBV DNA were measured by real-time PCR, and are here shown as both log viral (Left panel) and percent inhibition (right panel) of the level of HBV DNA replication seen in the positive control. All data were normalized to untreated cells expressing Cas9 and the N.S. sgRNA. FIGS. 9A, 9B, 9C and 9D show results obtained using HepAD38 cells transduced with lentivectors expressing the N.S., RT, surface Ag and core sgRNAs, respectively. Data are displayed as mean±SD of replicates.—Tet indicates absence of Tet in culture media; TDF, tenofovir disoproxil fumarate; ETV, entecavir; HAP12, capsid assembly effector 12; 3TC, lamivudine.

FIG. 10 shows a Western blot cross-talk experiment comparing an HSV-1 ICP0 specific sgRNA to an HBV reverse transcriptase specific sgRNA. An anti-FLAG antibody demonstrates Cas9 expression, and the anti-Rev antibody demonstrates highly specific elimination of the replicating plasmid reporter.

FIG. 11 is a set of figures showing that Spy sgRNAs can be expressed from tRNAs and function comparably to U6 promoter driven expression.

FIG. 12 is a set of figures showing that Nme sgRNAs can be expressed from tRNAs and function comparably to U6 promoter driven expression.

FIG. 13 is a set of figures showing that various tRNAs can express a functional Sau sgRNA.

DETAILED DESCRIPTION

Figure 1A:
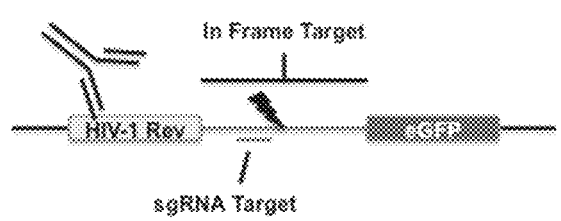
FIG. 1A is a schematic depicting the fusion protein-based reporter assay, which includes an amino-terminal HIV-1 Rev fragment that acts as an epitope tag, an in-frame HPV-18 derived target sequence, and a carboxy-terminal eGFP open reading frame (ORF). In other assays a firefly luciferase (FLuc) ORF was used in place of GFP.

Compositions for inactivation of viral replication, treating viral infection and treating viral induced cancers based on the CRISPR/Cas9 system are provided herein. In addition, methods of making and using the compositions are provided herein. CRISPR (clustered regularly interspaced short palindromic repeats) loci are found in a wide range of bacteria and have now been shown to be transcribed to generate a family of targeting RNAs specific for a range of different DNA bacteriophage that can infect that bacterium. In bacteria that express a type II CRISPR/Cas system, these phage-derived sequences are transcribed along with sequences from the adjacent constant region to give a CRISPR RNA (crRNA) which forms a complex with the invariant trans-activating crRNA (tracrRNA), using sequence complementarity between the tracrRNA and the invariant part of the crRNA. This heterodimer is then bound by the effector protein of the type II CRISPR/Cas systems, called Cas9. Cas9 has the ability to directly recognize a short DNA sequence, 5'-NGG-3' for the commonly used Streptococcus pyogenes (Spy) Cas9 protein, called the protospacer adjacent motif (PAM). The Cas9 protein scans a target genome for the PAM sequence and then binds and queries the DNA for full 5' sequence complementarity to the variable part of the crRNA. If detected, the Cas9 protein directly cleaves both strands of the target bacteriophage DNA ~3 bp 5' to the PAM, using two distinct protein domains: the Cas9 RuvC-like domain cleaves the non-complementary strand, while the Cas9 HNH nuclease domain cleaves the complementary strand. This dsDNA break then induces the degradation of the phage DNA genome and blocks infection. Thus CRISPR/Cas based systems are both highly specific and allow facile retargeting to new genomic loci.

A key step forward in making the Spy Cas9 system more user-friendly for genetic engineering in human cells was the demonstration that the crRNA and tracrRNA could be linked by an artificial loop sequence to generate a fully functional small guide RNA (sgRNA) ~100 nt in length. Further work, including mutational analysis of DNA targets, has revealed that sequence specificity for Spy Cas9 relies both on the PAM and on full complementarity to the 3' ~13 nt of the ~20 nt variable region of the sgRNA, with more 5' sequences making only a minor contribution. Spy Cas9 therefore has an ~15 bp (13 bp in the guide and 2 bp in the PAM) sequence specificity which, while high, is generally not sufficient to entirely avoid a small number of potential off-target cleavage sites in the large genome present in human cells. Nevertheless, this is a high level of specificity and a small number of off-targets in non-transcribed regions of the human genome appear unlikely to be highly problematic, especially if due diligence is devoted to bioinformatic analysis of potential off-target cleavage sites.

This concern can be dealt with by mutating the Cas9 protein to inactivate one of the two independent HNH and RuvC nuclease sites, to generate a so-called "nickase" (Cong et al., 2013; Ran et al., 2013). It is then possible to target two nickase Cas9s to two closely proximal (<20 bp) sites on the two strands of the DNA target. Once nicked on both strands, the DNA will fall apart to give a staggered dsDNA break, analogous to what is obtained upon cleavage at a single recognition sequence using wild-type Spy Cas9, except that the DNA target specificity is now ~30 bp for Spy Cas9, amply sufficient to ensure complete specificity even in a large genome, such that present in human cells. In this embodiment, the two single guide RNA target sequences are suitably designed to target opposite strands of the target sequence and are designed such that the Cas9 nickases will cut within about 30 bp of each other. Suitably, the cleavage sites are less than 40, 35, 30, 25, 20, 15, 10, or 5 nucleotides from each other such that the single strand cuts result in a deletion or mutation of some part of the DNA sequence rather than DNA repair.

CRISPR systems have been identified and characterized from many different bacteria and any of these Cas9 enzymes may be used in the methods described herein. For example Cas9 proteins from any of *Corynebacter Sutterella, Legionella, Treponema, Filifactor, Eubacterium, Streptococcus, Lactobacillus, Mycoplasma, Bacteroides, Flaviivala, Flavobacterium, Sphaerochaeta, Azospirillum, Gluconacetobacter, Neisseria, Roseburia, Parvibaculum, Staphylococcus, Nitratifractor, Mycoplasma* and *Campylobacter* may be used. Several Cas9 constructs are available from Addgene.

In the Examples, CRISPR systems and Cas9 proteins from *Streptococcus pyogenes* (Spy), *Neisseria meningitides* (Nme) and *Staphylococcus aureus* (Sau) are used. Each of these proteins relies on a distinct recognition site or PAM. The PAM for Spy Cas9 is 5'-NGG-3', for Nme it is 5'-NNNNGATT-3' and for Sau the PAM is identified herein as 5'-NNGRRT-3', where R is purine. Each has a distinct sgRNA scaffold sequence making up the 3' portion of the single guide RNA. These scaffolds are shown as SEQ ID NOs: 36-38, respectively. The length of the target sequence specific 5' portion of the sgRNA also varies between the Cas9 enzymes as well. Spy uses a 13-15 nucleotide target sequences. Nme and Sau use a 18-24 nucleotide target sequence.

As demonstrated in the Examples, a codon optimized polynucleotide encoding Sau Cas9 is provided herein as SEQ ID NO: 55. The codon optimized Sau Cas9 shows good expression in eukaryotic cells and may be combined with an affinity tag such as a FLAG tag and/or a nuclear localization signal (NLS) to allow for targeting the Cas9 to the nucleus. The Sau Cas9 polypeptide sequence with the FLAG tag and NLS is shown as SEQ ID NO: 57. The polynucleotide sequence of a combination FLAG tag and NLS is provided as SEQ ID NO: 54. Other NLSs are available to those of skill in the art and include but are not limited to the sequences provided in SEQ ID NOs: 59-62. Those of skill in the art will appreciate that the polynucleotide sequence will require a poly (A) addition site such as SEQ ID NO: 56 and a promoter/enhancer to allow for expression of the Cas9 protein. Recombinant constructs and expression constructs for Cas9 are described in more detail below.

In the CRISPR system, the Cas9 enzyme is directed to cleave the DNA target sequence by the sgRNA. The sgRNA includes at least two portions having two functions. The first portion is the targeting portion of the sgRNA and it is at the 5' end of the sgRNA relative to the second portion. The first portion of the sgRNA is complementary to a strand of the target sequence. The target sequence is immediately 5' to the PAM sequence for the Cas9 on the target DNA. The portion of the sgRNA that is complementary to the target sequence may be between 10 nucleotides, 13 nucleotides, 15 nucleotides, 18 nucleotides, 20 nucleotides, 22 nucleotides or 24 nucleotides in length or any number of nucleotides between 10 and 30. The portion of the sgRNA complementary to the target sequence should be able to hybridize to the sequences in the target strand and is optimally fully complementary to the target sequence. The exact length and positioning of the complementary portion of the sgRNA will depend on the Cas9 enzyme it is being paired with. The Cas9 enzyme selected will require that the sgRNA is designed specifically for use with that enzyme and will control the design of the sgRNA. Several sgRNAs targeting portions are described herein and include but are not limited to those provided in SEQ ID NOs: 1-35 and 63-65.

The second portion of the sgRNA which is at the 3' end of the sgRNA is the scaffold that interacts with the Cas9 enzyme. The scaffold sequence is specific for each Cas9. The scaffold sequences used herein are shown as SEQ ID NOs: 36-38. In one embodiment, a vector or construct comprising one or more sgRNAs is provided. The sgRNAs in this vector may include a sgRNA lacking a first portion complementary to a target sequence, but instead may include cloning sites upstream of the scaffold or second portion of the sgRNA. The vector may also include the Cas9 polynucleotide and promoters or other transcriptional elements to allow for expression of the sgRNA and the Cas9 polypeptide. The cloning site would allow for streamlined incorporation of a targeting portion of the sgRNA to allow for quick production of new CRISPR systems targeting new DNA sequences. Exemplary sgRNA scaffolds including restriction enzyme recognition sites for simple incorporation of a targeting portion are provided as SEQ ID NO: 39 and 40. These sequences have the Sau Cas9 specific sgRNA scaffold sequence downstream of two repeated restriction sites selected from BsmB1 and Bbs1, respectively. Other restriction sites can be used to make construction of specific sgRNAs a quick streamlined process.

The Targets:

Persistent infections caused by several pathogenic human DNA viruses, such as herpes simplex viruses types 1 and 2 (HSV-1 and HSV-2) and hepatitis B virus (HBV), have no known cure, and RGNs represent a way to eliminate the viral genetic material that is essential for chronic infection. HIV-1 is a retrovirus, but is capable of initiating a chronic infection wherein a DNA copy of the viral genome is integrated into the cellular genome. These integrated viruses serve as a reservoir of virus that is not subject to the anti-viral treatments in use. Other DNA viruses such as human papilloma virus (HPV) and Kaposi's sarcoma associated herpesvirus (KSHV) are found in cancers. Targeting of these viruses may reduce the risk of cancer or treat the cancer. Thus the viruses targeted herein may be selected from the hepadnaviridae, herpesviridae, papillomaviridae and retroviridae.

HBV

HBV infects over 300 million individuals globally, and in endemic countries it is predominantly transmitted perinatally. Chronic HBV cases often progress to severe complications such as hepatocellular carcinoma or cirrhosis, resulting in 563,000 deaths in 2002. A vaccine for HBV is available, but it is unhelpful to individuals with a pre-existing infection. An essential viral dsDNA intermediate termed covalently closed circular DNA (cccDNA) has an exceptionally high half-life in infected liver cells, which enables intracellular persistence. This episomal DNA intermediate is pivotal to viral replication, and current treatments such as reverse transcriptase inhibitors do not result in its clearance. In an effort to eliminate these treatment-refractory dsDNA molecules from the infected liver, destruction of this hyperstable HBV viral DNA intermediate is required.

In the Examples, we demonstrate that HBV genomic DNA molecules, including the cccDNA, can be effectively cleaved and mutationally inactivated by Cas9/sgRNA combinations in cells undergoing either acute or chronic infections. In the case of HBV, Cas9/sgRNA combinations targeted to the HBV reverse transcriptase (RT), core or surface antigen genes (see SEQ ID NOs: 1-7) result in a marked inhibition of viral protein expression and loss of viral DNA molecules, including the covalently closed circular DNA (cccDNA) molecules that play a critical role in HBV persistence in patients even in the face of treatment with nucleoside-based inhibitors of RT function. AAV may be ideal for this task, as several AAV serotypes are naturally hepatotropic and even more highly hepatotropic AAV vectors have recently been isolated by "shuffling" AAV sequences in vivo.

HSV

The herpesviridae represent a large family of viruses and include herpes simplex virus type 1 (HSV-1), herpes simplex virus type 2 (HSV-2), Epstein Barr Virus (EBV), human cytomegalovirus (hCMV), Varicella zoster virus (VZV), Kaposi's sarcoma associated herpesvirus (KSHV) as well as several other human herpesviruses. Similar to HBV, herpesviruses once acquired remain with the host for life, and, in the case of HSV-1 and HSV-2, typically remain latent in the form of stable dsDNA episome in the nuclei of sensory neurons.

HSV-1, for example, remains latent in the trigeminal ganglia of the infected individual. HSV-1 infects ~70% of the U.S. population and about one third of affected individuals suffer from recurrent, primarily oral, cold sores. During latency, the only region of the genome that is actively transcribed encodes the latency associated transcript LAT, which is processed to give rise to a single long non-coding RNA of ~2.1 kb, as well as 8 virally encoded miRNAs, that together are thought to regulate exit from latency. Expression of viral transcription activators including ICP0 and ICP4 is required for viral reactivation. While often no more than an irritation, HSV-1 infections can also lead to serious morbidity and HSV-1 keratitis represents the most common form of infectious blindness in the USA. A closely related virus, HSV-2, that is found in ~20% of the US population, has a similar replication cycle but generally is sexually transmitted and often infects the genital mucosa. Drugs such as valacyclovir can inhibit active lytic replication but have no tangible effect on the latently infected viral reservoir. As shown in the Examples, HSV genomic molecules can be effectively cleaved and mutationally inactivated by Cas9/sgRNA combinations in cells. In the Examples, ICP0 and ICP4 were targeted and the sgRNAs used are found as SEQ ID NO: 16-19 and 63. AAV is able to infect the trigeminal ganglion cells via known means. Latent HSV-1 infections of neurons in the mouse trigeminal ganglia (TGs) can be readily established and it is therefore possible to test whether transduction of these same TGs with AAV-based vectors encoding HSV-1-specific Cas9/sgRNA combinations will result in a detectable reduction in viral DNA load and an inhibition in the ability of latent HSV-1 to reactivate after explant and culture of the infected TGs.

Other DNA Viruses

A number of other DNA viruses are associated with serious human diseases including Epstein-Barr virus (EBV), Kaposi's sarcoma-associated herpesvirus (KSHV) and Merkel cell polyomavirus (MCPyV) as well as others. Of these, perhaps the most relevant is EBV, which is the etiologic agent of several cancers, including an epithelial cell tumor called nasopharyngeal carcinoma (NPC) that is highly prevalent in southern China and Southeast Asia. In NPC cells, EBV is found in a form of viral latency that nevertheless involves the expression of several viral nonstructural proteins and microRNAs. EBV+NPCs share a number of characteristics with HPV-16+ head and neck (H&N) cancers and, as in the latter case, the continued presence and transcription of the viral, in this case EBV, genome is thought to be essential for tumor survival. It has already been demonstrated that EBV episomes are readily disrupted and destroyed by specific Spy Cas9/sgRNA combinations and it seems likely that NPC cells would be excellent targets for transduction in vivo using Sau Cas9/sgRNA-based AAV vectors specific for the EBV genome. As shown in the Examples, sgRNAs targeting EBV have been designed and shown to cleave the intended target sequence. The sgRNAs used in the Examples are specific for EBV FR (family of repeats), DS (direct symmetry), EBNA-1 (EBV nuclear antigen-1), Qp promoter, and LMP-1 (latent membrane protein-1). The sgRNA targeting sequences are shown as SEQ ID NO: 20-27.

HPV

Humans are infected by a wide variety of HPVs that, while normally innocuous, can also give rise to warts on the skin or genitalia. Most HPV variants replicate as episomes in the basal epithelial layer of the skin, where the virus expresses exclusively non-structural proteins. When the infected precursor epithelial cell migrates towards the surface of the epidermis and undergoes differentiation into a keratinocyte, the productive HPV replication cycle is activated leading to the release of infectious HPV virions. Most HPVs are non-pathogenic yet there are also a small number of so-called high-risk HPV serotypes, of which the most prominent are HPV-16 and HPV-18, which together cause ~70% of all cervical cancers. In most HPV induced cancers, the HPV episome is found clonally integrated into the cell genome in a manner that destroys or deletes the viral E2 gene. One key activity of E2 is to limit the expression of the HPV oncogenes E6 and E7, and disruption of E2 during integration into the host cell genome can lead to high, constitutive levels of E6 and E7 expression. E6 functions to bind and destabilize the p53 tumor suppressor while E7 similarly binds and destabilizes the Rb tumor suppressor and these two functions play a critical role in the maintenance of HPV-transformed cells. Cancers associated with HPV infection include cervical carcinomas, which are almost always HPV-positive, as well as a substantial fraction of head and neck (H&N) cancers as well as anal cancers.

In the case of HPV, the efficient mutational inactivation of the viral E6 gene, which normally functions to block the activity of the cellular tumor suppressor p53, results in activation of the p53 transcription factor and its downstream effectors, resulting in cell cycle arrest and the apoptotic death of HPV-transformed cells. In the Examples, we demonstrate that inactivation of the E6 gene in the HPV-18+ cervical carcinoma cell line HeLa or the HPV-16+ cell line SiHa using Spy CRISPR/Cas results in induction of p53 expression followed by the expression of downstream targets of this cellular transcription factor, including the CDK inhibitor p21 and several activators of apoptosis, leading to cell cycle arrest and cell death. Similarly, we demonstrated that disruption of the E7 gene using CRISPR/Cas results in the increased expression of Rb, formation of Rb/E2F heterodimers and then the induction of cellular genes that induce senescence and cell death. The sgRNA target sequences used are shown as SEQ ID NOs: 8-15. The delivery of CRISPR/Cas combinations specific for HPV E6 and/or E7 by direct injection of high titer AAV vector preparations into the HPV+ tumors has the potential to serve as a novel, highly specific and effective therapy for chemoresistant HPV-16 induced anal and H&N tumors.

HIV-1

While highly active antiretroviral therapy (HAART) can reduce HIV-1 replication to levels below the detection limit, HIV-1 persists as a latent infection in a small number of resting CD4+ memory T cells. In these long lived cells, intact integrated HIV-1 proviruses persist in a transcriptionally silent state that is refractory to both drugs and host immune responses. However, these memory T cells can be reactivated by an appropriate recall antigen, resulting in induction of a productive viral replication cycle. If this occurs after drug treatment has been stopped, HIV-1 will rapidly spread through the available CD4+ T cells and rekindle the same level of virus replication that was seen prior to antiviral drug treatment.

Efforts to purge the pool of latently infected cells have focused on two strategies. On the one hand, several groups have attempted to activate latent HIV-1 proviruses using drugs, including histone deacetylase inhibitors and PKC agonists. However, this strategy has not proven able to activate HIV-1 in a high percentage of latently infected cells. An alternative strategy would be to directly target and destroy latent proviruses using HIV-1-specific CRISPR/Cas combinations. In principle, the HIV-1 provirus is a perfect target for CRISPR/Cas as there is only a single proviral copy in the infected cell and, in the presence of antiviral drugs, no spread of the virus is possible. We show in the Examples that expression of HIV-1 specific Cas9/sgRNA combinations targeting Tat or TAR is capable of cleaving the virus and blocking HIV replication. The sgRNA targeting sequences used are shown as SEQ ID NOs: 30-35.

Viral Vectors for Delivery of CRISPR/Cas System

As noted in the above discussions of the targeted viruses, we believe that CRISPR/Cas-based approaches to the in vivo treatment of DNA virus infections will require a gene delivery vector to deliver the Cas9 and sgRNAs to the infected cells and that the development of vectors based on adeno-associated virus (AAV) may be optimal. Other gene delivery vectors including retrovirus, a lentivirus, an adenovirus or an adeno-associated virus may also be used. In the Examples we used a lentiviral vector and have developed AAV vectors as well. The advantage of AAV vectors is that they can generally be concentrated to titers of ≥$10^{14}$ viral particles per ml, a level of vector that has the potential to transduce all virus-infected cells in a patient, especially if these are all found in a single location, e.g., in the liver or specific neurons (Kotterman and Schaffer, 2014). Moreover, AAV-based vectors have a well-established record of safety and do not integrate at significant levels into the target cell genome, thus avoiding the potential for insertional activation of deleterious genes.

The problem with this approach is that AAV vectors have a maximum packaging capacity of ~4.7 kb, and this includes the AAV inverted terminal repeats, which together occupy ~290 bp, leaving only ~4.4 kb for heterologous DNA. As the Spy Cas9 gene, including an essential added nuclear localization signal (NLS), is ~4.2 kb in size, this does not leave enough room for a pol II promoter and poly(A) addition site for Cas9 expression as well as a pol III promoter and sgRNA sequence.

One way forward is to use one of the many smaller Cas9 proteins encoded by other bacterial species. In particular, *Neisseria meningitidis* (Nme) encodes a Cas9 protein with the PAM sequence 5'-NNNNGATT-3' while *Staphylococcus aureus* (Sau) encodes a Cas9 with the PAM sequence 5'-NNGRRT-3', where R is purine. Both proteins are encoded by genes ~3.2 kb in length, leaving room for two sgRNA cassettes, in addition to all required regulatory elements, in an AAV vector context. In our hands, Sau Cas9 is at least as active, or possibly more active, than Spy Cas9 on the same DNA target sequence and the sequence specificity of Sau Cas9 appears to be comparable to Spy Cas9.

tRNAs as an Effective Means of Expressing the sgRNA

Previous work has focused on using the U6 pol III promoter to drive sgRNA transcription. The U6 promoter, while very effective, is ~254 bp long and two U6 promoters would therefore require over 10% of the entire packaging capacity of an AAV vector. It is therefore desirable to identify equally effective pol III-dependent promoters that are much smaller than U6. In the Examples, we report that tRNA promoters, of human or viral origin, can be used to express high levels of sgRNAs specific for a wide range of DNA targets and bacterial Cas9 proteins.

Figure 11A:
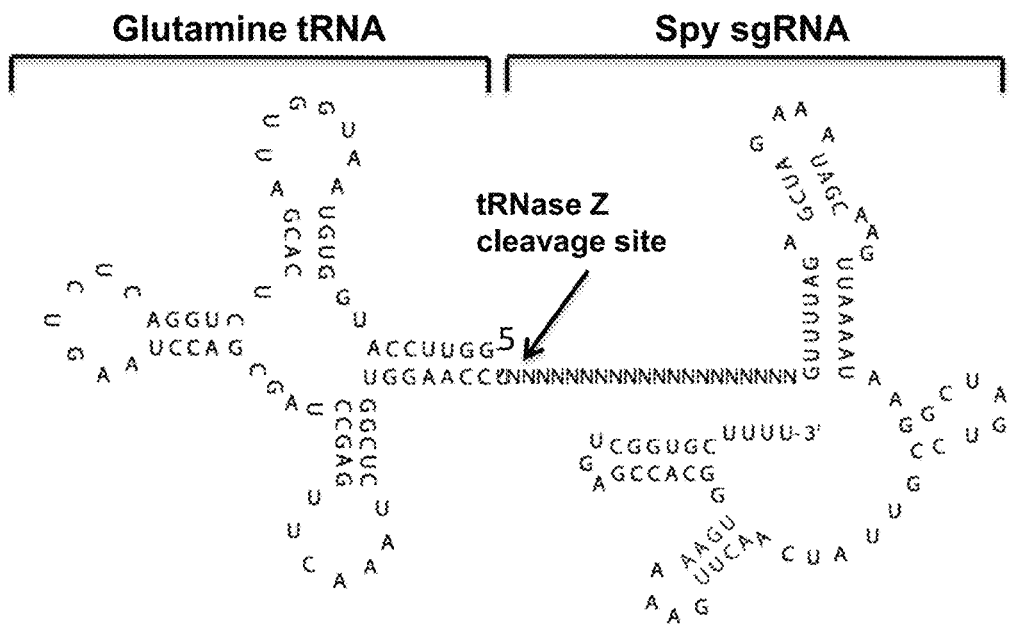
FIG. 11A is a schematic of a glutamine tRNA-sgRNA fusion with the indicated tRNase Z cleavage site. The "N" nucleotides represent the sgRNA targeting sequence (See SEQ ID NO: 41 and 36).

Previously, we have demonstrated that mouse γ-herpesvirus 68 (MHV68) encodes several ~60-nt long pre-microRNA (pre-miRNA) molecules that are initially transcribed as a fusion transcript consisting of a 5' viral tRNA moiety fused to a 3' pre-miRNA hairpin. These are then precisely separated due to cleavage by the cellular enzyme tRNase Z, which normally functions to define the precise 3' end of cellular tRNAs. We have also demonstrated that human tRNAs, when fused to a pre-miRNA hairpin of human or viral origin, gives rise to both the pre-miRNA intermediate and a functional mature miRNA and this again requires processing by tRNase Z to release the tRNA from the pre-miRNA. We therefore wondered whether human tRNAs could also be used to generate functional sgRNAs via a precursor tRNA fusion intermediate, as schematically shown in FIG. 11A. When compared to previously described tRNA:pre-miRNA fusion transcripts, this tRNA:sgRNA fusion differs in that the sgRNA is both significantly larger (~101 nt vs. ~60 nt) and folded into a more complex secondary structure.

As reported in the Examples, the tRNAs of mammalian or viral origin were capable of driving expression of the sgRNA. In most cases the tRNA:sgRNA was cleaved by tRNase Z to produce the sgRNA and the sgRNAs produced were shown to be active. The tRNAs tested are shown as SEQ ID NO: 41-50 and some were more active and produced higher levels of sgRNA than others as shown in the Examples. This technique represents a means of expressing the sgRNA using much smaller promoter elements to drive expression of the sgRNA and would be advantageous if using vectors with small carrying capacity such as AAV. These tRNA:sgRNA constructs may include the sgRNAs lacking the target portion and instead including restriction enzyme sites upstream of the scaffold section of the sgRNA for insertion of diverse target portions. These tRNA:sgRNA constructs may be included in kits for developing novel CRISPR/Cas9 targeting systems.

Constructs and Vectors

Reference to "recombinant" nucleic acid or vector indicates the presence of two or more nucleic acid regions not naturally associated with each other.

The terms "expression cassette" "expression construct" or "expression vector" refer to a nucleic acid molecule which comprises at least one nucleic acid sequence that is to be expressed, along with its transcription and optionally also translation control sequences. Changing the expression cassette will cause the vector in which it is incorporated to direct the expression of a different sequence or combination of sequences. Because of the restriction sites being engineered to be present at the 5' and 3' ends, the cassette can be easily inserted, removed, or replaced with another cassette.

The terms "operably linked" or "operably connected" are used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is said to be "operably linked to" or "operatively linked to" or "operably associated with" or "operably connected to" the regulatory elements, meaning that the gene or coding region is controlled or influenced by the regulatory element. Regulatory elements including promoters, enhancers, trans-activating factors are encompassed herein.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, mice, chickens, amphibians, reptiles, and the like. Preferably, the subject is a human patient. More preferably, the subject is a human patient suffering from a viral infection or a cancer induced by or related to infection with a virus.

As used herein, the term "gene therapy" means the transfer of nucleic acid compositions into cells of a multicellular eukaryotic organism, be it in vivo, ex vivo or in vitro. The term "gene therapy" should not be limited to the purpose of correcting metabolic disorders, but be interpreted more as a technical term for the transfer of nucleic acid compositions, such as expression cassettes or minigenes, for therapeutic purposes in general, independent of a specific therapeutic purpose. Therefore, the term "gene therapy" would include—without limitation—correction of metabolic disorders, cancer therapy, vaccination, monitoring of cell populations, cell expansion, stem cell manipulation, viral infections etc. by means of transfer of nucleic acid compositions.

Expression Cassette

One aspect of the present disclosure provides a recombinant construct or expression cassette comprising, consisting of, or consisting essentially of a first promoter operably connected to a first polynucleotide encoding a first single guide RNA and a second promoter operably connected to a second polynucleotide encoding a Cas9 polypeptide. The sgRNA includes a first portion (suitably the 5' end of the sgRNA) complementary to a strand of a target sequence of a DNA virus and a second portion (suitably the 3' end of the sgRNA) capable of interacting with the Cas9 polypeptide. In one embodiment, the recombinant construct includes an inverted terminal repeat (ITR) flanking the construct or cassette described herein for packaging in a viral vector such as an AAV vector. The construct or expression cassette may be organized from 5' to 3' as follows and include a first inverted terminal repeat followed by an RNA polymerase III dependent promoter operably linked to a single guide RNA, an RNA polymerase II dependent promoter/enhancer operably linked to a polynucleotide encoding a Cas9 polypeptide, and a second inverted terminal repeat.

While it is within the scope of the present disclosure that any RNA polymerase promoter may be used, in some embodiments, the RNA polymerase promoter comprises an RNA polymerase III promoter inserted at the 5' end of the vector to avoid the transcriptional interference known to occur when RNA polymerase III promoters are located 3' to RNA polymerase II promoters. In certain embodiments, the RNA polymerase III promoter is selected from the group consisting of the cellular H1 and U6 promoters. In other embodiments, the RNA polymerase III promoters used are the tRNAs described above and shown to function in the Examples.

The RNA polymerase III promoter is operably linked to a single guide RNA (sgRNA). In one embodiment, the sgRNA comprises a 5' portion that is complementary to a sense strand of a target DNA sequence and a conserved, structured 3' terminus that enables Cas9 binding. The target DNA may comprise any DNA sequence that encodes for a gene that is desired to be targeted for mutation and/or deletion. In some embodiments, the target DNA sequence comprises a viral DNA sequence. Potential target sequences must be located just 5' to the PAM sequence recognized by the Cas9 polypeptide in the target DNA sequence. The expression cassette may comprise only one RNA polymerase III promoter operably linked to a sgRNA or may include two or more RNA polymerase III promoter ~sgRNA combinations in an expression cassette. The use of two or more sgRNAs targeting two target sequences in a single gene or target sequence is sufficient to allow for the deletion of an entire locus.

The expression cassette comprises a promoter/enhancer to drive the Cas9 expression at the 3' end of the vector. Promoter/enhancers are known in the art as DNA sequences that recruit RNA polymerase II to initiate RNA transcription and are within the scope of the present disclosure. One skilled in the art can readily determine which would be appropriate for use within the present disclosure. In certain embodiments, the promoter/enhancer comprises a HSV-TK Promoter. In other embodiments, the promoter/enhancer comprises a CMV Immediate Early (CMV-IE) Promoter/Enhancer. Suitable promoters include, but are not limited to, EFS, hCMV or mCMV immediate early, CBA, hSynapsin, HSV TK, SV40 early and LSP. The Cas9 expression cassette may also include an intron between the promoter and at the 5' end of the Cas9 polynucleotide. Introns have been shown to increase the expression of some but not all polypeptides when inserted into the 5' untranslated region of an mRNA transcribed from an expression construct. For example, the Rat preproinsulin intron (SEQ ID NO: 53 cloned in the 5' untranslated region of the Sau Cas9 was shown in the Examples to increase expression of Cas9.

Another aspect of the present disclosure provides an expression cassette comprising, consisting of, or consisting essentially of, from 5' to 3': a first inverted terminal repeat (ITR), a first RNA polymerase III promoter operably linked to a first sgRNA; a second RNA polymerase III promoter operably linked to a second sgRNA; a Promoter/Enhancer operably linked to a Cas9 expression sequence, and a second inverted terminal repeat. For each of the sequences provided herein, sequences 90%, 93%, 95%, 97%, 98%, or 99% identical to the sequences provided herein are also encompassed. Those of skill in the art will appreciate that small modifications in nucleotide or amino acid sequences can be made and the function maintained based on knowledge of the sequence.

General Methods

The practice of the present disclosure will employ, unless otherwise indicated, conventional methods of virology, microbiology, molecular biology and recombinant DNA techniques within the skill of the art. Such techniques are explained fully in the literature; (see, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.)

One aspect of the present disclosure provides a recombinant vector comprising, consisting of, or consisting essentially of an expression cassette as described herein. Yet another aspect of the present disclosure provides a method of making a recombinant vector comprising, consisting of, or consisting essentially of inserting into the vector or expression cassette as described herein.

As used herein, the term "vector" is meant to include any element, such as a plasmid, phage, transposon, cosmid, chromosome, artificial chromosome (YAC or BAC), virus, virus capsid, virion, etc., which is capable of transferring and/or transporting a nucleic acid composition to a host cell, into a host cell and/or to a specific location and/or compartment within a host cell. Thus, the term includes cloning and expression vehicles, as well as viral and non-viral vectors and potentially naked or complexed DNA. However, the term does not include cells that produce gene transfer vectors such as retroviral packaging cell lines.

In some embodiments, the vector comprises an adeno-associated virus (AAV) vector. For purposes of this invention, by "recombinant virus", "recombinant virion", "recombinant vector" or "recombinant viral vector" is meant a virus that has been genetically altered, e.g., by the addition or insertion of a heterologous nucleic acid composition into the particle. In some embodiments, the recombinant virus comprises AAV. Thus, for example, a "recombinant AAV virion" is used synonymously with a "recombinant AAV vector". A recombinant AAV vector comprises at least an AAV capsid ("the outer shell") and a recombinant AAV (vector) genome, which is harbored inside the capsid.

For purposes of this invention, by "recombinant AAV genome" or "recombinant AAV vector genome" is meant an AAV genome comprising heterologous sequences. In general, recombinant AAV genomes are designed in a fashion such that all viral genes are replaced by heterologous sequences (e.g., an expression cassette or minigene), leaving intact only the essential cis elements of the genome, i.e., the inverted terminal repeats (ITRs), DNA packaging signal, and the replication origin. Alternatively, the essential cis elements of the genome can be those as described in prior art by (Musatov et al.: "A cis-acting element that directs circular adeno-associated virus replication and packaging."; J Virol. December 2002; 76(24):12792-802). The recombinant AAV genome is part of the recombinant AAV vector.

Another aspect of the present disclosure provides methods of making a recombinant vector comprising, consisting of, or consisting essentially of a recombinant expression cassette in accordance with one embodiment of the present disclosure, the method generally comprising the steps of (1) Introducing an (r)AAV vector construct into a producer cell (e.g., 293 cells); (2) Introducing an "AAV packaging construct" into the producer cell, where the packaging construct comprises the recombinant expression cassette or construct as described herein and any AAV coding regions (e.g., rep and cap sequences) capable of being expressed in the producer cell to complement AAV packaging functions missing from the AAV vector construct; (plasmid-based AAV packaging constructs are often referred to as "trans" plasmids); (3) Introducing one or more helper viruses and/or accessory function vector constructs into the producer cell, wherein the helper virus and/or accessory function vector constructs provide accessory functions capable of supporting efficient recombinant AAV ("rAAV") virion production in the producer cell; frequently used producer cells are HEK 293 cells and Sf9 cells; and (4) Culturing the producer cell to produce rAAV virions; (5) Harvesting the cells and isolating/purifying the rAAV virions.

The AAV vector construct, AAV packaging construct and the helper virus or accessory function vector construct can be introduced into the producer cell either simultaneously or serially, using standard transfection techniques. Introduction of the molecules (as plasmids or viruses) into the producer cell may also be accomplished using techniques known to the skilled artisan and are discussed throughout the specification. In the preferred embodiment, standard transfection techniques are used, e.g., calcium phosphate transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins). Thus produced, the rAAV may be used to prepare the compositions and kits described herein, and used in the method of the invention.

Recombinant AAV vector constructs (e.g., a recombinant AAV vector comprising an expression cassette as described herein) are constructed using known techniques to at least provide, as operatively linked components in the direction of transcription, a first inverted terminal repeat (ITR), a first RNA polymerase III promoter operably linked to a first sgRNA; optionally a second RNA polymerase III promoter operably linked to a second sgRNA; a Promoter/Enhancer (a RNA Polymerase II dependent promoter) operably linked to a Cas9 expression sequence, and a second inverted terminal repeat. The resulting construct which contains the operatively linked components is bounded (5' and 3') with functional AAV ITR sequences.

The 5' and 3' termini of the expression cassette each comprise an inverted terminal repeat region (ITR) which is involved in the multiplication and packaging of the vector, e.g. a recombinant AAV vector. AAV ITRs used in the vectors of the invention need not have a wild-type nucleotide sequence, and may be altered, e.g., by the insertion, deletion or substitution of nucleotides. Also, in some embodiments, the 5'-ITR and the 3'-ITR might be derived from different serotypes, e.g., an AAV2-5'-ITR and an AAV5-3'-ITR.

Additionally, AAV ITRs may be derived from any of several AAV serotypes, including AAV1, AAV2, AAV5, AAV4, AAV5, AAV6, AAV7, AAV5, AAV5, AAV10, AAV11, avian AAVs, bovine AAVs etc. The 5' and 3' ITRs which flank a selected transgene expression cassette in an AAV vector construct need not necessarily be identical or derived from the same AAV serotype. Thus, rAAV vector design and production allow for exchanging the capsid proteins between different AAV serotypes. Homologous vectors comprising an expression cassette flanked by e.g., AAV2-ITRs and packaged in an AAV2 capsid, can be produced as well as heterologous, hybrid vectors where the transgene expression cassette is flanked by e.g., AAV2 ITRs, but the capsid originates from another AAV serotype such as AAV5 for example.

Figure 16:
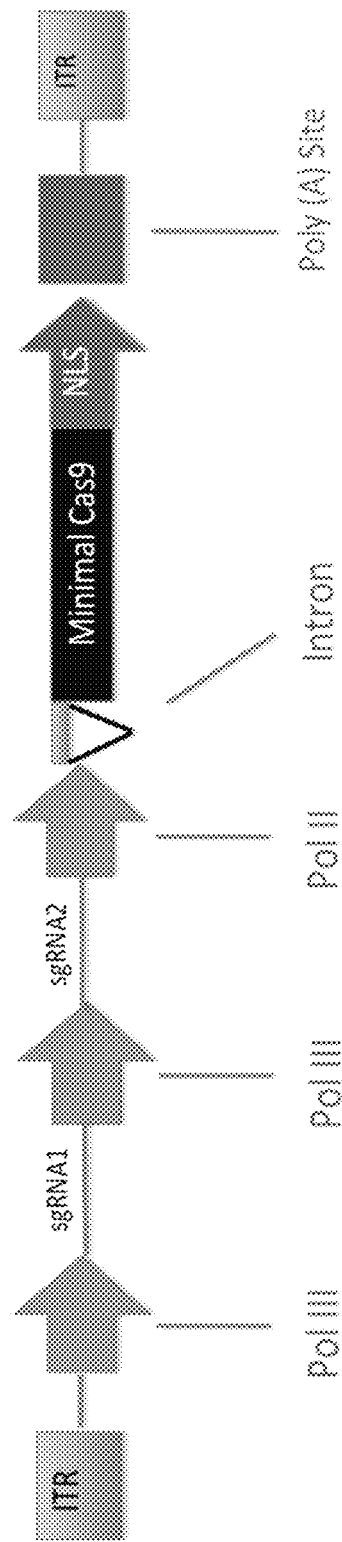
FIG. 16 is a schematic of the structure of an AAV-based vector containing two Pol III-dependent promoters driving two sgRNAs and a Pol II-dependent promoter driving the expression of a Cas9 protein linked to a nuclear localization signal (NLS). This construct also contains two AAV inverted terminal repeats (ITRs), an intron in the 5' UTR region of the Cas9 gene and a synthetic poly(A) addition site. Possible Pol III-dependent promoters include the U6 and H1 promoters as well as any of the tRNA promoters described herein. Possible Pol II-dependent promoters include viral promoters (e.g., the CMV immediate early promoter) or cellular promoters (e.g., the EIF1α promoter).

As shown in the Examples and specifically in FIG. 16, an AAV vector insert within the scope of the invention as described herein includes the terminal ITRs (inverted terminal repeats) required for AAV vector packaging flanking the insert. From 5' to 3' end, the vector contains two sgRNA expression cassettes, with the sgRNA transcribed by an RNA polymerase III dependent promoter such as the human U6 promoter, or by a human tRNA promoter, eg; a glutamine tRNA or proline tRNA promoter, or by an MHV68-derived tRNA promoter. Next is the RNA polymerase II-dependent promoter/enhancer used to drive Cas9 mRNA expression. Possible examples of suitable promoters include the eukaryotic translation initiation factor 2 alpha (EFS) promoter, the human (hCMV) or mouse (mCMV) cytomegalovirus immediate early promoter, the chicken beta actin/hCMV fusion promoter CBA, the hSynaptin promoter or the liver specific promoter LSP. In the Example shown in FIG. 16, the Cas9 5'UTR contains an intron, in this example derived from the rat preproinsulin II gene, and a nuclear localization signal. The nuclear localization signal inserted at the amino-terminus of Cas9 could be derived from the SV40 large T antigen, from nucleoplasmin or might be a synthetic NLS. The amino acid sequences of various NLSs are provided as SEQ ID NOs: 59-62. The synthetic Cas9 open reading frame, with a FLAG epitope tag, and finally a poly(A) addition site, derived from a viral or cellular gene or generated synthetically, is included.

Pharmaceutical Compositions and Methods of Treatment

The recombinant expression cassettes or constructs and recombinant vectors comprising said expression cassettes as described herein have many potential applications, such as enhanced gene deletion, treatment of cancer and use as an antiviral agent to eliminate episomal viral DNA genomes from infected tissues. One aspect of the present disclosure provides a method of treating a viral infection in a subject comprising, consisting of, or consisting essentially of administering to the subject a therapeutically effective amount of a recombinant vector as described herein. Another aspect of the present disclosure provides a method of eliminating viral episomes in a subject comprising, consisting of, or consisting essentially of administering to the subject a therapeutically effective amount of a recombinant vector as described herein. The methods may result in inhibition of viral replication or inhibition of target sequence expression after administration of the recombinant vector or constructs described herein.

The methods also encompass contacting cells with the constructs and vectors described herein. Cells may be contacted with the agent directly or indirectly in vivo, in vitro, or ex vivo. Contacting encompasses administration to a cell, tissue, mammal, patient, or human. Other suitable methods may include introducing or administering an agent to a cell, tissue, mammal, or patient using appropriate procedures and routes of administration as defined below. The recombinant vectors may be administered to the cells of said subject on an in vivo basis, i.e., the contact with the cells of the subject takes place within the body of the individual in accordance with the procedures which are most typically employed.

As used herein, "treatment" is a clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Those in need of treatment include those already affected by a disease or disorder or undesired physiological condition as well as those in which the disease or disorder or undesired physiological condition is to be prevented.

Treating cancer includes, but is not limited to, reducing the number of cancer cells or the size of a tumor in the subject, reducing progression of a cancer to a more aggressive form, reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

The term "effective amount" or "therapeutically effective amount" refers to an amount sufficient to effect beneficial or desirable biological and/or clinical results. The therapeutically effective amount will vary depending on the compound, formulation or composition, the disease and its severity and the age, weight, physical condition and responsiveness of the subject to be treated. The recombinant vectors are preferably suspended in a pharmaceutically acceptable delivery vehicle (i.e., physiologically compatible carrier), for administration to a human or non-human mammalian patient. Suitable carriers may be readily selected by one of skill in the art and may depend on the route of administration chosen.

The pharmaceutical compositions will also contain pharmaceutically acceptable components, such as excipients, carriers and/or stabilizers. Such components include any pharmaceutical agent that does not itself induce an immune response harmful to the individual receiving the composition, and which may be administered without undue toxicity. Pharmaceutically acceptable components include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. Other exemplary components include lactose, sucrose, calcium phosphate, gelatin, dextran, agar, pectin, peanut oil, sesame oil, and water. The selection of the carrier is not a limitation of the present invention. Optionally, the compositions of the present disclosure may comprise, in addition to rAAV vector and other component(s), other conventional pharmaceutical ingredients, such as preservatives, chemical stabilizers and the like. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin and albumin. A thorough discussion of pharmaceutically acceptable excipients is available in REMINGTON'S PHARMACEUTICAL SCIENCES (Mack Pub. Co., N.J. 1991).

Appropriate doses will depend, among other factors, on the specifics of the AAV vector chosen (e.g., serotype, etc,), on the route of administration, on the mammal being treated (e.g., human or non-human primate or other mammal), age, weight, sex, and general condition of the subject to be treated and the mode of administration. Thus, the appropriate dosage may vary from patient to patient. An appropriate effective amount can be readily determined by one of skill in the art.

Dosage treatment may be a single dose schedule or a multiple dose schedule. Moreover, the subject may be administered as many doses as appropriate. One of skill in the art can readily determine an appropriate number of doses.

However, the dosage may need to be adjusted to take into consideration an alternative route of administration, or balance the therapeutic benefit against any side effects. Such dosages may vary depending upon the therapeutic application for which the recombinant vector is employed.

The recombinant vector(s) are administered in sufficient amounts to enter the desired cells and to guarantee sufficient levels of functionality of the transferred nucleic acid composition to provide a therapeutic benefit without undue adverse, or with medically acceptable, physiological effects which can be determined by those skilled in the medical arts.

Optionally, in some embodiments, rAAV-mediated delivery according to the present disclosure may be combined with delivery by other viral and non-viral vectors. Such other viral vectors including, without limitation, adenoviral vectors, retroviral vectors, lentiviral vectors and herpes simplex virus (HSV) vectors may be readily selected and generated according to methods known in the art. Similarly, non-viral vectors, including, without limitation, liposomes, lipid-based vectors, polyplex vectors, molecular conjugates, polyamines and polycation vectors, may be readily selected and generated according to methods known in the art. When administered by these alternative routes, the dosage is desirable in the range described above.

To minimize total RGN size, we have optimized the Cas9 nuclease and the sgRNA expression cassettes by using small but effective promoters. Single guide RNA chimeras consist of two essential portions: a 5' portion that is completely complementary to the sequence of the target DNA sense strand and a conserved, structured 3'terminus scaffold essential for Cas9 binding. We have developed and characterized a sgRNA that fuses a portion of the *N. meningitides* and *Staphylococcus aureus* crRNA and tracrRNA, which can be expressed from a single RNA Polymerase III promoter as shown in the Examples.

This minimal sgRNA can be readily modified to target any DNA locus by altering the 5' targeting sequence, and is expressed from a minimal RNA polymerase III based cassette. The sgRNA is functional when loaded into Cas9, as demonstrated by the novel Green Fluorescent Protein (GFP) and luciferase cleavage reporter assays with Spy Cas9, Nme Cas9 and Sau Cas9 as shown in the Examples. This assay measures the expression of the HIV-1 Rev protein and an in frame target DNA fused to the coding sequence for GFP or luciferase; cleavage results in reduced or ablated Rev/GFP or Rev/Luc expression. Expression of the NmeCas9 protein together with an appropriate gRNA results in loss of GFP expression as detected by microscopy and reduced luciferase production as measured by luciferase assay light units, and loss of Rev-fusion protein expression, as detected by Western blot using an antibody specific to Rev. These assays demonstrate that we have successfully expressed adequate Cas9 and sgRNA levels in culture, and that DNA target cleavage is both highly efficient and specific.

Construction of single and dual sgRNA Cas9 AAV expression vectors will directly facilitate the efficient intracellular delivery and expression required for the efficient destruction of viral DNA episomes by antiviral RGNs in vivo. Specific serotypes of AAV have shown high levels of tropism for both hepatocytes and neurons in vivo. Moreover, AAV vectors have been shown to be safe to use in vivo, and can be produced at high titer, which is ideal for testing anti-HBV and anti-HSV-1 RGNs in the HBV-infected humanized murine liver or in latently HSV-1-infected murine trigeminal ganglia, respectively. In the context of genome engineering work with RGNs has shown that cleavage of genomic DNA results in site-specific mutagenesis, other point mutations or insertions/deletions due to imperfect repair by non-homologous end-joining. However, when the Cas9 RGNs are targeted to replicating episomes in culture we observe their elimination from cells. Suggesting targeting viruses allows removal of the episome from the cell. This episome elimination phenomenon is novel and advantageous, and both HSV-1 and HBV gRNAs can be combined to target multiple viral genes simultaneously, thus enhancing the desired inhibitory effect.

Numerous essential gene targets for both HBV and HSV have been selected as defined above. HBV reverse transcriptase, core protein, and envelope proteins S and L are essential for infectious viral particle production, and these have been successfully targeted using the Rev-GFP reporter assay in culture. In the case of HSV-1, numerous targets have also been selected in the LAT region, which is the sole transcribed region during neuronal latency, as well as in the essential ICP4 gene and ICP0 gene. AAV vectors encoding an HBV or HSV-1-specific Cas9-based payload will be directly compared with non-specific control AAV vectors, and both liver or trigeminal ganglia tissue can be evaluated for loss of HBV cccDNA or HSV-1 episomes, respectively, by quantitative PCR. Proof of concept in vivo in a humanized mouse model of HBV chronic infection or in a murine model of HSV-1 latency would require both a highly effective effector/viral target coupled with liver or trigeminal ganglion-specific transduction with AAV. Cas9/sgRNA combinations delivered by AAV represent a novel, and potentially highly effective, treatment to induce the specific and efficient elimination of viral DNA episomes, including not only HBV and HSV-1 but also HSV-2 and Human Papilloma Virus (HPV)-derived viral DNA episomes from infected tissues in vivo.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1: Design and Use of Constructs Targeting HPV

CRISPR/Cas9 Constructs and sgRNA Design

Two pairs of single guide RNAs (sgRNAs) were designed using the ZiFit web application to target DNA sequences encoding the amino terminal region of the HPV-18 E6 and E7 ORFs. RNA-guided DNA endonucleases (RGNs) were constructed by cloning HPV specific sgRNAs into the px330 vector (Addgene) expressing Spy Cas9 (Cong et al, 2013). sgRNAs were also cloned into the px458 vector, an alternative version of px330 containing a gfp marker useful for flow cytometric analysis (Ran et al., 2013). RGN function was tested by generating a vector containing either HPV-18 E6 or E7-derived viral DNA targets inserted in frame between an HIV-1 rev gene fragment encoding amino acids 1 to 59 of Rev (Malim et al., 1989) and a 3' gfp indicator gene. Following co-transfection of the reporter plasmid with a Spy Cas9/sgRNA expression construct, function was determined by detecting the specific loss of Rev and GFP expression by Western blot or flow cytometry, respectively. HPV-16-specific sgRNAs targeting the HPV-16 E6 and E7 ORFs integrated in the SiHa cell line were designed and tested using a similar approach. The following gene-specific sgRNA sequences were used and constructed as outlined previously (Cong et al., 2013): HPV-18 E6t1 (GGCGCTTTGAGGATCCAACA; SEQ ID NO: 8), HPV-18 E6t2 (GAAGCTACCTGATCTGTGCA; SEQ ID NO: 9), HPV-18 E7t1 (GGAGCAATTAAGCGACTCAG; SEQ ID NO: 10), HPV-18 E7t2 (GAAGAAAACGATGAAATAGA; SEQ ID NO: 11), HPV-16 E6t1 (GCAACAGTTACTGCGACGTG; SEQ ID NO: 12), and HPV-16 E7t1 (GCCAGCTGGACAAGCAGAAC; SEQ ID NO: 13). Bolded nucleotides indicate mismatched 5' G residues required for transcription initiation from a U6 promoter.

Cell Culture

HeLa, 293T, and SiHa cells were grown in Dulbecco's modified Eagle Medium (DMEM) supplemented with 10% fetal bovine serum (FBS), 2 mM Antibiotic-Antimycotic (Gibco Cell Culture) and 50 µg/mL gentamycin (LifeTechnologies) at 37° C.

Reporter Assays

Reporter assays in 293T cells were performed using the calcium phosphate transfection method. 293T cells were plated at ~1.25×10$^5$ cells per well in 12-well plates and transfected with a 4:1 ratio of RGN expression plasmid to indicator plasmid. 293T cells were then assayed by Western blot to detect Rev epitope tag expression and by flow cytometry to determine the positive fraction and mean fluorescence intensity (MFI) of eGFP-positive cells 3 days post transfection.

SURVEYOR Assays and Mutagenesis Spectra

HeLa cells were plated at 2.5×10$^5$ cells per well in 6-well plates and transfected using Fugene6 with a 3 to 1 ratio of RGN expression vector to pL/CMV/eGFP (pLCE) (Seedorf et al., 1987), which expresses eGFP, to determine transfection efficiency. Genomic DNA was extracted 48 hours post-transfection using a DNeasy kit (Qiagen) following the manufacturer's protocol. The genomic region surrounding the viral target sites was PCR amplified using GoTaq cocktail (Promega, #9PIM300) and then purified. PCR products were then denatured and reannealed to enable DNA heteroduplex formation: 95° C. for 10 min, 95° C. to 85° C. ramping at −1° C./sec, 85° C. to 25° C. at −0.25° C./sec, and 25° C. hold for 1 minute. After reannealing, products were treated with SURVEYOR nuclease and SURVEYOR enhancer S (Transgenomics) following the manufacturer's protocol, and analyzed on a 2% agarose gel. To determine the sequence spectra of the mutations introduced by HPV-18 E6- and E7-specific sgRNAs, we designed primers with unique restriction enzyme sites that bound sequences flanking the predicted RGN cleavage locations. The mutagenized HeLa genomic DNA was PCR amplified at 48 hours after transfection, cloned, sequenced, and aligned to the HeLa genome.

Western Blots and pRB Quantification

Phenotypic analysis of RGNs in HeLa was performed using the Fugene6 transfection reagent as per the manufacturer's protocol. Cells were plated at 2.5×10$^5$ cells per well in 6-well plates and transfected with a 3 to 1 ratio of RGN expression vector to pLCE (a GFP-expressing plasmid included to determine transfection efficiency). SiHa cells were transfected with HPV-16-specific RGN expression vectors using Lipofectamine3000 (Clontech) using the manufacturer's protocol. Cells were then harvested and lysed in SDS/β-mercaptoethanol protein lysis buffer 48 hours post transfection. Lysates were subjected to electrophoresis on 4-20% SDS-polyacrylamide gels (Bio-Rad) and transferred to nitrocellulose membranes. The membranes were then probed in 5% milk-PBS-T (PBS, 0.1% Tween 20, 0.5% bovine serum albumin) with the following antibodies: anti-Flag (Sigma F1804), a rabbit Rev polyclonal antiserum (Malim et al., 1989), anti-β-actin (Santa Cruz S.C.-47778), anti-p53 (Santa Cruz S.C.-126), anti-p21 (Santa Cruz S.C.-397), and anti-Rb (BD Pharmigen 554136). The membranes were washed in PBS-T, incubated with a species-specific secondary antibody, and then washed again in PBS-T. The membranes were incubated with Western Bright Sirius Western blot detection kit (Advansta) and signals captured using GeneSnap and quantified using GeneTools (Syngene). In order to determine the specificity of RGN cleavage, we generated a pcDNA3 construct expressing an E6 mutant harboring synonymous mutations in the Cas9 "seed" region. These experiments were conducted by transfecting HeLa cells in 6-well plates at 30-40% confluency with a 3 to 1 ratio of an RGN expression vector to mutant E6 expression plasmid with Fugene6. Western blots were conducted in triplicate at 48 hours post-transfection.

Growth Inhibition and Cell Cycle Analysis

To determine growth effects of RGNs, HeLa cells were plated in 12-well plates at 10$^5$ cells per well and transfected with 750 ng of an HPV-18-specific RGN expression vector in triplicate. Flow cytometric analysis measuring the percentage of eGFP-positive cells using the FACS Canto software was performed 48, 72, and 96 hours post-transfection. Data were normalized to a px458 transfected culture. To examine cell cycle progression, 10$^6$ HeLa cells were plated in 6-cm plates and co-transfected with HPV-18 E6- or E7-specific RGN expression vectors and an eGFP expression plasmid, at a 3 to 1 ratio, using Fugene6. Exponentially growing cells were treated 48 hours post-transfection with 10 µg/mL 5-bromodeoxyuridine (BrdU; Calbiochem) for 1 hour. Cells were then trypsinized, washed with PBS, and fixed with 2% paraformaldehyde for 1 hour at 25° C. Cells were washed with PBS and permeabilized with 70% ethanol overnight at 4° C. After washing with PBS, DNA was denatured by treating the cells with 2 M HCl for 30 minutes at 25° C. and then washed twice with PBS-T. Cells were resuspended in 100 µL PBS-T and 2.5 µL Alexa Fluor 647 anti-BrdU antibody (catalog no. 560209; BD Biosciences) for 20 minutes at 25° C. Cells were washed once with PBS and resuspended in 200 µL propidium iodide (PI)/RNase staining buffer (BD Biosciences). Cells were then analyzed by flow cytometry using a BD FACSCanto II and FlowJo software. Separate flow plots comparing BrdU and PI staining were generated to compare transfected (GFP-positive) and non-transfected (GFP-negative) HeLa cells.

Cell Survival Assay

To measure HeLa cell transduction efficiency, we employed the lentiviral LCE eGFP expression vector (Zhang et al., 2009). This allowed us to determine that 89.3% of the HeLa cells in culture were transduced, consistent with an initial MOI of ~2.2. The Spy Cas9/sgRNA-expressing lentiviral vectors used were based on lentiCRISPR (Shalem et al., 2014), with the appropriate sgRNAs inserted 3' to a U6 promoter. HeLa cells ($5 \times 10^4$) were transduced with these lentivectors, and fresh medium added 24 hours after infection. The cells were then cultivated for 10 days and cell numbers quantified at two day intervals.

In a second experiment, HeLa cells were again transduced with lentiCRISPR-based vectors expressing Spy Cas9 and a non-specific sgRNA, E6 sgRNA1 or E7 sgRNA1, or with LCE. In this second experiment, we used a higher predicted MOI of ~37, which should result in the infection of essentially every cell. After cultivation for 10 days, the cells were stained with 3-(4,5-dimethylthiazol-2-yl)-2,5-diphenyltetrazolium bromide (MTT). MTT was eluted from cells with isopropanol containing 0.04 M HCl and the absorbance was determined by Fluostar Omega (BMG Labtech) at 590 nm with a reference filter of 620 nm. Survival was calculated relative to mock infected cells.

Results

Figure 1B:
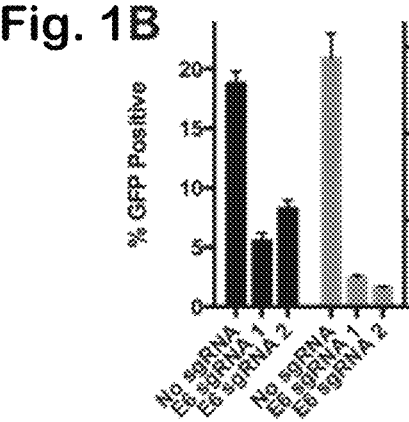
FIG. 1B is a graph showing eGFP expression data from 293T cells co-transfected with plasmids expressing the FLAG-tagged Spy Cas9 protein and sgRNAs specific for the HPV-18 E6 gene, or a control construct, and their cognate indicator plasmids. Transfected cells were processed for flow cytometry at 72 hours. The number of GFP– positive cells and the mean fluorescence intensity (MFI) of these cells is indicated. Average of three independent experiments with SD indicated.
Figure 1C:
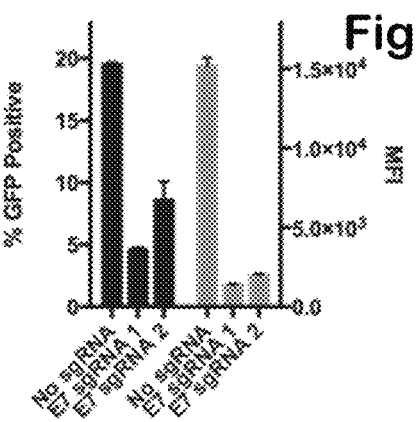
FIG. 1C is similar to panel B but using two HPV-18 E7-specific sgRNAs.
Figure 1D:
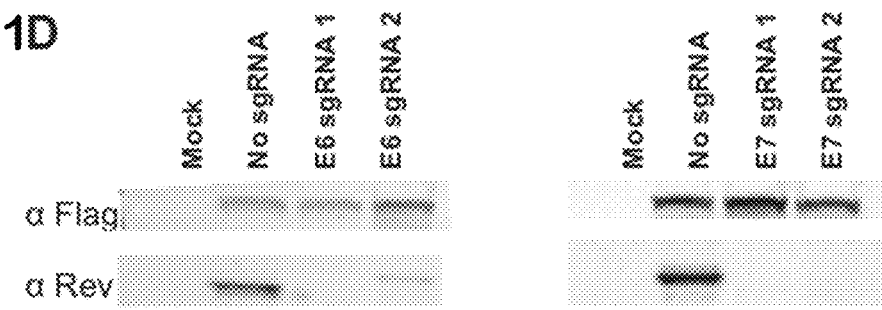
FIG. 1D depicts a Western blot using an HIV-1 Rev specific antiserum to detect expression of the Rev-GFP indicator fusion protein, thus demonstrating sgRNA efficacy and specificity.

To target the integrated genomic copies of HPV-18 present in HeLa cells for DNA cleavage, we designed sgRNAs complementary to nucleotides 5 to 24 and 36 to 55 of the HPV-18 E6 open reading frame (ORF) and nucleotides 84 to 103 and 106 to 125 of the HPV-18 E7 ORF. These were expressed under the control of a U6 RNA polymerase III promoter present in the px330 expression vector, which also expresses the Spy Cas9 protein (Cong et al., 2013). To assess the functionality of these sgRNAs, we cloned cognate HPV-18 E6- or E7-derived target sequences in frame between an amino-terminal region encoding the first 59 amino acids of the HIV-1 Rev protein (Malim et al., 1989) and a carboxy-terminal gfp indicator gene (FIG. 1A). If an sgRNA is indeed functional, then it should inhibit the expression of the predicted Rev-target-GFP fusion protein as determined either by GFP fluorescence or Western blot analysis using a Rev-specific polyclonal antiserum. Indeed, as shown in FIG. 1B, both E6-specific sgRNAs greatly reduced both the number of GFP-positive cells, when the RGN expression vector was co-transfected into 293T cells along with the indicator vector, as well as the average mean fluorescence intensity (MFI) of the remaining GFP-positive cells. Similarly, both E7-specific sgRNAs dramatically inhibited GFP expression from their cognate indicator plasmids in co-transfected cells (FIG. 1C). Furthermore, analysis of Rev-target-GFP fusion protein expression in these same co-transfected 293T cells by Western blot (FIG. 1D) revealed an almost total loss of indicator protein expression. We therefore concluded that all four HPV-18 E6- or E7-specific sgRNAs can effectively silence the expression of a cognate target gene.

We next asked if we could inactivate the endogenous HPV-18 E6 and E7 genes integrated into the HeLa cell genome. As all four sgRNAs appeared to function equivalently, we focused our subsequent research on E6 sgRNA1 and E7 sgRNA1. To confirm these sgRNAs were indeed inducing the expected DNA cleavage, we used the SURVEYOR assay to determine if we could detect RGN-induced indels at the predicted Cas9 cleavage site. For this purpose, we transfected HeLa cells with a px330-based vector encoding Spy Cas9 (Cong et al., 2013) and an E6- or E7-specific sgRNA. At 48 hours post-transfection, we isolated the HeLa genomic DNA and PCR-amplified the regions of the HPV-18 genome containing either the E6 or E7 target site for Cas9. The resultant PCR fragment was then isolated, denatured and then re-annealed to produce a population of DNA heteroduplexes that were digested using SURVEYOR nuclease, which is predicted to cleave at any sites of Cas9-induced mutagenesis. As shown in FIG. 2, we indeed readily detected the presence of indels in both the HPV-18 E6 and E7 gene at the predicted Cas9 target site. To further characterize these mutations, we cloned the same PCR fragments derived from the HPV-18 E6 or E7 gene and then performed DNA sequencing across the predicted cleavage site located 3 bp 5' to the Cas9 PAM sequence (Mali et al., 2013). Analysis of the HPV-18 E6 gene gave 234 DNA sequence reads, of which 19 bore an assortment of different deletion mutations while 34 contained the same insertion mutation of a single "A" residue 3 bp 5' to the Spy Cas9 PAM motif. The remaining 181 samples analyzed contained the wildtype E6 sequence. Similarly, in the case of the HPV-18 E7 gene, we recovered 232 DNA sequences of which 6 represent deletion mutations adjacent to the predicted Spy Cas9 cleavage site while 46 represent insertions of 1 or 2 bp, again at a site 3 bp 5' to the PAM motif, with by far the most common being a single "T" nucleotide insertion. Interestingly, we also recovered one sequence containing a large insertion mutation that introduced a sequence derived from human chromosome 8. Therefore, for both the HPV-18 E6 and E7 gene, we were able to recover multiple mutations at the predicted E6 or E7 RGN cleavage site, almost all of which are predicted to disrupt the E6 or E7 ORF.

Both E6 and E7 expression are known to be required for HeLa cell growth and survival (Howley, 1990; DeFilippis et al., 2003; Goodwin and DiMaio, 2000), and we therefore next asked if targeting E6 and E7 with an RGN would indeed inactivate E6 and E7 function. As noted above, the HPV E6 protein functions to repress the expression of the host p53 tumor suppressor so that loss of E6 function is expected to result in the activation of not only p53 expression but also of downstream effectors of p53, including the cyclin-dependent kinase inhibitor p21 (Goodwin and DiMaio, 2000; Mighty and Laimis, 2014; McLaughlin-Drubin and Munger 2014; and Scheffner et al., 1990). As shown in FIG. 3A, we indeed observed the specific induction of both p53 and p21 expression in cells expressing the E6 sgRNA but not in control cells or in cells expressing the E7 sgRNA.

The HPV-18 E7 protein functions to repress the function of the host cell retinoblastoma (Rb) protein by binding to the hypophosphorylated form of Rb, thereby inducing Rb degradation and preventing the formation of Rb/E2F complexes that would block cell cycle progression (Mighty and Laimis, 2014; McLaughlin-Drubin and Munger 2014; Howley, 1991; DeFilippis et al., 2003). As shown in FIG. 3B, we did detect an increase in Rb expression that was, however, fairly modest ($1.4 \pm 0.03$-fold) when normalized to the β-actin internal control. We note, however, that disruption of E7 expression results in cell cycle arrest so that cells bearing a disrupted E7 gene are expected to be selectively lost from the transfected culture. Indeed, we observed that expression of the Flag-tagged Spy Cas9 protein was specifically reduced in cells expressing an sgRNA specific for either E6 or E7 (FIG. 3B). If this decrease is taken into account, then the increase in Rb expression is a more substantial 5.54±1.42-fold over the control, which is statistically significant (p=0.011).

It could be argued that the activation of p53 in HeLa cells expressing Spy Cas9 and the E6-specific sgRNA1 is a non-specific effect resulting from an off-target effect, such as promiscuous DNA damage. However, analysis of potential target sites in the human genome for E6 sgRNA1, by BLAST search of the NCBI human genome database, failed to identify any targets with perfect complementarity to the 13-nt E6 sgRNA1 seed sequence in combination with the Spy Cas9 PAM 5'-NGG-3'. We did identify a single perfect human genome target site for E7 sgRNA1 in a locus of the human genome, designated-164032096, located on chromosome 2 that is not believed to be transcribed. In addition, we detected a number of potential target sites for E6 sgRNA1 and E7 sgRNA1 that differed from a perfect target site at a single base pair and therefore might also represent potential off-target cleavage sites in the human genome.

Off-target genomic DNA damage would be predicted to activate p53 and we were particularly interested in demonstrating that the activation of p53 by E6 sgRNA1 resulted exclusively from cleavage of the HPV E6 gene. We therefore generated a mutant form of the HPV-18 E6 gene in which we introduced mutations that would be predicted to block sgRNA cleavage but that did not alter the underlying E6 amino acid sequence (FIG. 3C). As shown in FIG. 3D, co-transfection of an expression vector encoding this variant form of E6 entirely blocked the activation of p53 expression by the E6-specific RGN, which strongly suggests that p53 induction in the presence of E6 sgRNA1 indeed reflects the selective loss of E6 expression.

Figure 4A:
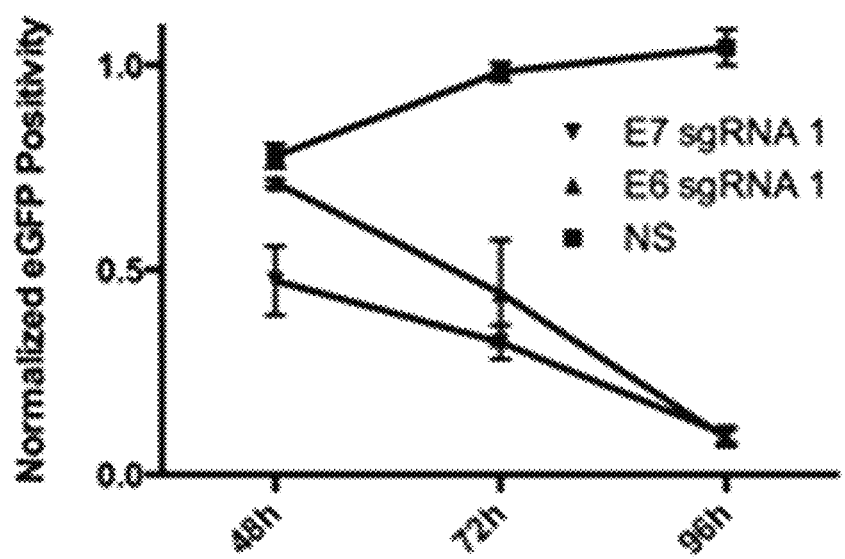
FIG. 4A shows that Spy Cas9-mediated disruption of either the HPV-18 E6 or E7 gene results in the expected inhibition of HeLa cell growth. The number of GFP+ cells transfected with vectors encoding Spy Cas9, a control or HPV-specific sgRNA and the gfp gene is shown.
Figure 4B:
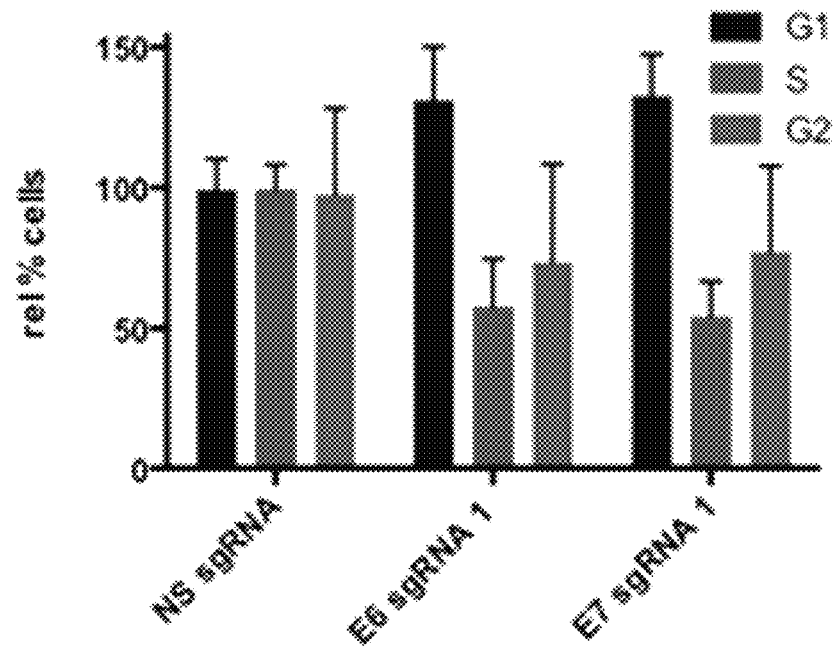
FIG. 4B shows the cell cycle analysis of HeLa cells expressing E6 or E7 specific RGNs using BrdU incorporation and propidium iodide (PI) staining followed by FACS analysis. Results from four separate biological replicates of the transfected eGFP-positive HeLa cell population are shown.
Figure 4C:
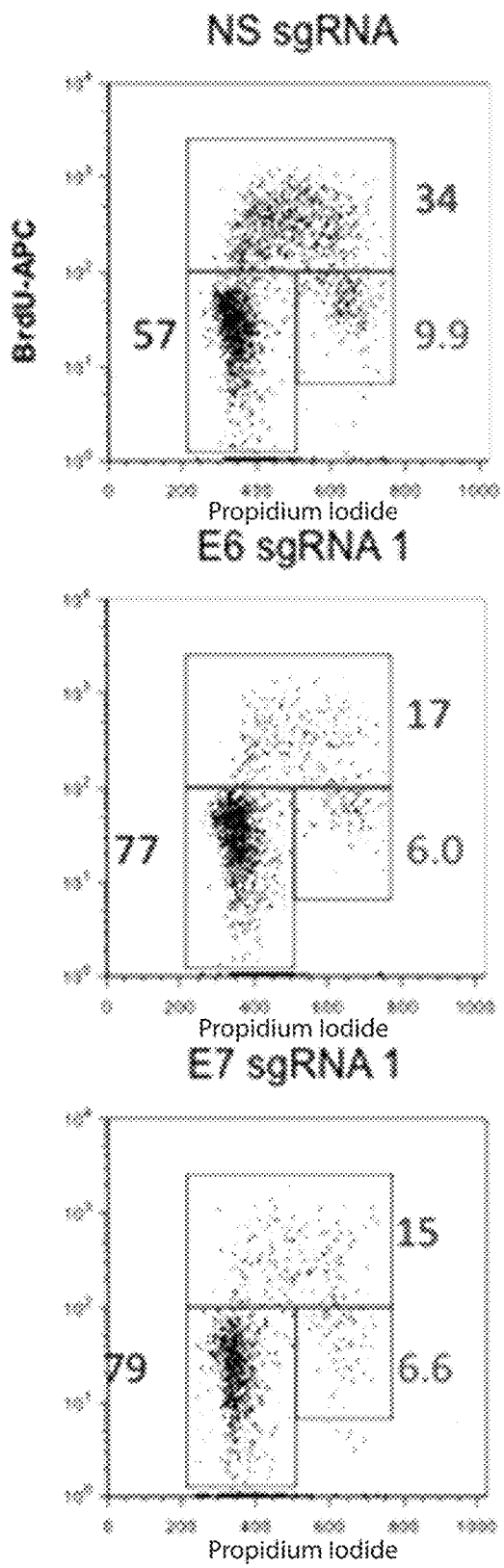
FIG. 4C shows representative flow cytometery plots for the sgRNAs indicated. The percentage of GFP-positive HeLa cells in each phase of the cell cycle was quantitated and is indicated. NS, non-specific.

Previous work has shown that loss of either E6 or E7 function in HeLa cells, and in other HPV-transformed cells, results in senescence, cell cycle arrest and, in the case of E6 repression, also apoptosis (Mighty and Laimins, 2014; McLaughlin-Durbin and Munger, 2009; DeFilippis et al., 2003). To test whether RGNs specific for E6 or E7 would exert the predicted phenotypic effect, we analyzed the growth in culture of cells expressing Spy Cas9 and either the E6 sgRNA1 or E7 sgRNA1 when compared to a control sgRNA. As shown in FIG. 4A, while the control cells continued to replicate, HeLa cells expressing the E6- or E7-specific sgRNA strongly decreased in number over time. We next analyzed the cell cycle progression of control cells relative to E6 sgRNA1 or E7 sgRNAs-expressing cells by culturing the cells in the presence of BrdU, which is incorporated into newly synthesized DNA, and then staining the cells with propidium iodide (PI), which allows measurement of the total DNA level per cell. As shown by flow cytometry in FIG. 4C, the control culture showed 57% of cells in G1, 34% In S phase and 9.9% in G2. In contrast, the culture expressing E6 sgRNA1 were 77% in G1, 17% in S phase and 6.0% in G2, while cells expressing E7 sgRNA1 were 79% in G1, 15% in S phase and 6.6% in G2. A bar graph summarizing data derived from four separate BrdU/PI labeling experiments, shown in FIG. 4B, confirms that both the E6- and E7-specific sgRNAs induce cell cycle arrest in G1 while strongly reducing the number of cells in S phase or entering G2, as expected for inhibitors of E6 or E7 expression.

Figure 5A:
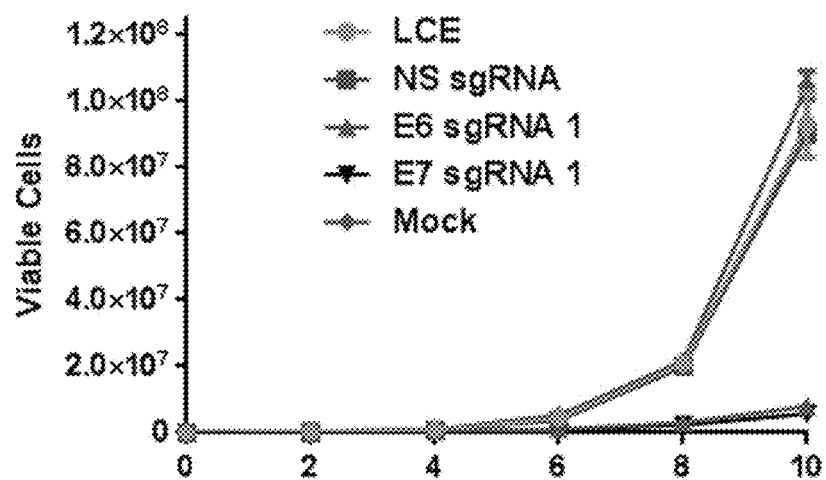
In FIG. 5A, the HeLa cells were transduced with a lentiviral vector multiplicity of infection (MOI) of ~2.2, resulting in transduction of ~90% of the cells in culture. Cell growth was then monitored over a 10-day period.

As noted above, repression of E6 or E7 expression in cervical carcinoma cells is predicted to not only induce cell cycle arrest, as reproduced here in FIG. 4, but also senescence and/or apoptosis. Therefore, it is expected that the expression of Cas9/sgRNA combinations specific for E6 or E7 would initially inhibit cell growth followed by induction of cell death. To validate this prediction, we transduced HeLa cells with lentiviral vectors encoding Cas9 and either a control, E6- or E7-specific sgRNA, with a similar lentiviral vector encoding GFP, or mock transduced the cells. Using fluorescence activated cell sorting, we observed that 89.3% of the cells transduced with the GFP-expressing lentivirus were GFP+, consistent with an initial MOI of ~2.2. We then counted the cells in culture at two day intervals for 10 days (FIG. 5A). The cultures transduced with Cas9/sgRNA combinations specific for HPV-18 for E6 or E7 had ~10-fold fewer cells than the control cells at all time points, thus suggesting that the growing cells likely derive from ~10% of the initial culture that was not transduced.

Figure 5B:
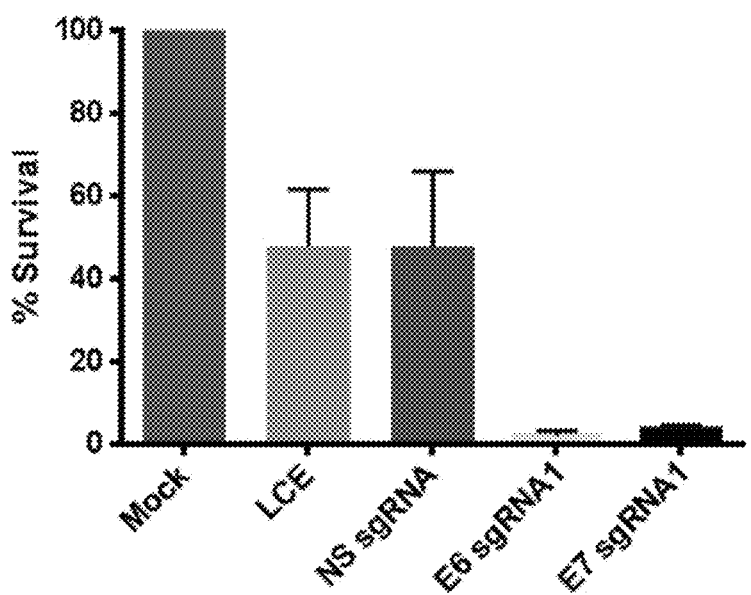
In FIG. 5B, the HeLa cells were transduced with a lentiviral vector MOI of ~37, predicted to transduce >99% of the cells in culture. The cells were then assayed for viability by MTT staining at day 10. N.S., non-specific.

To ask if expression of Cas9/sgRNA combinations specific for HPV-18 E6 or E7 would indeed induce HeLa cell death, we repeated the above transduction experiment using a higher titer of lentiviral vector (MOI of ~37) that is predicted to transduce almost every HeLa cell in the culture. After 10 days in culture, the cells were stained with MTT and the percentage of viable cells determined (FIG. 5B). Surprisingly, in this experiment, the control lentiviral vectors resulted in an ~2-fold decrease in cell viability that was clearly not due to Spy Cas9 expression, as the same effect was observed with the GFP-expressing lentiviral vector. In contrast, both the E6- and E7-specific sgRNAs, in the presence of Spy Cas9, induced the almost complete demise of the transduced HeLa cell culture. Therefore, targeted disruption of HPV E6 or E7 has the potential to induce the specific elimination of HPV-transformed cells.

Figure 6A:
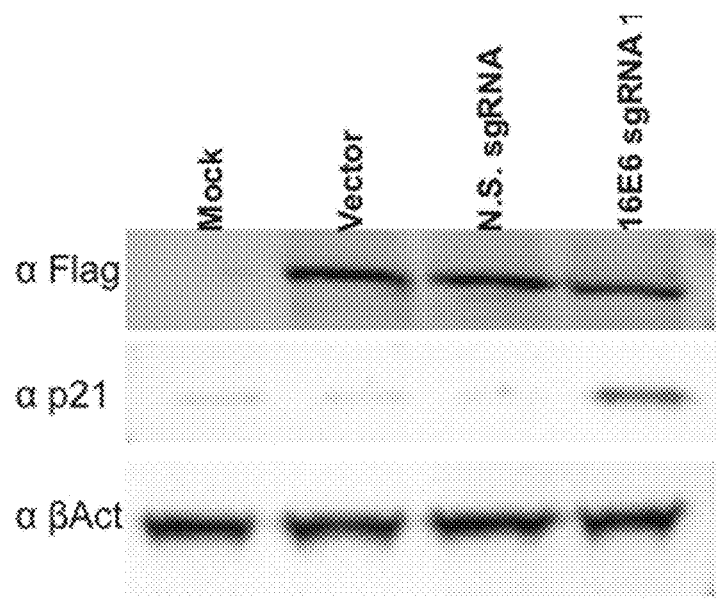
In FIG. 6A, the lysate was probed for the Flag-tagged Cas9 protein, the p53 effector protein p21 and endogenous β-actin.
Figure 6B:
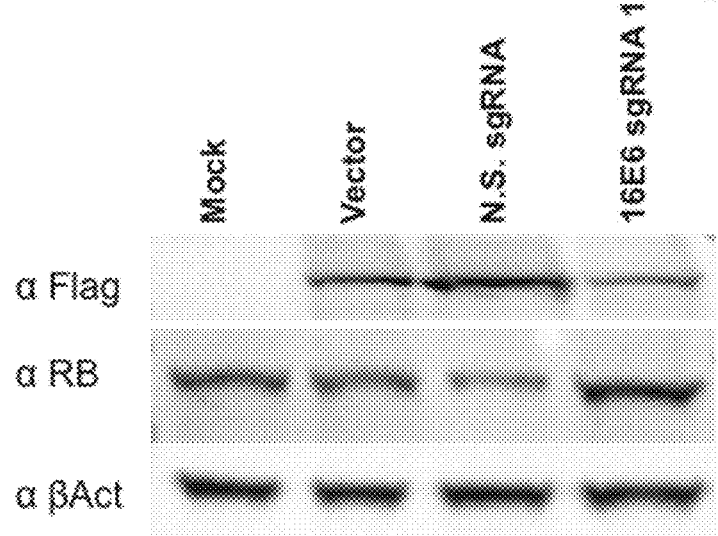
FIG. 6B is similar but was probed for Rb expression. The N.S. (non-specific) sgRNA used as a control in this figure is E6 sgRNA1, which is specific for the HPV-18 E6 gene but is not predicted to recognize the HPV-16 E6 gene.

All the work described thus far used the HPV-18 transformed cervical carcinoma cell line HeLa. To extend these studies, we also analyzed the human SiHa cervical carcinoma cell line, which is transformed by HPV-16 (Seedorf et al., 1987), using sgRNAs specific for HPV-16 E6 and E7, which differ in sequence from HPV-18 E6 and E7. In this experiment, we therefore used E6 sgRNA1, which is specific for HPV-18 E6, as our "non-specific" sgRNA. Targeting of the HPV-16 gene in SiHa cells using the Spy Cas9 protein and an HPV-16 E6-specific sgRNA resulted, as expected, in the specific induction of the p53 effector protein p21 (FIG. 6A), as also seen in HeLa cells after targeting of E6 (FIG. 3A). However, the HPV-18-specific E6 sgRNA1 failed to induce p21 expression, thus further confirming that activation is due to E6 cleavage and not due to off-target DNA cleavage. Similarly, targeting of the HPV-16 E7 gene in SiHa cells resulted in a modest but significant enhancement in the expression of the cell Rb protein (FIG. 6B), as also seen in HeLa cells (FIG. 3B). Therefore, RGNs targeted to either E6 or E7 are able to trigger the p53 or Rb pathway, respectively, in not only HPV-18 but also HPV-16-transformed cervical carcinoma cells.

Example 2: Development and Use of HBV Specific CRISPR/Cas9

Single Guide RNA Design and Lentiviral Vector Production

Figure 7A:
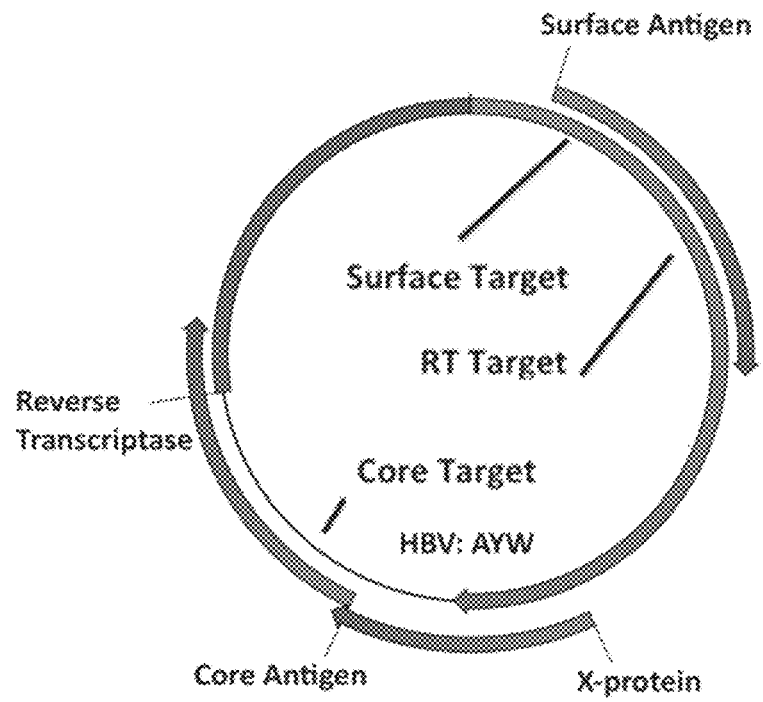
FIG. 7 is a set of figures showing the HBV targeting strategy and sgRNA optimization. To target HBV DNA intermediates in infected cells, we designed sgRNAs specific for the HBV surface antigen (Ag), core, and reverse transcriptase (RT) ORFs, as depicted in FIG. 7A. To assess efficacy, fusion protein-based indicator plasmids, which encode an amino-terminal HIV-1 Rev-derived epitope tag, an in-frame HBV-derived target, and a carboxy-terminal FLuc indicator gene, were employed similar to FIG. 1A above.
As shown in FIG. 7B, all three sgRNA candidates effectively inhibited FLuc expression from their cognate reporter plasmid in co-transfected 293T cells when compared to a control, non-specific (N.S.) sgRNA.
In FIG. 7C, expression of the same fusion protein was probed by Western blot using an α-Rev rabbit polyclonal antiserum. Co-expression of Cas9 was confirmed using an antibody specific for the FLAG epitope tag present on this protein. When the reporter was cognate for the sgRNA, a marked reduction of the expression level of the fusion protein target could be observed, confirming the specificity and efficacy of each sgRNA tested.

Multiple sgRNAs for each HBV DNA target were screened using a dual luciferase indicator assay, essentially as described above. Briefly, Spy Cas9/sgRNA coexpression constructs based upon pX330 (Cong et al., 2013) were co-transfected into 293T cells at an 8:1 ratio relative to an indicator plasmid expressing a fusion protein consisting of an amino-terminal HIV-1 Rev derived epitope tag, a central target region derived from an HBV open reading frame and lastly a carboxy-terminal firefly luciferase (FLuc) indicator gene. A *Renilla* luciferase (RLuc) expression plasmid was also co-transfected as an internal control. Transfections were analyzed at 72 h post-transfection by Promega dual luciferase assay and Western blot for the expression of the encoded Rev-target-Fluc fusion protein to confirm the specific knockdown of the DNA target. The HBV DNA targets for the sgRNAs are depicted in FIG. 7A. These candidate sgRNAs were shuttled into the LentiCRISPR lentiviral expression vector (Shalem et al., 2014), which was produced at high titer in 293T cells by co-transfection, as previously described.

HBV strain AYW targets for the sgRNAs used in this work were as follows: HBV RT (GTTCAGTTATATGGATGATG; SEQ ID NO: 1), HBV surface antigen (Ag) (GCCTGTCCTCCAACTTGTCC; SEQ ID NO: 2), HBV core protein (GTACCGCCTCAGCTCTGTAT; SEQ ID NO: 3), and non-specific control (N.S.) (GAAATCCTGCAGAAAGACCT; SEQ ID NO: 68). The initial G required for efficient RNA polymerase III transcription from the U6 promoter is underlined and is not complementary to the DNA target.

To assess the mutagenic spectrum generated by Spy Cas9/sgRNA cleavage, primers bearing unique restriction sites were designed to anneal to HBV sequences flanking the predicted Cas9 cleavage site in the RT gene. Total HBV genomic DNA was extracted from HepAD38 cells following transduction with the Cas9/sgRNA combination specific for the HBV RT gene described above, PCR amplified, cloned into pcDNA3 (Invitrogen), and Sanger sequenced. The recovered sequences were then aligned to the wild-type HBV strain AYW genome.

Cell Culture

The human 293T cells employed in the reporter assays and for lentiviral vector production were cultured in Dulbecco's modified Eagle medium (DMEM) including 10% fetal bovine serum (FBS) and antibiotics. The HepAD38 cell line regulates HBV replication through the presence or absence of Tet in the culture medium (King and Ladner, 2000; Ladner et al., 1997). Upon removal of Tet from the medium, HBV replicates and is secreted from these cells, while Tet addition completely represses HBV replication. HepAD38 cells were cultured in DMEM/F12 medium (Life Technologies) supplemented with 10% heat-inactivated FBS, 100 IU/ml penicillin, 100 µg/ml streptomycin, 100 µg/mlkanamycin, 400 µg/ml G418, and with 0.3 µg/ml Tet (for inhibition of HBV replication) or without any Tet (for induction of HBV replication). HBV 2.2.15 cells (Sells et al., 1987) were cultured in DMEM containing 10% FBS, 100 IU/ml penicillin, 100 µg/ml streptomycin, and 2 mM L-glutamine Lentiviral Transduction of Cells HepAD38 or HBV2.2.15 cells were transduced with lentiviral vectors expressing a puromycin resistance gene as well as Spy Cas9 and an sgRNA, as described above, at 85-90% confluency after growth in medium lacking Tet for 48 h, to ensure expression of HBV mRNAs and DNA. Beginning at 48 h post-transduction, cells were selected in 4 µg/ml puromycin (Life Technologies) for 10 days to eliminate any non-transduced cells. Supernatant media and cells were then harvested for ELISA and real-time PCR assays. Control cells including non-transduced HepAD38 cells were included as positive controls for HBV replication (in medium lacking Tet) or virtual absence of HBV replication (in medium containing Tet). Non-transduced HBV 2.2.15 cells were included as a control in experiments where relevant.

Quantification of HBV DNA and cccDNA in HepAD38 Cells

For HBV DNA quantification in HepAD38 cells, a set of primers for the HBV pre-S gene region was assessed according to a published real-time PCR protocol (Pas et al., 2000), which yielded an 89-bp product. For HBV cccDNA amplification, we used TaqMan primers previously shown (Chen et al., 2004) to specifically amplify cccDNA using an AB7900 HT sequence detection system (Applied Biosystems) or the Light Cycler 480 instrument (Roche). Closely similar data (not shown) were also obtained using a second set of previously described, HBV cccDNA-specific primers (Malmstrom et al., 2012)

Nuclear Extraction for cccDNA Analysis

Trypsinized HepAD38 cells were collected by centrifugation, washed with PBS and the supernatant medium discarded. We then added 500 µl of hypotonic buffer (10 mM HEPES, 10 mM NaCl, 1.5 mM $MgCl_2$, 0.5 mM DTT) to the cell pellets, along with zirconium oxide beads (ZROB05, Next Advance), and the cytoplasmic membranes were disrupted using a Bullet Blender (Next Advance), set at speed "4", for 15 sec. Nuclear pellets were then collected by centrifugation at 2500 rpm for 5 min at 4° C. and total nuclear DNA extracted following the protocol in the DNeasy Blood & Tissue Kit (Qiagen).

Antiviral Activity in HBV-CRISPR and HepAD38 Systems

Four compounds were tested against the HepAD38 cells, including lamivudine (3TC), tenofovir disoproxil fumarate (TDF), entecavir (ETV), and the nucleocapsid assembly inhibitor heteroaryldihydropyrimidine (HAP-12). All the antivirals were synthesized in our laboratories. HepAD38 cells were seeded at 50,000 cells/well in collagen-coated 96-well plates. Test compounds were added to cells to a final concentration ranging from 0.001 to 10 µM.

Real-Time PCR for HBV DNA Species in HepAD38

On day 7, total DNA was purified from supernatant using a commercially available kit (DNeasy Blood & Tissue kit, Qiagen). The HBV DNA was amplified in a real-time PCR assay using the AB 7900HT sequence detection system (Applied Biosystems) or the LightCycler 480 (Roche) as described by Stuyver et al. (2002). All samples were tested in duplicate. The concentration of compound that inhibited HBV DNA replication by 50% ($EC_{50}$) or 90% ($EC_{90}$) was determined by linear regression. HBV log viral reduction was also determined.

Cytotoxicity

HepAD38 cell viability was checked at late time points by Real-Time PCR for mitochondrial DNA [cytochrome c oxidase subunit II (COXII)] and nuclear DNA (ribosomal DNA). The mitochondrial DNA (MtDNA) and nuclear DNA (ribosomal DNA, Applied Biosystems) were amplified in parallel in a real-time PCR assay, and the amount of target mtDNA was normalized to the amount of an endogenous control and was then calculated relative to the untreated control. No evidence of cytotoxicity was observed.

Results

Figure 7B:
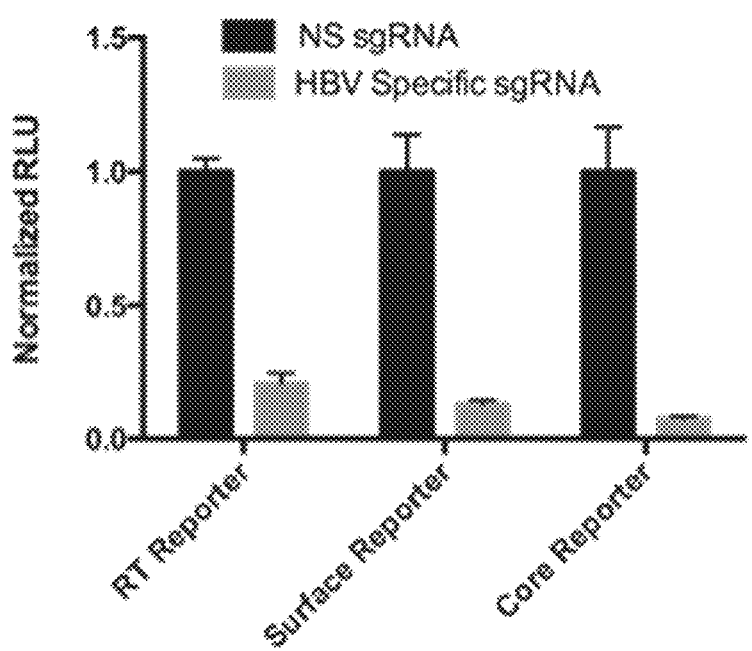
Figure 7C:
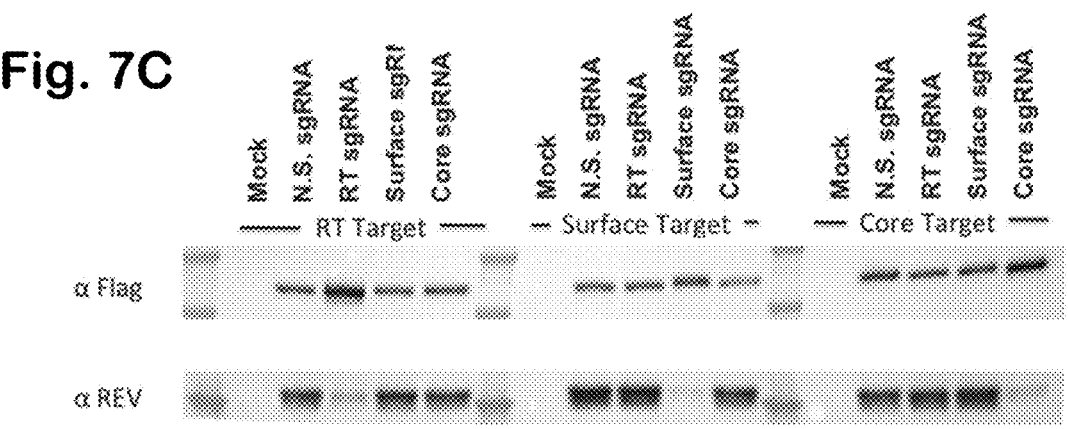

To target the HBV genome (subtype AYW) for elimination in cell culture, we first designed three sgRNAs specific for Spy Cas9 targeting the viral open reading frames (ORFs) encoding HBV surface Ag, core, and/or RT. For the HBV structural proteins surface Ag and core, N-terminal targets were selected to induce frame-shift mutagenesis. The surface Ag specific sgRNA was also predicted to cleave the RT gene (FIG. 7A). RT was also targeted in the highly conserved "YMDD" motif required for enzyme catalysis (FIG. 7A) using an sgRNA predicted to also cleave near the end of the surface Ag ORF. To verify effective sgRNA function, we employed the indicator assay described above based on co-transfection of Spy Cas9 and sgRNA expression plasmids, along with a cognate indicator plasmid, into human 293T cells. This assay quantitatively measures sgRNA efficacy by monitoring the firefly luciferase (FLuc) activity or steady state expression level of an HIV-1 Rev-sgRNA target-FLuc fusion protein; high cleavage activity results in a substantial knockdown of both. As shown in FIGS. 7B and 7C, all three sgRNAs induced an effective and specific knockdown of Fluc expression, as measured by dual luciferase assay, and Rev fusion protein expression, as measured by Western blot analysis, respectively. To directly test these three sgRNA constructs in relevant HBV cell-culture models, we next shuttled them into a lentiviral Cas9/sgRNA expression vector (Shalem et al., 2014) capable of efficient transduction of the cell lines HepAD38 and HepaRG.

Suppression of HBV Replication by Cas9/sgRNA Combinations Specific for the HBV RT, Surface Ag and Core Genes.

Figure 8A:
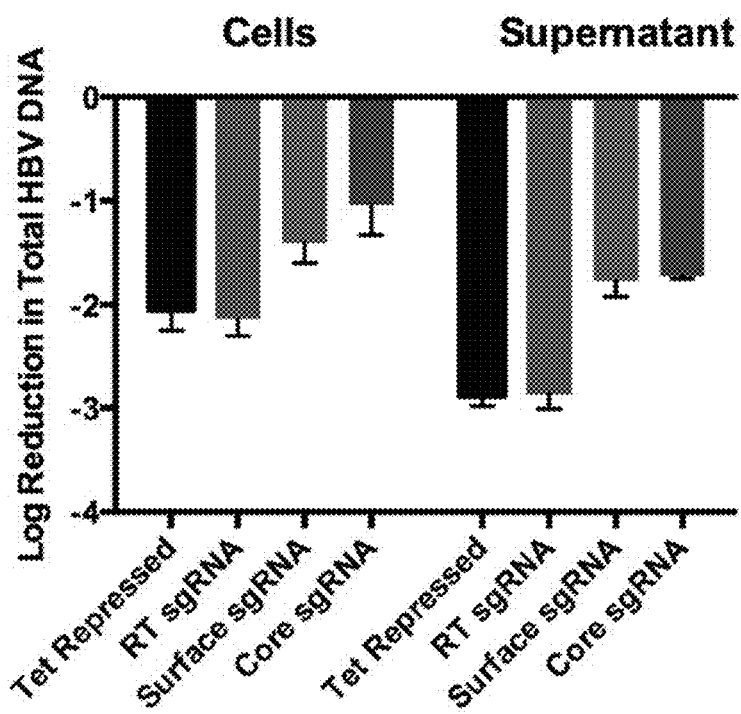
FIG. 8 shows suppression of HBV replication by HBV-specific Cas9/sgRNA combinations. HBV replication was first induced in the HepAD38 cells by culture in the absence of tetracycline (Tet) for 48 hrs. Then, the cells were transduced with lentiviral vectors encoding Spy Cas9/sgRNA combinations specific for the HBV RT, surface Ag or core ORFs, puromycin selected, and cultured in the continued absence of Tet. HepAD38 cells were also maintained in Tet+ media as a negative control. The HepAD38 cells and supernatant media were harvested and total HBV DNA (FIG. 8A) and intracellular HBV DNA or cccDNA (FIG. 8B) quantified by qPCR after 10 or 14 days in culture, respectively. (+) indicates the sample was below the detection limit (>45 cycles). All results of qPCR assays were normalized to the N.S. sgRNA control cell line. Levels of HBsAg (FIG. 8C) and HBeAg (FIG. 8D) secreted into the culture media were measured by ELISA after 10 days in culture. Data are displayed as the mean±SD of replicates. Statistical analyses were performed using Student's t-test for comparison between two groups using JMP pro 10 software. A value of P<0.05 (*) was considered statistically significant. (***) represents P<0.001.

In the HepAD38 cell line, transcription initiation of an integrated HBV linear DNA genome is tightly regulated by a Tet repressed promoter (Ladner et al., 1997). In the absence of Tet in the culture medium, the system mimics HBV replication by transcribing HBV mRNAs and pre-genomic RNA, leading to the initiation of a robust HBV replication cycle, including the synthesis of substantial levels of HBV cccDNA, and the release of DNA-containing viral particles into the supernatant medium. Consequently, this cell line represents an excellent model to test suppression of HBV replication and cccDNA synthesis by Spy Cas9 loaded with sgRNAs specific for HBV DNA targets. Therefore, we tested the ability of this system to suppress HBV replication by transducing HepAD38 cells with lentiviral vectors encoding HBV-specific Cas9/sgRNA combinations. HBV transcription was activated 48 h prior to transduction by removal of Tet from the medium to ensure that an active HBV replication cycle was in progress prior to Cas9/sgRNA expression. Subsequently, Tet was added back to the medium again, repressing the chromosomal HBV locus, to ensure that cccDNA was the primary source of viral transcription. The lentiviral vectors used also encode a puromycin resistance gene (Shalem et al., 2014), thus permitting selection of the transduced cells. As a positive control for HBV gene expression, HepAD38 cells were also transduced with a non-specific (N.S.) sgRNA construct that does not target any HBV sequence. As a control for maximally repressed HBV expression, HepAD38 cells were also tested in the continuous presence of Tet, which in the HepAD38 cells blocks HBV transcription (Ladner et al., 1997). After transduction and selection, all three sgRNAs reduced HBV DNA levels inside cells by ~10 to ~125-fold and in the supernatant media by ~100-fold to ~800-fold, as measured by real-time PCR (FIG. 8A). Even more impressively, the RT sgRNA suppressed HBV DNA replication to the same extent as Tet addition, which essentially entirely blocks virus replication.

Suppression of cccDNA Formation by HBV Specific Cas9/sgRNA Combinations.

Figure 8B:
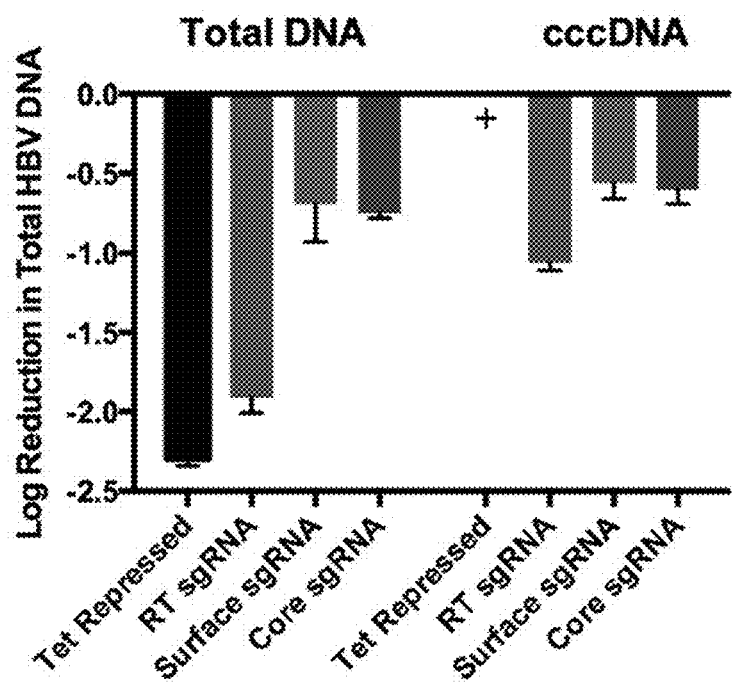

To test the capacity of HBV-specific Cas9/sgRNA combinations to eliminate cccDNA accumulation, transduced HepAD38 cells were also analyzed for the level of cccDNA accumulation by real-time PCR after 14 days in culture using previously described cccDNA-specific primers (Chen et al., 2004). Remarkably, the HBV RT-specific sgRNA suppressed cccDNA formation by ~10-fold, while the surface Ag and core-specific sgRNAs repressed cccDNA levels by ~4-fold (FIG. 8B). Total intracellular HBV DNA accumulation was reduced by ~8-fold by the HBV surface Ag and core-specific sgRNAs, and were repressed by ~80-fold by the RT specific sgRNA (FIG. 8B). Impressively, the HBV RT specific sgRNA was therefore able to reduce HBV cccDNA formation by ~90% and total HBV intracellular DNA accumulation by ~99%.

HBV-Specific Cas9/sgRNA Combinations Reduce HBV Surface Ag Secretion.

Figure 8C:
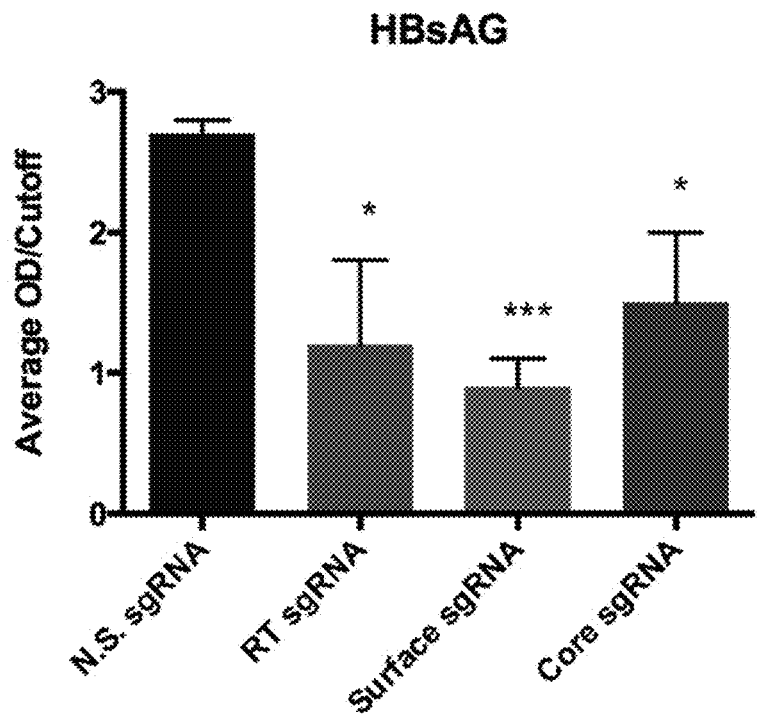
Figure 8D:
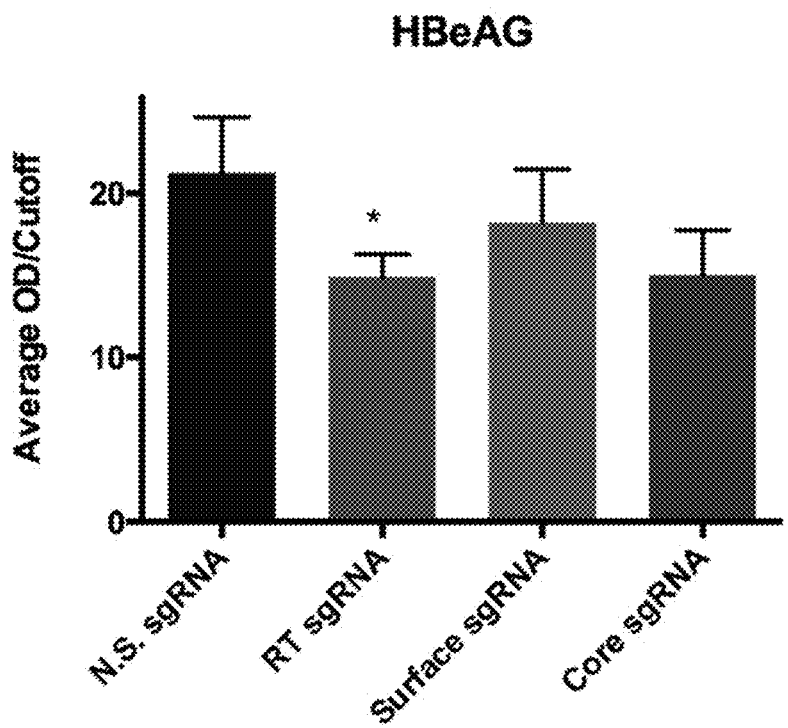

In HepAD38 cells, analysis of the level of HBV surface Ag (HBsAg) and "e" Ag (HBeAg) secretion represents a useful assay for screening for antivirals that inhibit HBV replication and/or viral gene expression. To determine if HBV-specific Cas9/sgRNA combinations can suppress secretion of these viral antigens, we performed an ELISA assay using the supernatant media of transduced HepAD38 cells harvested after 12 days in culture. Low levels of secreted HBsAg were observed in the supernatant of HepAD38 cells transduced with HBV-specific sgRNAs targeting the RT, surface and core genes but not the N.S. sgRNA. Indeed, the surface Ag-specific sgRNA suppressed HBsAg production to nearly undetectable levels (FIG. 8C), possibly consistent with the mutational inactivation of this viral gene due to editing by the cognate Cas9/sgRNA combination. We also observed a statistically significant reduction in HBeAg secretion in the cells transduced with the RT specific sgRNA, indicating perhaps a global reduction in cccDNA in this case (FIG. 8D). In contrast, we did not observe a significant reduction in HBeAg for the Core and Surface sgRNAs, and this likely results from this protein's secretion and exceptional stability. In contrast to the HBsAg ORF, it should be noted that none of the sgRNAs employed directly target this viral ORF for mutagenic inactivation.

Mutational Inactivation of HBV by Cas9/sgRNA Combinations.

While the observed depletion of total HBV DNA and cccDNA accumulation was extensive (FIGS. 8A and 8B), we were also curious as to the mutational status of the residual viral DNA as Cas9 cleavage of chromosomal targets usually results in the introduction of small sequence insertions or deletions (indels) (Shalem et al., 2014). For this purpose, we focused on HepAD38 cells transduced with the sgRNA specific for the active site YMDD motif of the HBV RT gene (FIG. 7A). We harvested total DNA from the HepAD38 cells transduced with the RT-specific Cas9/sgRNA combination that we had previously shown effectively knocked down viral DNA levels (FIGS. 8A and 8B) and subjected the DNA to PCR amplification using HBV RT specific primers followed by cloning and sequencing of the resultant HBV DNA fragments. Seventy-three deletion mutations located at or immediately adjacent to the predicted Cas9 cleavage site present 3 bp 5' to the target DNA PAM sequence were recovered, and we also detected five insertion mutations at this same location in the HBV genome. Of the 103 recovered viral sequences, 78 (76%) were found to be mutated and, interestingly, the bulk of the amplicons recovered were predicted to be lethally mutagenized; even an in-frame insertion or deletion would be highly detrimental as these residues are required for HBV RT function and therefore highly conserved. In conclusion, expression of a Cas9/sgRNA combination specific for the HBV RT gene not only dramatically reduced viral DNA levels, as expected (FIGS. 8A and 8B), but also mutationally inactivated the majority of the low level of residual viral DNA.

Enhanced Inhibition of HBV DNA Accumulation by Antivirals in Combination with Cas9/sgRNAs.

Figure 9A:
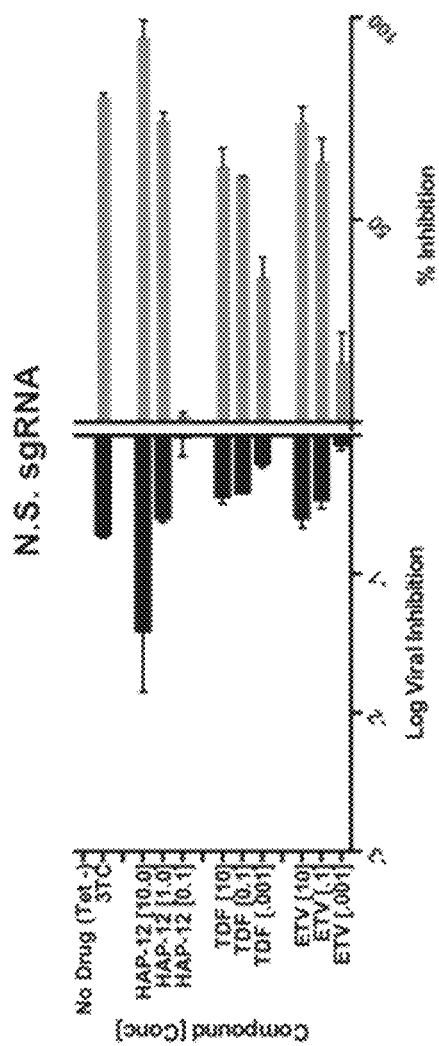
Figure 9B:
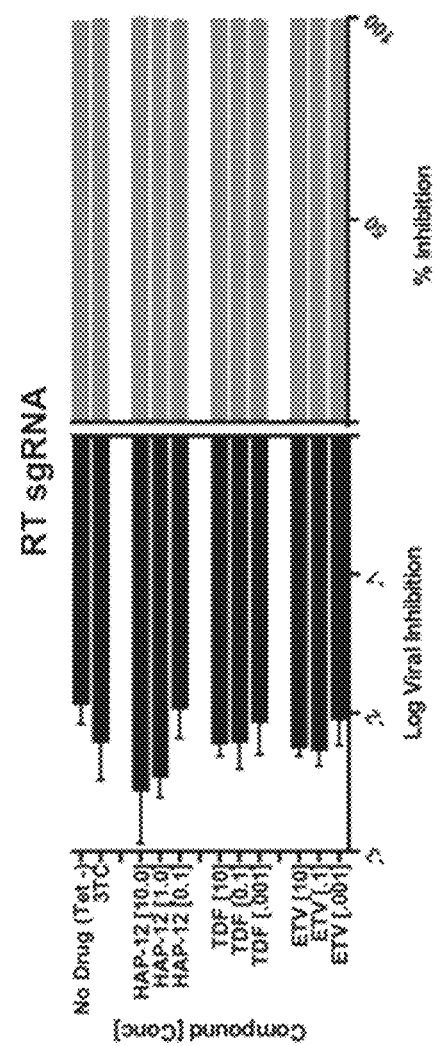

To assess the possibility that potent RT inhibitors (TDF, ETV or 3TC) or a viral assembly inhibitor (HAP12) could enhance elimination of residual virus from HBV-specific Cas/sgRNA expressing cells, we treated HepAD38 cells at concentrations that only partly inhibit HBV DNA replication in this system, as measured by real-time PCR of secreted HBV DNA. First, we assessed the level of viral inhibition in cells expressing Cas9 and the control N.S. sgRNA and all inhibitors tested exhibited the expected dose response (FIG. 9A). Remarkably, and as previously observed (FIG. 8A), HepAD38 cells expressing the HBV RT-specific sgRNA showed essentially complete suppression of secreted HBV DNA accumulation and gained no added benefit from the viral replication inhibitors employed (FIG. 9B). However, with the less effective surface Ag and core-specific sgRNAs, there was a modest but readily detectable enhancement of the level of induced inhibition of secreted HBV DNA in the presence of the antivirals, as shown in FIGS. 9C and 9D. To further confirm these results, we used a constitutively HBV-expressing cell system, HBV2.2.15 cells (Liu et al., 2004; Sells et al., 1987). After transduction with Cas9/sgRNA expressing lentiviral constructs and selection, we observed that extracellular levels of HBV DNA were suppressed by ~98%, ~80%, and ~90%, respectively, by the RT, surface Ag, and core specific Cas9/sgRNA combinations (Table 1). Importantly, treatment of these cells with 1 μM of TDF, ETV, HAP12 or 3TC demonstrated a clear at least additive effect, leading to more efficient elimination of residual HBV DNA replication, for the less effective surface Ag- and core-specific sgRNA in 2.2.15 cells (Table 1). In the case of the RT-specific sgRNA, the detection of a possibly synergistic level of inhibition was again largely prevented by the extremely high efficacy of this Cas9/sgRNA combination.

TABLE 1

Antiviral activity of TDF, ETV, HAP12, and 3TC in HBV2.2.15 cells. Percent inhibition of HBV DNA release into the supernatant medium relative to untreated, HBV2.2.15 cells expressing the non-specific control sgRNA.

| Compound | N.S. sgRNA | HBV RT sgRNA | HBV surface sgRNA | HBV core sgRNA |
| --- | --- | --- | --- | --- |
| Untreated | 0.00 | 97.6 ± 0.2 | 79.6 ± 3.9 | 90.3 ± 1.4 |
| TDF, 1 μM | 68.1 ± 1.5 | 98.9 ± 0.2 | 95.9 ± 0.7 | 97.0 ± 0.3 |
| ETV, 1 μM | 78.3 ± 7.9 | 98.5 ± 1.0 | 97.6 ± 1.1 | 97.9 ± 0.6 |
| HAP12, 1 μM | 77.5 ± 5.2 | 97.5 ± 0.7 | 98.0 ± 0.3 | 97.6 ± 0.1 |
| 3TC, 1 μM | 61.4 ± 6.2 | 99.1 ± 0.03 | 96.3 ± 0.1 | 97.1 ± 0.5 |

N.S., non-specific,
RT, reverse transcriptase.
All values represent the average ± SD of an experiment performed in triplicate.

Cytotoxicity Analysis

For HepAD38 cells transduced with lentiviral sgRNA/Cas9 expression vectors cytotoxicity assays were performed, and no cellular toxicity was observed even at late time points.

Figure 10:
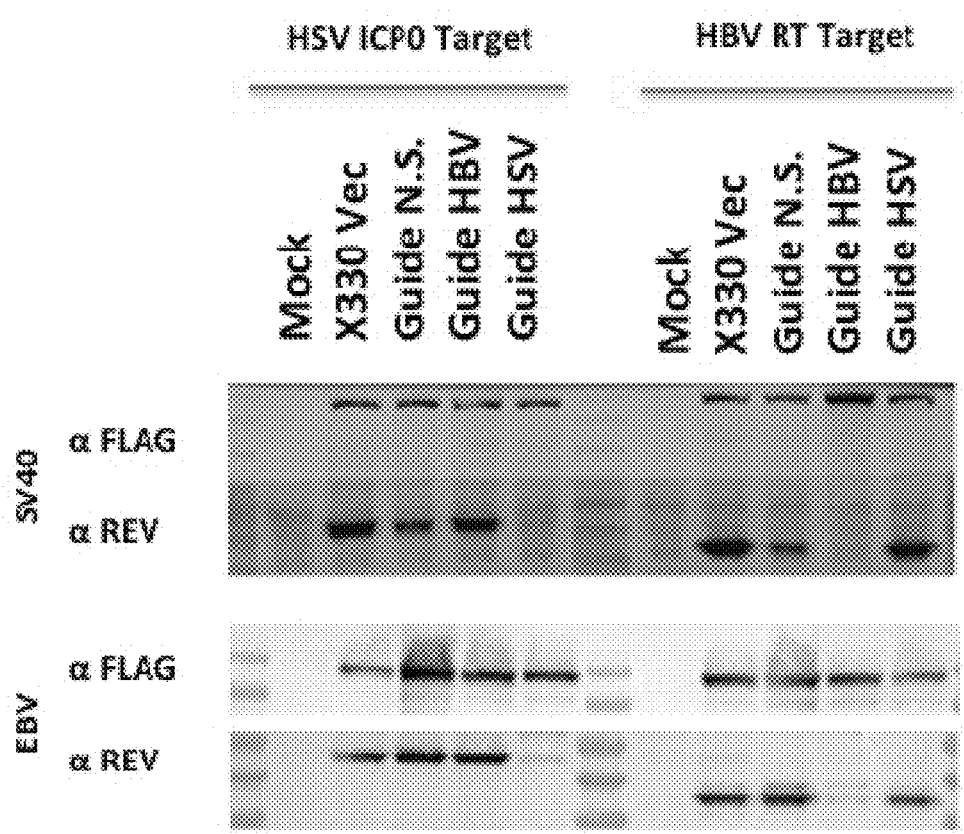
FIG. 10 shows that RGN cleavage results in DNA episome elimination from culture.

Example 3: RGN Cleavage of HSV or HBV Results in DNA Episome Elimination from Culture To demonstrate whether Cas9 could target viral episomal DNA, SPCas9 was used to target two essential viral genes, one encoding HSV-1 ICP0 and the other HBV reverse transcriptase in the context of the reporter assay detailed in FIG. 1A. In contrast to the expected reduction in both GFP intensity and frequency predicted by the rate of mutagenesis induced by non-homologous end joining, we observed a binary result interpretable as elimination of the episome from many cells in culture. This was the case for episomes based on either an SV40- or EBV-derived viral origin of replication, as shown again by Western blot using an antibody specific to Rev (FIG. 10). This episome elimination phenomenon is novel and advantageous, and both HSV-1 and HBV gRNAs can be combined to target multiple viral genes simultaneously, thus enhancing the desired inhibitory effect.

Example 4: Expression of Functional CRISPR/Cas Single Guide RNAs Using Very Small tRNA Promoters CRISPR/Cas9 Constructs, tRNA, and sgRNA Design.

Human tRNA sequences were obtained from the Genomic tRNA database and the MHV tRNA-7 sequence was obtained from Bogerd et al. 2010. (Mol. Cell 37, p135-142, 2010). To generate a tRNA-sgRNA expression construct, overlapping oligonucleotides were assembled to create a tRNA fused to an sgRNA scaffold and a pol III termination signal. Between the tRNA and the sgRNA scaffold, two BsmBI or BbsI sites were incorporated to allow for the insertion of variable targeting sequences. tRNA-sgRNA cassettes were then cloned into Cas9 expression vectors pCMVSau (discussed more fully below), pCMVNme, or pX330 (Addgene, plasmid #42230) expressing S. aureus, N. meningitidis, or S. pyogenes Cas9, respectively. In the case of pX330 the U6 promoter was exchanged for the tRNA-sgRNA cassette.

Table 2 below shows the tRNA sequences tested in the Results section.

TABLE 2

| tRNA Sequences | |
| --- | --- |
| tRNA-99 (Gln); SEQ ID NO: 41 | GGTTCCATGGTGTAATGGTTAGCACTCTGGA CTCTGAATCCAGCGATCCGAGTTCAAATCTC GGTGGAACCT |
| tRNA-128 (Gly); SEQ ID NO: 42 | GCATTGGTGGTTCAGTGGTAGAATTCTCGCC TGCCACGCGGGAGGCCCGGGTTCGATTCCCG GCCAATGCA |
| tRNA-115 (Asn); SEQ ID NO: 43 | TGTCTCTGTGGCGCAATCGGTtAGCGCGTTC GGCTGTTAACTGAAAGGtTAGTGGTTCGAGC CCACCCGGGGACG |
| tRNA-7 (His); SEQ ID NO: 44 | GCCGTGATCGTATAGTGGTTAGTACTCTGCG TTGTGGCCGCAGCAACCTCGGTTCGAATCCG AGTCACGGCA |
| tRNA-49 (Gln-2); SEQ ID NO: 45 | GGTTCCATGGTGTAATGGTTAGCACTCTGGA CTCTGAATCCAGCGATCCGAGTTCAAATCTC GGTGGAACCT |
| tRNA-87 (Glu); SEQ ID NO: 46 | TCCCTGGTGGTCTAGTGGTtAGGATTCGGCG CTCTCACCGCCGCGGCCCGGGTTCGATTCCC GGTCAGGGAA |
| tRNA-2 (Pro); SEQ ID NO: 47 | GGCTCGTTGGTCTAGGGGTATGATTCTCGCT TAGGGTGCGAGAGGTCCCGGGTTCAAATCCC GGACGAGCCC |
| tRNA-25 (Cys); SEQ ID NO: 48 | GGGGGTATAGCTCAGGGGTAGAGCATTTGAC TGCAGATCAAGAGGtCCCCAGTTCAAATCTG GGTGCCCCCT |
| tRNA-5 (Tyr); SEQ ID NO: 49 | GTCAGTGTTGCACAACGGTTAAGTGAAGAGG CTGTAAACCCAGACTGGATGGGTTCAATTCC CATCTCTGCCG |

TABLE 2-continued tRNA Sequences

MHV tRNA-5; SEQ ID NO: 50
GCCAGGGTAGCTCAATTGGTAGAGCATCAGG
CTAGTATCCTGTCGGTTCCGGTTCAAGTCCG
GGCCCTGGTT

Reporter Assays.

Reporter assays with 293T cells were performed by using the calcium phosphate transfection method. Briefly, 293T cells were plated at ~1.25×10⁵ cells per well in 12-well plates and transfected with a 4:1 ratio of the RGN expression plasmid to the FLuc-based indicator plasmid as well as 10 ng of a RLuc plasmid. Transfected 293T cells were then harvested 72 hours post transfection in Passive Lysis Buffer (Promega) and assayed for both FLuc and RLuc activity (Promega Dual-Luciferase Reporter Assay System) with RLuc serving as an internal control and normalization factor.

Cell Culture.

293T cells were grown in Dulbecco's modified Eagle medium (DMEM) supplemented with 10% fetal bovine serum (FBS), 2 mM antibiotic-antimycotic (Gibco Cell Culture), and 50 µg/ml gentamicin (Life Technologies) at 37° C.

Northern Blot Assays.

Northern blot assays with 293T cells were performed by using the PEI transfection method. 293T cells were plated at ~5.25×10⁶ cells in 10 cm dishes and transfected with 20 µg of the RGN expression plasmid. 293T cells were then harvested 72 hours post-transfection in Trizol (Life Technologies). Total RNA was isolated and fractionated on a 10% TBE-Urea Gel (Bio-Rad) and RNA was transferred to HyBond-N membrane (Amer-sham) and UV crosslinked (Stratalinker, Stratagene). Membranes were pre-hybridized in ExpressHyb (Clontech) and then incubated at 37° C. with a $^{32}$P-end labeled oligonucleotide. Membranes were washed with 2×SSC/0.1% SDS at 37° C. and sgRNAs visualized by autoradiography.

Results

Current CRISPR/Cas vectors generally rely on the Cas9 protein encoded by *Streptococcus pyogenes* (Spy), which is encoded by an ~4.2 kb gene. However, as discussed previously by ourselves and others, effective delivery of both the Cas9 gene and cognate sgRNAs into tissues in vivo will likely require the development of adeno-associated virus (AAV)-based vectors, as only AAV can be readily produced at titers sufficient to transduce enough cells in vivo to exert the desired phenotypic effect. However, AAV vectors have a DNA packaging limit of ~4.7 kb of which ~290 bp must be dedicated to the two invariant AAV inverted terminal repeats (ITRs), leaving only ~4.4 kb as the payload capacity. To circumvent this problem, other groups generated an AAV vector expressing the ~4.2 kb Spy Cas9 gene using a minimal promoter element and then used a second AAV to express a cognate sgRNA. (Swiech et al, Nature Biotech 33, p102-106, 2015). This approach requires co-infection by each of these two AAVs in order to induce genome editing, which would clearly not be optimal in an in vivo setting. For this reason, there has been considerable interest in identifying highly active smaller Cas9 proteins, encoded by other bacterial species. For example, both the *Neisseria meningitidis* (Nme) and *Staphylococcus aureus* (Sau) Cas9 genes are only ~3.2 kb in size. However, this would still leave only ~1.2 kb of space for the RNA polymerase II (pol II) promoter and poly(A) addition site required for Cas9 expression as well as a nuclear localization signal (NLS) required for Cas9 nuclear import, the sgRNA and the RNA polymerase III (pol III) promoter required for sgRNA transcription. In many cases, two or more sgRNAs would be desirable, for example to allow versions of Cas9 mutated to only cleave one strand of a dsRNA molecule, so-called Cas9 nickases, to induce DNA cleavage by nicking two closely adjacent sites on opposite strands of the target DNA molecule (Ran et al Cell 154, p1380-1389,2013). Also, in some cases more than one DNA target may need to be edited simultaneously to exert the desired phenotypic effect.

Previous work has focused on using the U6 pol III promoter to drive sgRNA transcription. The U6 promoter, while very effective, is ~254 bp long (see SEQ ID NO: 51) and two U6 promoters would therefore require over 10% of the entire packaging capacity of an AAV vector. It is therefore desirable to identify equally effective pol III-dependent promoters that are much smaller than U6. We show that tRNA promoters, of human or viral origin, can be used to express high levels of sgRNAs specific for a wide range of DNA targets and bacterial Cas9 proteins (see Table 2).

Previously, we have demonstrated that mouse γ-herpesvirus 68 (MHV68) encodes several ~60-nt long pre-microRNA (pre-miRNA) molecules that are initially transcribed as a fusion transcript consisting of a 5' viral tRNA moiety fused to a 3' pre-miRNA hairpin (Bogerd et al, Mol. Cell 37, p135-142, 2010). These are then precisely separated due to cleavage by the cellular enzyme tRNase Z, which normally functions to define the precise 3' end of cellular tRNAs. We have also demonstrated that human tRNAs, when fused to a pre-miRNA hairpin of human or viral origin, gives rise to both the pre-miRNA intermediate and a functional mature miRNA and this again requires processing by tRNase Z to release the tRNA from the pre-miRNA. We therefore wondered whether human tRNAs could also be used to generate functional sgRNAs via a precursor tRNA fusion intermediate, as schematically shown in FIG. 11A. When compared to previously described tRNA:pre-miRNA fusion transcripts, this tRNA:sgRNA fusion differs in that the sgRNA is both significantly larger (~101 nt vs. ~60 nt) and folded into a more complex secondary structure.

Figure 11B:
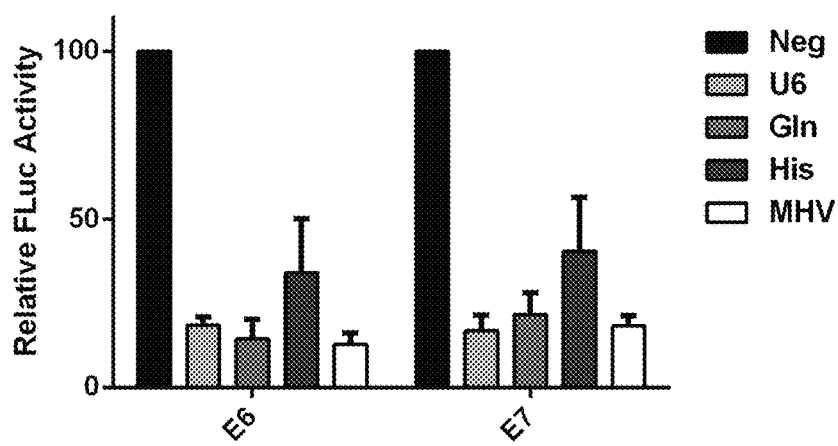
FIG. 11B is a graph showing relative luciferase activity from 293T cells co-transfected with plasmids expressing S. pyogenes (Spy) Cas9 protein and sgRNAs specific for the HPV-18 E6 or E7 genes or a control sgRNA, and their cognate indicator plasmids. sgRNAs were expressed from either the U6 promoter or a tRNA.

Initially we generated predicted fusion transcripts consisting of a human glutamine tRNA (SEQ ID NO: 41), a human histidine tRNA (SEQ ID NO: 44) or an MHV68 tRNA (M1-7; SEQ ID NO: 50)) linked to Spy Cas9 sgRNAs specific for a target DNA sequence derived either from the human papillomavirus serotype 18 (HPV-18) E6 or E7 gene (SEQ ID NO: 8 and 10, respectively), as described above. Indicator plasmids consisting of these viral target sequences linked to the FLuc gene, constructed as described above, were then co-transfected into 293T cells along with a plasmid encoding Spy Cas9, plasmids encoding each of the tRNA promoters, or the U6 promoter, linked to the same sgRNA and finally a RLuc-based internal control plasmid. Cells were harvested at 72 h post-transfection and FLuc and RLuc levels determined. As shown in FIG. 11B, we observed effective and comparable knockdown of both the E6- and E7-based indicator constructs by not only the U6 promoter-based sgRNA expression vector but also by the vectors based on the tRNA$_{GLN}$ and tRNA$_{MHV-7}$ promoters, while the tRNA$_{HIS}$ vector appeared slightly less effective.

Figure 11C:
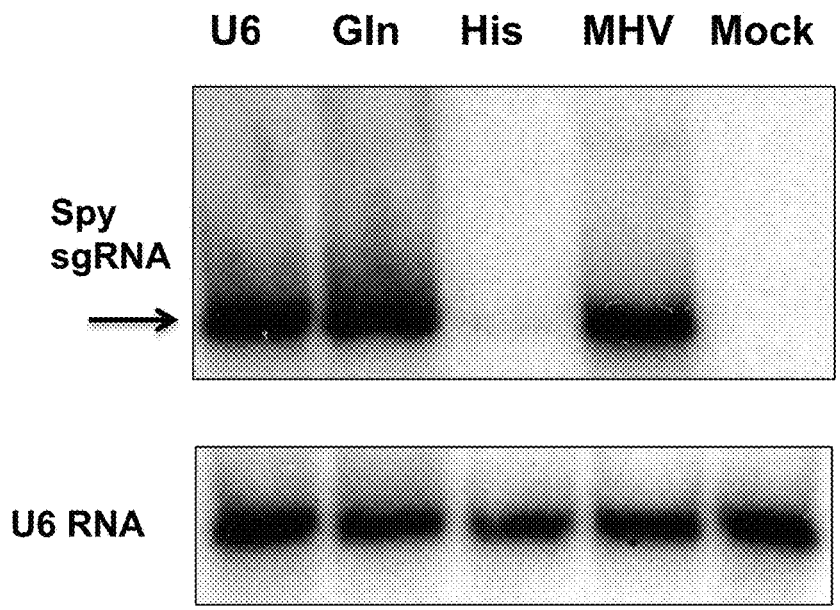
FIG. 11C shows a Northern blot of Spy sgRNAs from 293T cells transfected with a plasmid expressing S. pyogenes Cas9 protein and sgRNAs specific for the HPV-18 E7 gene expressed from either U6 or a tRNA. Endogenous cellular U6 RNA served as a loading control. The arrow indicates the precicted location of the Spy sgRNAs.

We next analyzed the expression level of the E7-specific sgRNA in the transfected 293T cells using an Spy sgRNA scaffold-specific probe. As shown in FIG. 11C, we saw high and comparable levels of the mature E7-specific sgRNA produced by the U6, tRNA$_{GLN}$ and tRNA$_{MHV1-7}$-based vectors but far less from the tRNA$_{HIS}$-based vector. We did not observe a detectable level of the predicted ~170-nt tRNA:sgRNA fusion transcript in any of the cultures transfected with tRNA-based vectors.

To extend these studies to a distinct Cas9 protein with a different sgRNA scaffold, we next analyzed the expression and function of Nme Cas9 sgRNAs transcribed using the U6 or tRNA promoters. The Nme sgRNA scaffold (SEQ ID NO: 37) is entirely different in sequence from Spy sgRNA scaffold (SEQ ID NO: 36) and also somewhat larger in size (Hou et al, PNAS 110, p15644-15649, 2013). We again analyzed Cas9 activity against two different DNA targets, each of which consists of a bacterially derived, natural protospacer sequence called protospacer 9 (P9; SEQ ID NO: 28) or P25 (SEQ ID NO: 29). The Nme Cas9 protospacer adjacent motif (PAM) used here was 5-NNNGATT-3', as previously reported by Hou et al., 2013.

Figure 12A:
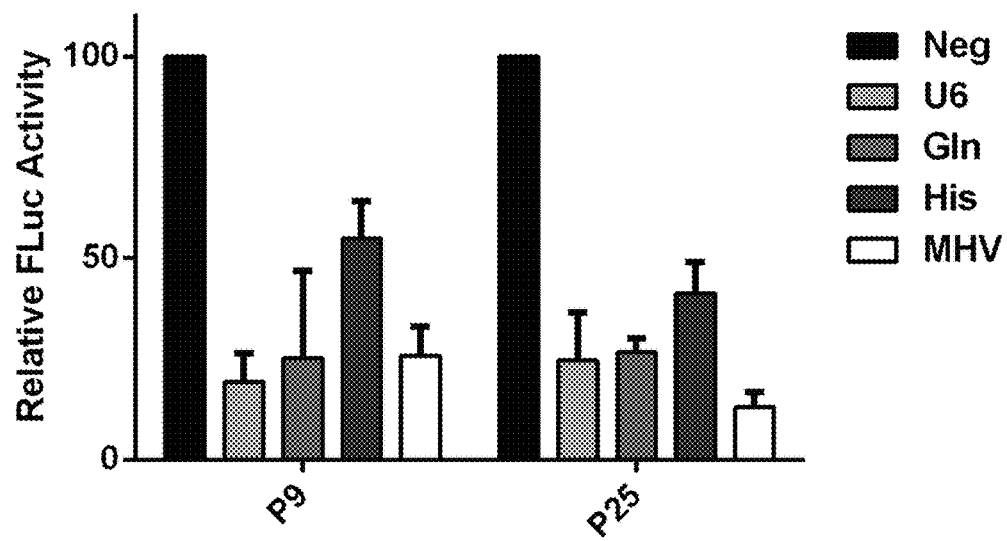
FIG. 12A is a graph showing relative luciferase activity from 293T cells co-transfected with plasmids expressing N. meningitidis (Nme) Cas9 protein and sgRNAs specific for the bacterially derived protospacer 9 (P9) or P25 DNA sequence or a control sgRNA, and their cognate indicator plasmids. sgRNAs were expressed from either the U6 promoter or a tRNA as indicated.
Figure 12B:
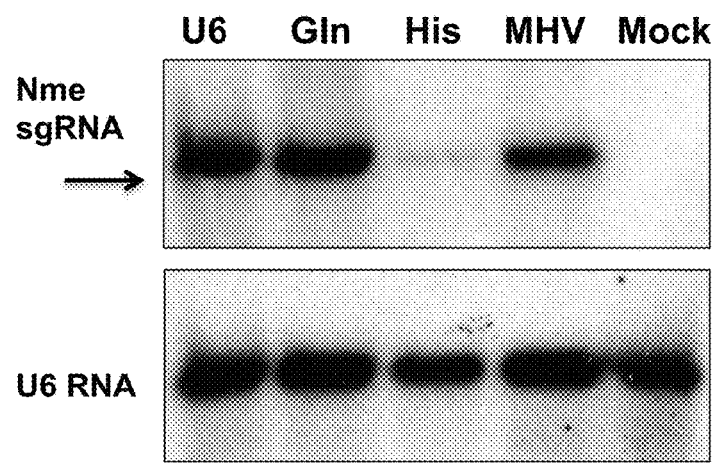
FIG. 12B is a Northern blot of Nme sgRNAs from 293T cells transfected with a plasmid expressing Nme Cas9 and sgRNAs specific for P25 expressed from either U6 or a tRNA as indicated. Endogenous cellular U6 RNA served as a loading control. The arrow indicates the location of the Nme sgRNAs.

As shown in FIG. 12A, we again observed the specific knockdown of the cognate FLuc-based indicator plasmids in co-transfected cells, though this was less than was observed with Spy Cas9 (FIG. 11B). Northern analysis of sgRNA expression, using a probe specific for the Nme sgRNA scaffold, showed closely comparable levels of the P25-specific sgRNA in cells transfected with the U6, tRNA$_{GLN}$ and tRNA$_{MHV1-7}$-based vectors and again far lower levels with the tRNA$_{HIS}$ promoter (FIG. 12B).

Figure 12C:
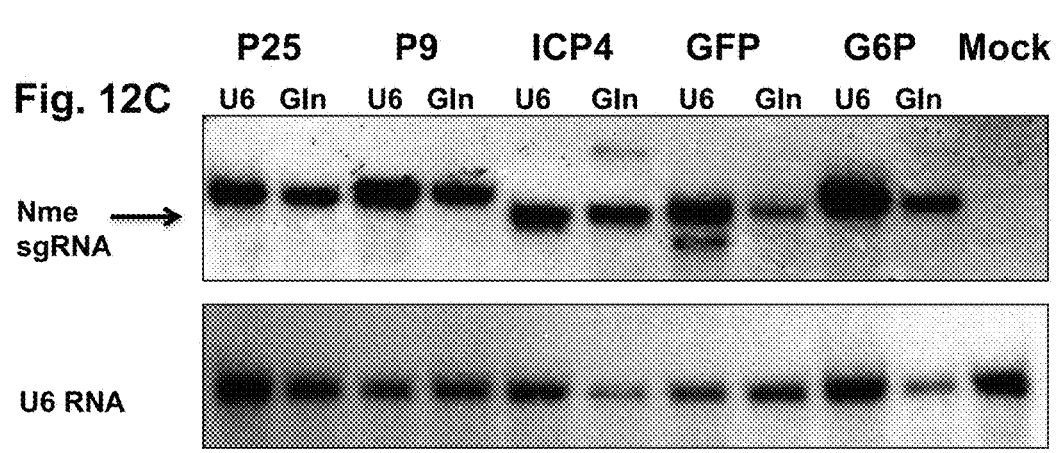
FIG. 12C is similar to FIG. 12A except various sgRNA guide sequences were used. (P25: protospacer 25, P9: protospacer 9, ICP4: HSV-1 infected cell protein 4, GFP: green fluorescent protein, G6P: glucose-6-phosphatase)

To extend these studies, and to test whether different sgRNA variable regions might interfere with tRNase Z-mediated processing of the tRNA:sgRNA fusion transcript, we next analyzed the expression of a wide range of Nme sgRNAs bearing either 25 nt (P25 (SEQ ID NO: 29), P9 (SEQ ID NO: 28), G6P (SEQ ID NO: 65)) or 24 nt (ICP4 (SEQ ID NO: 63), GFP(SEQ ID NO: 64)) variable regions using either the U6 or tRNA$_{GLN}$ promoter. As may be observed (FIG. 12C) we saw generally closely comparable levels of sgRNA expression in all cases. In the case of the ICP4-specific tRNA$_{GLN}$:sgRNA vector, we also noticed a trace amount of a larger transcript migrating at the predicted ~200-nt size of the initial tRNA:sgRNA fusion transcript (FIG. 12C, lane 6).

Figure 13A:
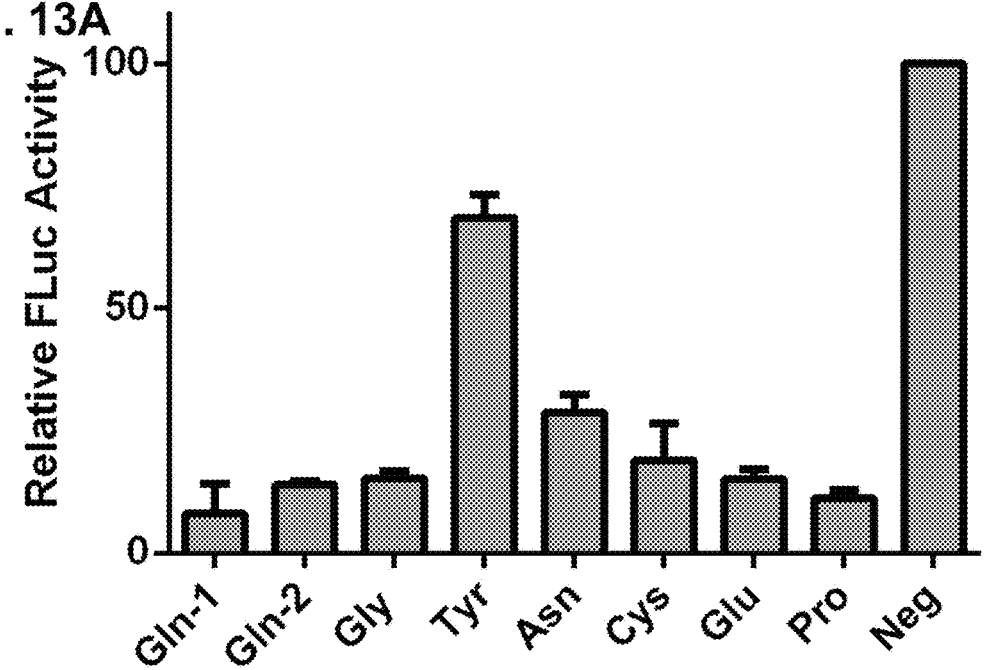
FIG. 13A shows relative luciferase activity from 293T cells co-transfected with plasmids expressing S. aureus (Sau) Cas9 and sgRNAs specific for HSV-1 ICP0 or a control sgRNA, and a cognate indicator plasmid. sgRNAs were expressed from various tRNAs.
Figure 13B:
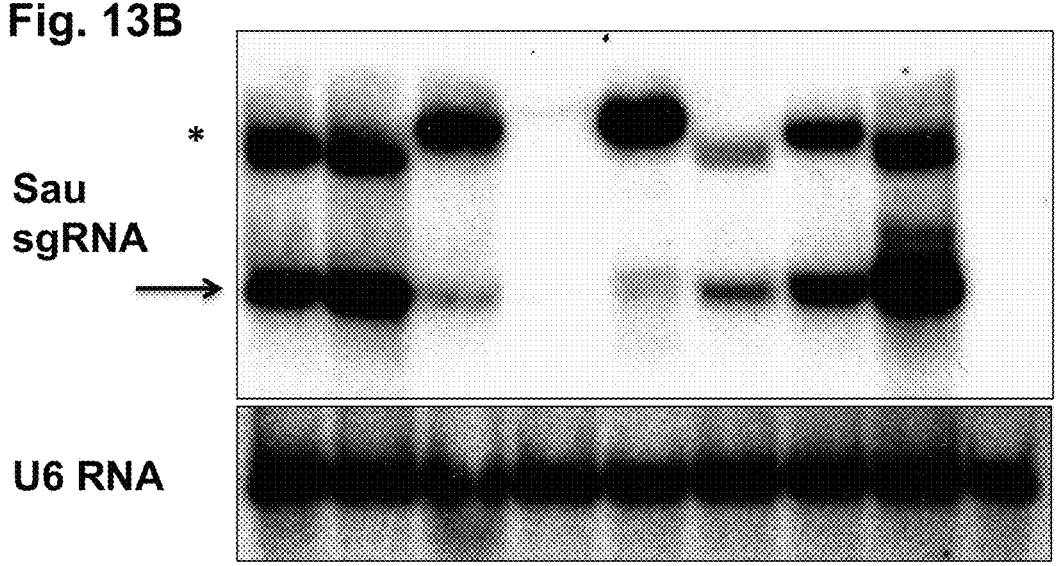
FIG. 13B shows a Northern blot of Sau sgRNAs recovered from 293T cells transfected with a plasmid expressing Sau Cas9 and an sgRNA specific for HSV-1 ICP0 transcribed from a tRNA promoter. Endogenous cellular U6 RNA served as a loading control. The arrow indicates the predicted location of the mature sgRNA while the asterisk indicates unprocessed tRNA-sgRNA fusion transcripts.

The Sau Cas9 gene shares the small ~3.2 kb size of the Nme Cas9 gene and Sau Cas9 is highly active when presented with DNA targets that contain its cognate PAM sequence 5'-NNGRRT-3', where "R" represents a purine residue. As such Sau encodes a promising Cas9 gene for potential use in AAV vectors. To analyze whether we could also produce active Sau sgRNAs using tRNA promoters, we expressed the identical Sau sgRNA, specific for a target within the HSV-1 ICP0 gene (SEQ ID NO: 16), using a wide range of human tRNAs. By indicator assay, we observed strong knockdown when using the human tRNA$_{GLN1}$, tRNA$_{GLN2}$, tRNA$_{GLY}$, tRNA$_{GLU}$ or tRNA$_{PRO}$ promoters to drive sgRNA expression and readily detectable knockdown when using tRNA$_{ASN}$ or tRNA$_{CYS}$ but little or no detectable knockdown when using a tRNA$_{TYR}$ promoter (FIG. 13A). Northern analysis, using a probe specific for the Sau sgRNA scaffold, showed high level expression of the mature sgRNA with the tRNA$_{GLN1}$, tRNA$_{GLN2}$, tRNA$_{GLY}$, tRNA$_{GLU}$ and especially tRNA$_{PRO}$ promoters. Expression of the mature sgRNA was more modest with the tRNA$_{GLY}$, tRNA$_{CYC}$ and tRNA$_{ASN}$ promoters, while the tRNA$_{TYR}$ promoter did not give rise to a detectable signal. Interestingly, and in clear contrast to what was observed with the Spy and Nme sgRNA vectors, we observed a substantial level of the unprocessed ~170-nt tRNA:sgRNA precursor fusion transcript in all cases. The reason for the lower efficiency of processing seen with all of these tRNA:sgRNA fusions is currently unclear, but could relate to the single invariant sgRNA sequence used in this experiment.

Use of the tRNAs as promoters for the sgRNAs in combination with the shorter Nme Cas9 or Sau Cas9 will allow for addition of two sgRNAs and the Cas9 gene to be encoded within the confines of a single AAV vector as described more fully below.

Example 5: Development of Sau Cas9 and AAV Vector Construct

Figure 14A:
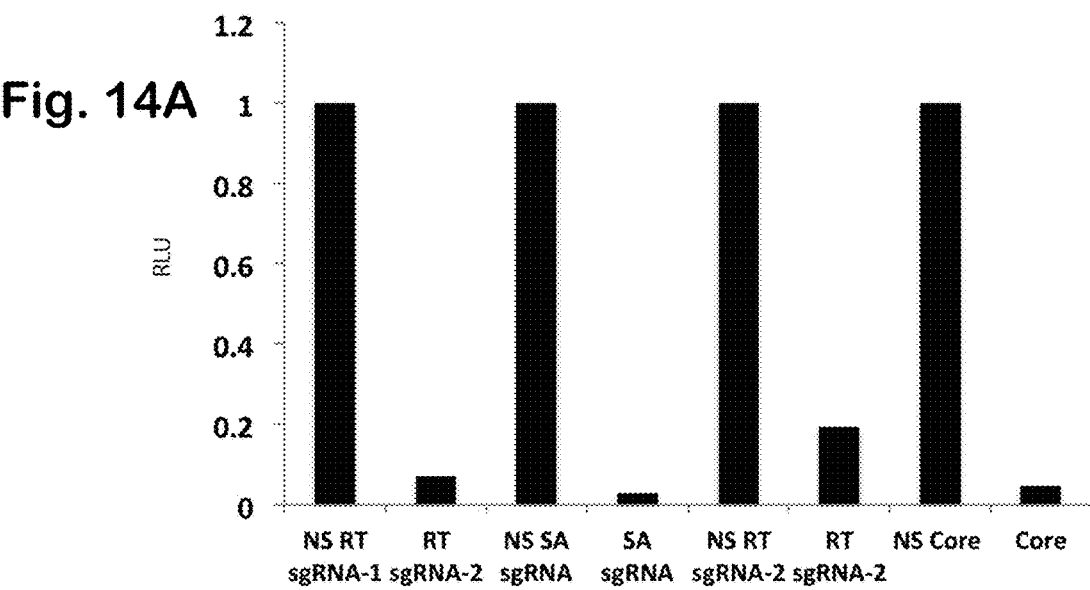
FIG. 14 is a set of figures showing representative evidence of Sau Cas9 and sgRNA function. 293T cells were transfected with indicator constructs containing DNA targets derived from genes expressed by the viruses HBV (FIG. 14A), HSV-1 (FIG. 14B), EBV (FIG. 14C) or HPV-18 (FIG. 14D). In each case, 293T cells were transfected with an indicator FLuc construct, as described above, a vector expressing Sau Cas9 and a vector expressing an sgRNA specific for the viral DNA target in question. A non-specific (NS) sgRNA served as a negative control.
FIG. 14E shows a Western blot in which HeLa cells were transfected with vectors expressing Spy Cas9 and a previously described HPV-18 E6-specific sgRNA or with an AAV-based vector expressing Sau Cas9 and the sgRNAs specific for HPV-18 E6 and E7 shown in FIG. 14D. After 48 hours, the cells were harvested and analyzed for induction of p53 and p21 expression, as is predicted to occur if the E6-specific sgRNA used is able to effectively cleave the HPV-18 E6 gene.
Figure 14B:
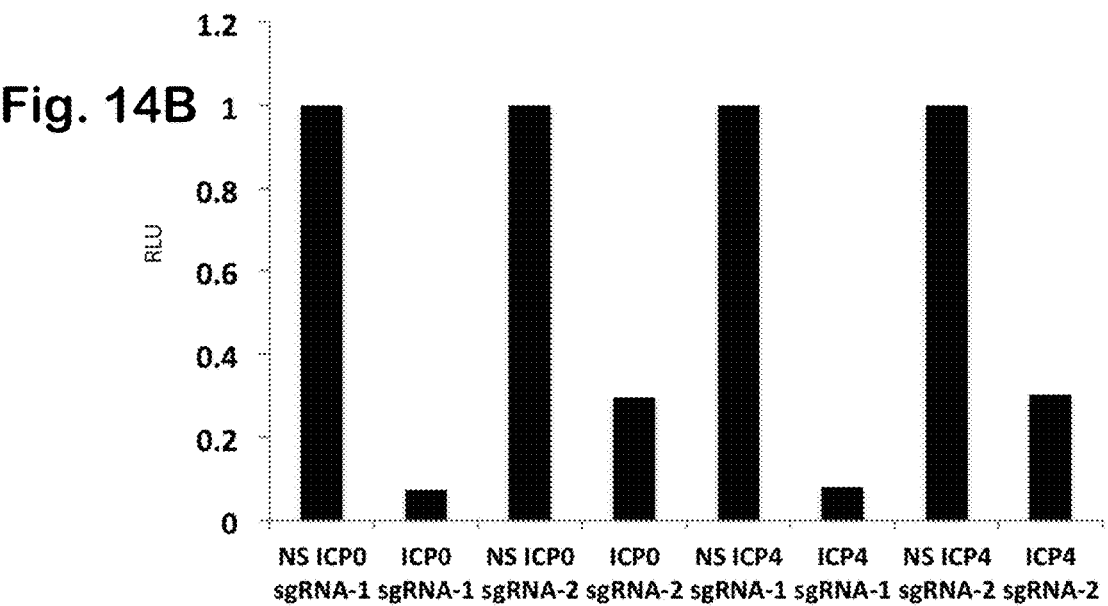
Figure 14C:
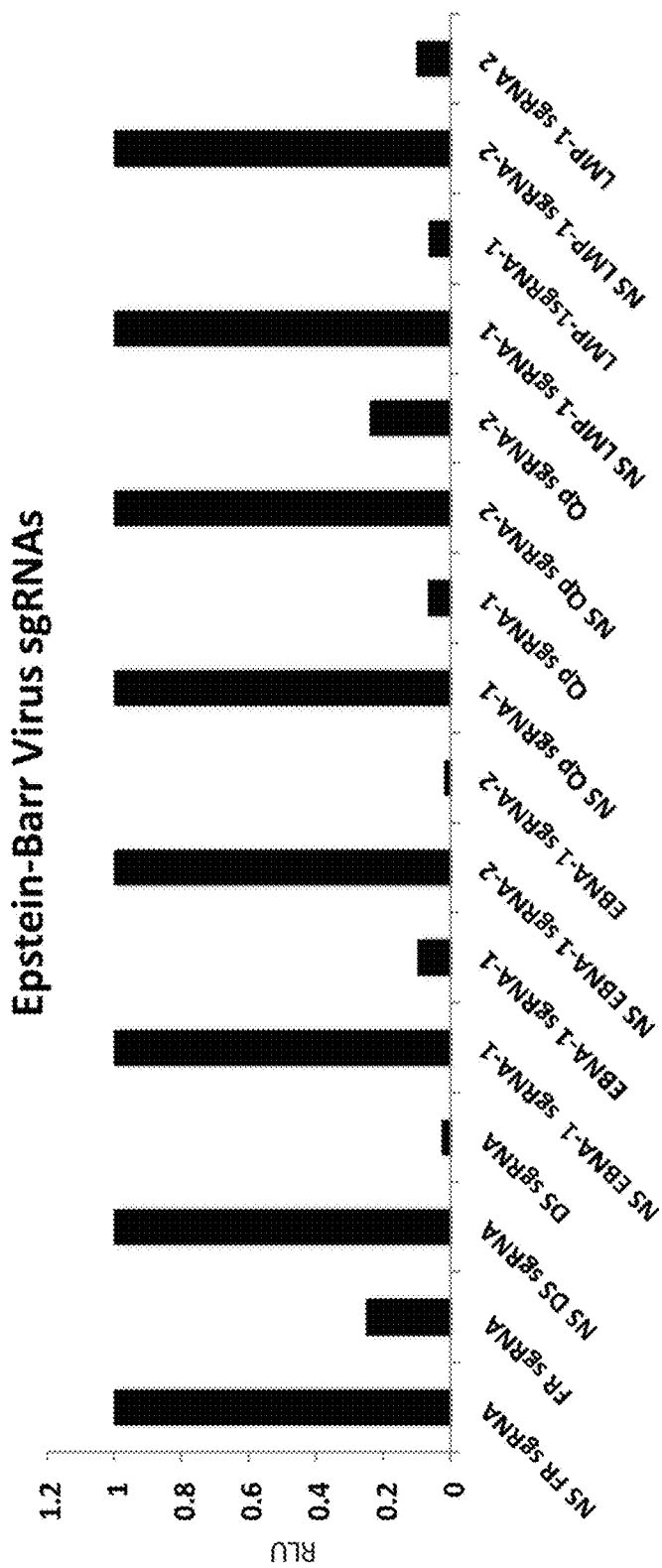
Figure 14D:
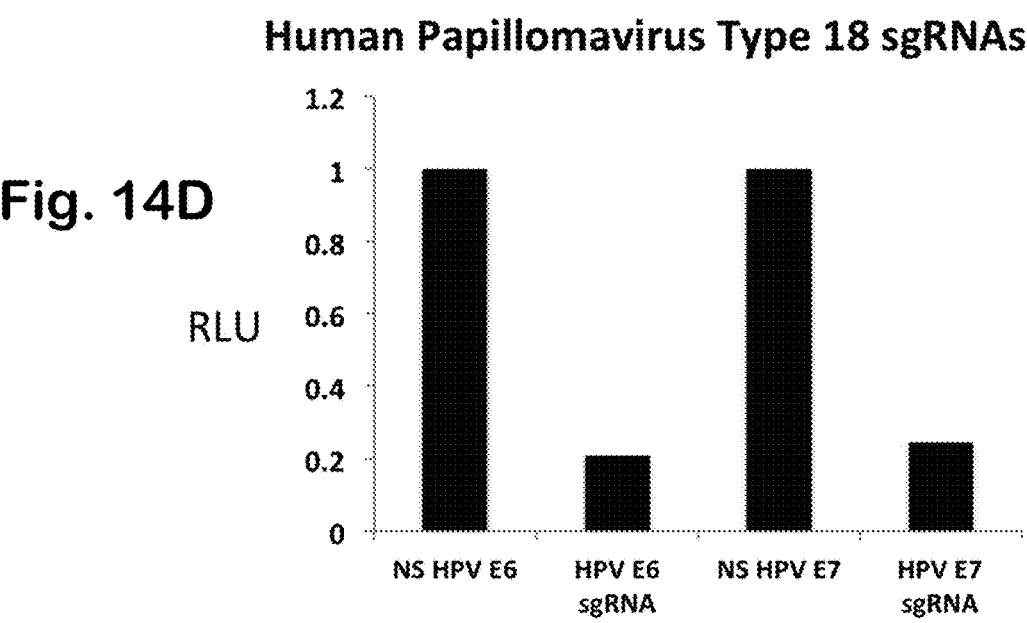
Figure 14E:
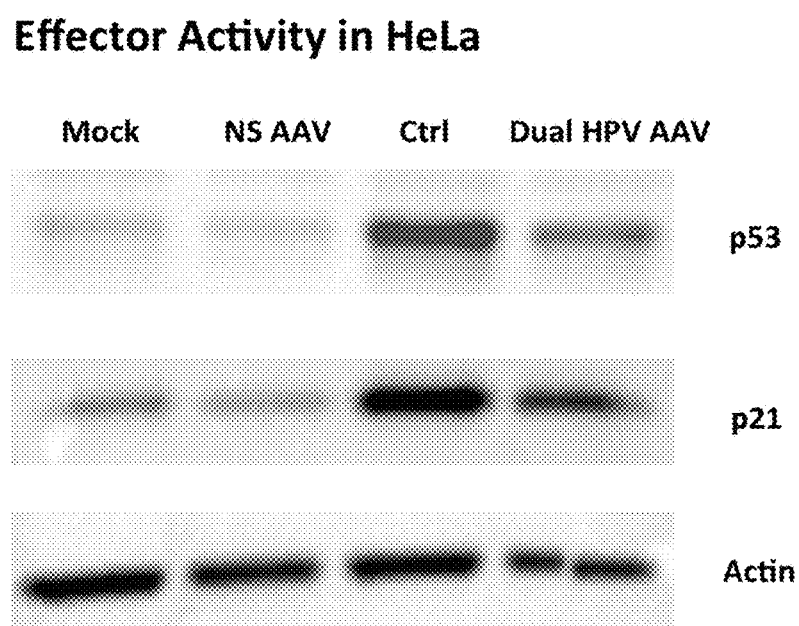

While our initial proof of concept experiments relied on lentiviral vectors to transmit the Cas9 and sgRNAs into cells, AAV represents a well-known and suitable vector for gene therapy applications. As noted above, AAV vectors only allow for about 4.4 kb of genetic cargo and thus to be able to use a single AAV vector we needed a smaller Cas9 as well as the tRNA short promoters to drive expression of the sgRNAs. We developed a codon optimized polynucleotide for expression of the Sau Cas9 (SEQ ID NO: 55) and designed sgRNAs directed to several viruses to test the system. The sgRNAs designed and tested include the following: HBV RT, Surface antigen, (SA) and Core (SEQ ID NO: 4-7); HSV-1 ICP0 and ICP4 (SEQ ID NO: 16-19); EBV FR, DS, EBNA-1, Clp, and LMP-1 (SEQ ID NO: 20-27); and HPV E6 and E7 (SEQ ID NO: 14-15). FIG. 14A-D shows more extensive Sau sgRNA functional data generated using indicator vectors for the viral sequences from HBV, HSV-1, EBV and HPV. FIG. 14E shows the functional data for HPV in the HeLa cells as described more fully above and demonstrates that the p53 and p21 expression is restored in cells showing the sgRNA is cleaving the endogenous HPV-18 E6 gene.

Figure 15:
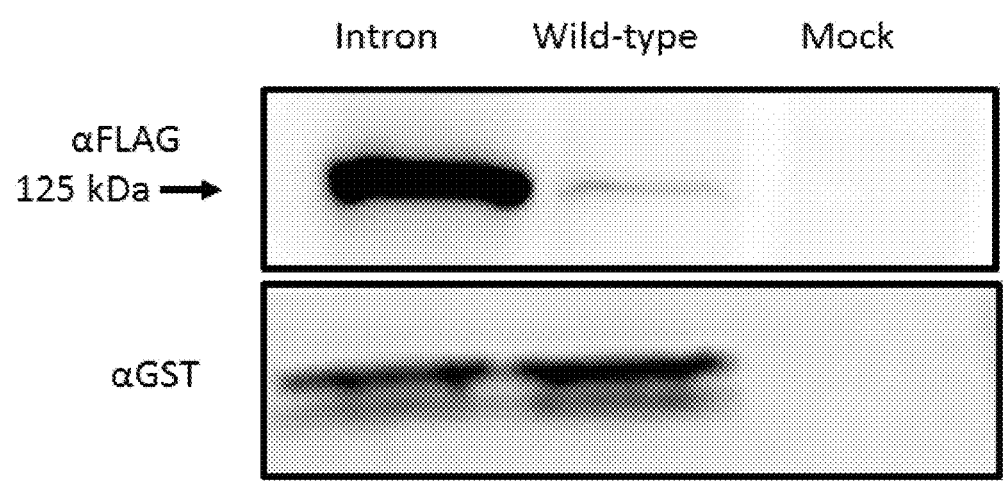
FIG. 15 shows a Western blot demonstrating that an intron inserted into the mRNA 5' untranslated region (5' UTR) greatly enhances Sau Cas9 expression. 293T cells were transfected with an expression vector containing the full length Sau Cas9 gene, with an N-terminal FLAG epitope tag, under the control of the CMV-IE (hCMV immediate early) promoter/enhancer or a similar construct bearing an intron from the rat pre-preinsulin II gene inserted into the Cas9 5' UTR. Cas9 expression was determined by Western blot at 72 h post-transfection using a monoclonal antibody specific for the FLAG epitope tag. This revealed an ~20-fold higher level of Cas9 expression if the intron was included. A co-transfected plasmid expressing glutathione S-transferase (GST) was used as a loading control.

The Sau Cas9 expression was not optimal in our initial construct so we tested whether addition of a 5' intron in the untranslated region (UTR) would effect expression of Sau Cas9. As shown in FIG. 15, addition of the rat pre-proinsulin II intron (shown as SEQ ID NO: 53) greatly enhances Sau Cas9 expression. The expression was increased by about 20 fold with the intron as compared to without the intron.

All the sequences were introduced into the "model" AAV vector illustrated in FIG. 16. This includes the tRNA Gln Pol III promoter (SEQ ID NO: 41), the first sgRNA sequence with the two BsmB1 restriction enzyme sites, used for insertion of variable regions shown in italics and the invariant Sau sgRNA scaffold shown in normal capital letters (GGAGACGGACGTCTCCGTTTTAGTACTCTG-GAAACAGAATCTACTAAAACAAGGCA AAATGC-CGTGTTTATCTCGTCAACTTGTTGGCGAGATTTTTT; SEQ ID NO: 39). The U6 Pol III promoter is included (SEQ ID NO: 51). The second Sau sgRNA sequence is included and has two BbsI restriction enzyme sites used for insertion of variable regions shown in italics followed by the invariant Sau sgRNA scaffold shown in normal capital letters (GGGTCTTCGAGAAGACCCGTTTTAGTACTCTG-GAAACAGAATCTACTAAAACAAGGC AAAATGC-CGTGTTTATCTCGTCAACTTGTTGGCGAGATTTTTT; SEQ ID NO: 40). The EFS Pol II promoter was used to drive Cas9 expression (SEQ ID NO: 52). A 5' untranslated region and intron derived from the rat preproinsulin II genomic gene with the intron underlined and in italics (SEQ ID NO: 53). The nuclear localization signal (NLS) and FLAG epitope tag (SEQ ID NO: 54) is inserted at the amino-terminus of Sau Cas9 with the latter in lower case. Alternative NLS sequences are provided as SEQ ID NOs: 59-62. The Sau Cas9 synthetic gene sequence used is shown as SEQ ID NO: 55 and finally a synthetic poly(A) addition site is shown as SEQ ID NO: 56. The NLS-FLAG-Sau Cas9 protein sequence is provided as SEQ ID NO: 57 and one AAV vector insert is provided as SEQ ID NO: 58.

Figure 17:
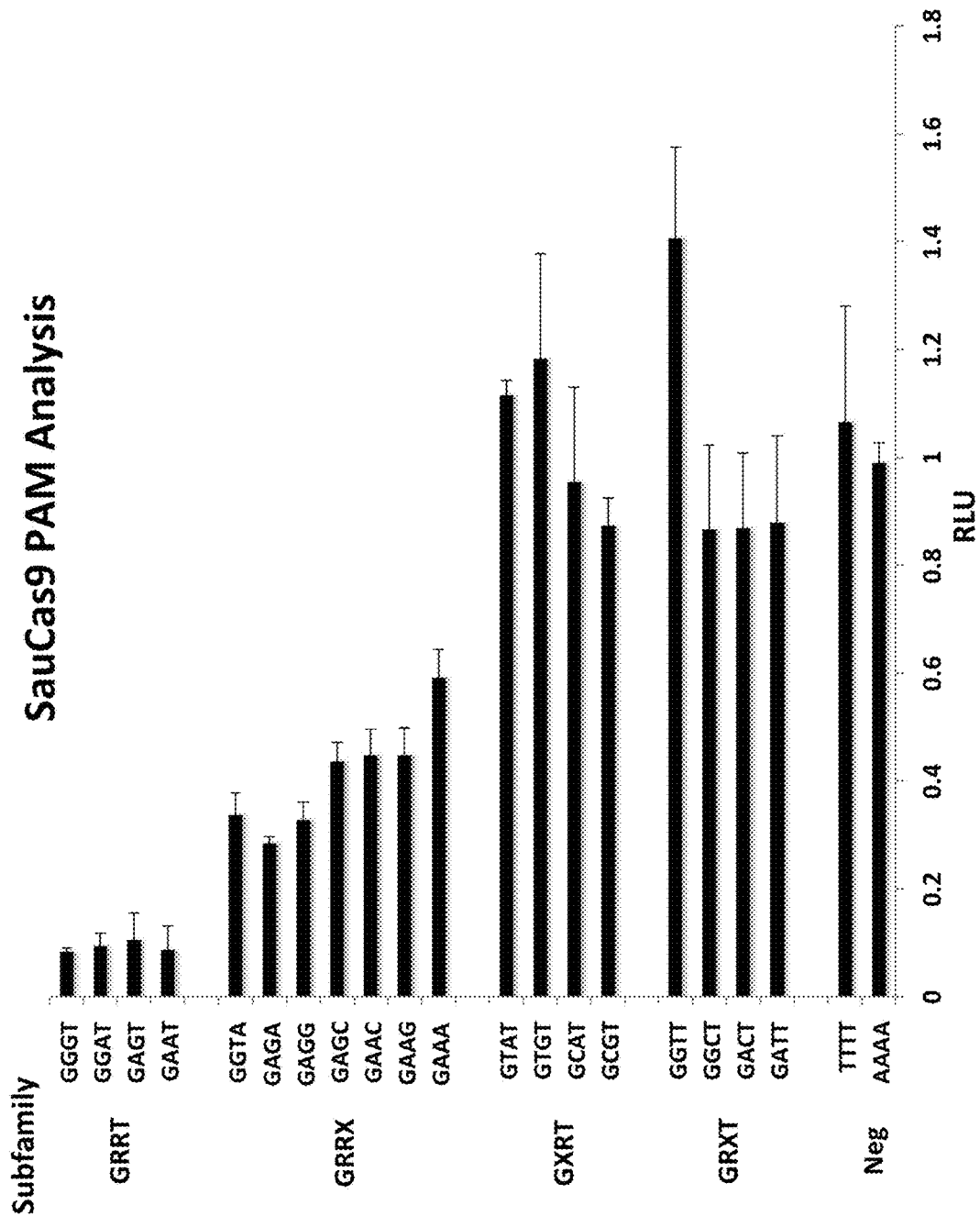
FIG. 17 is a bar graph showing the identification of the Sau Cas9 protospacer adjacent motif (PAM). Indicator constructs containing a wide range of possible PAM sequences were constructed and analyzed, as described in FIG. 1A with FLuc as the reporter, by co-transfection with a Sau Cas9 expression vector and an sgRNA expression vector. This analysis identified 5'-NNGRRT-3' (where N is any nucleotide and R is either G or A) as the most active PAM for the Sau Cas9 protein.

To further optimize use of the Sau Cas9, we needed to identify the Sau Cas9 protospacer adjacent motif (PAM). We constructed luciferase indicator constructs containing a wide range of possible PAM sequences including -GRRT, -GRRX, -GXRT, and -GRXT. The results are shown in FIG. 17. This analysis identified 5'-NNGRRT-3' where N is any nucleotide and R is G or A as the most active PAM for Sau Cas9.

Example 6: Targeting HIV-1 with the CRISPR/Cas 9 Vectors

Figure 18A:
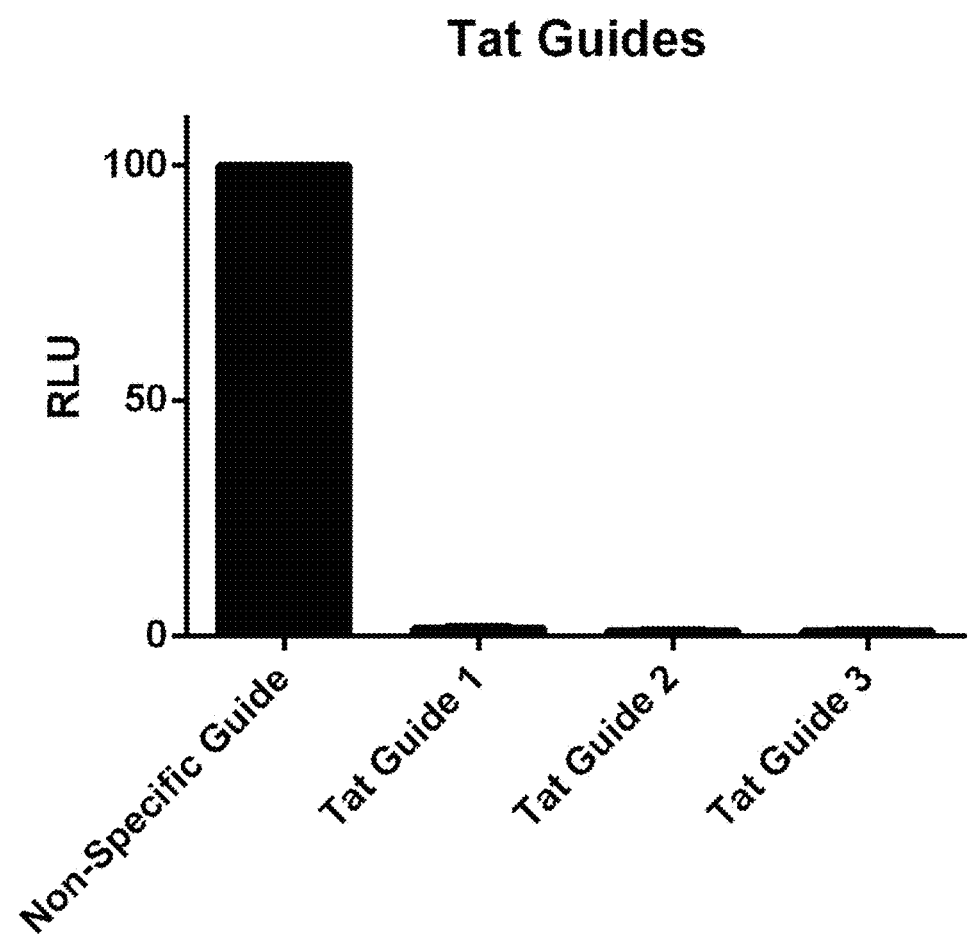
FIG. 18 is a set of graphs showing the relative luciferase expression of cells transfected with a HIV-1 luciferase reporter construct. Cells were transfected with Spy Cas9 and an sgRNA specific for conserved regions of the HIV-1 tat gene (FIG. 18A) or TAR element (FIG. 18B), or a non-specific sgRNA, as well as plasmids encoding the HIV-1 receptors CD4 and CXCR4. 72 hours later the transfected 293T cells were infected with a stock of HIV-1 strain NL4-3 encoding FLuc in place of the viral nef gene and relative luciferase expression measured.
Figure 18B:
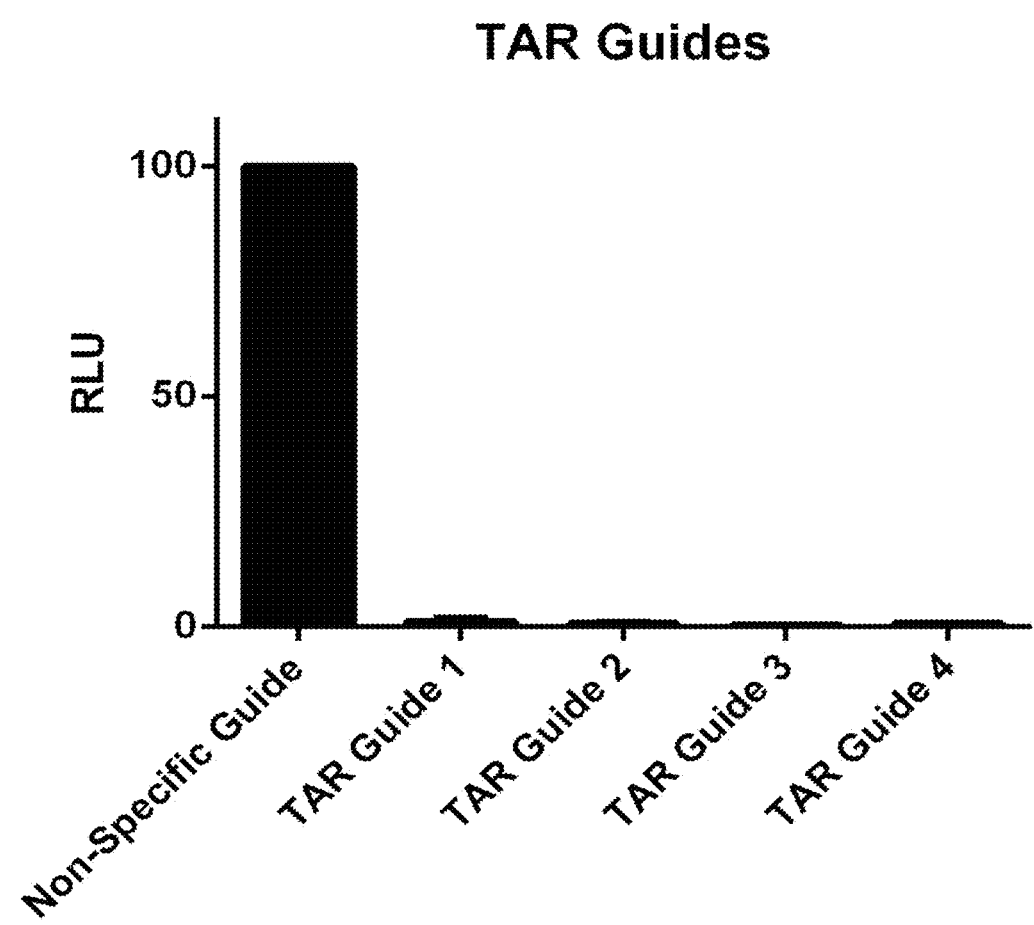

To determine whether the HIV-1 virus DNA intermediate can be targeted by the CRISPR/Cas9 system, we designed sgRNAs specific for HIV-1 Tat (SEQ ID NO: 33-35) and TAR (SEQ ID NO: 30-32), which are highly conserved in this virus. 293T cells were transfected with a plasmid encoding Spy Cas9 and an sgRNA specific for conserved regions of the HIV-1 tat gene or TAR element, or a non-specific sgRNA, as well as plasmids encoding the HIV-1 receptors CD4 and CXCR4. 72 hours later the transfected 293T cells were infected with a stock of HIV-1 strain NL4-3 encoding the FLuc gene in lieu of the viral nef gene. 24 hrs post-infection cells were harvested and assayed for FLuc activity. The results are shown in FIG. 18A (Tat) and FIG. 18B (TAR). HIV-1 was shown to be a good target for the CRISPR/Cas9 system with infection being essentially entirely blocked when Cas9 and an HIV-1 specific sgRNA were expressed.

REFERENCES

1. Mighty K K, Laimins L A. 2014. The role of human papillomaviruses in oncogenesis. Recent Results Cancer Res 193:135-148.
2. McLaughlin-Drubin M E, Münger K. 2009. Oncogenic activities of human papillomaviruses. Virus Res 143:195-208.
3. Howley P M. 1991. Role of the human papillomaviruses in human cancer. Cancer Res 51:5019s-5022s.
4. DeFilippis R A, Goodwin E C, Wu L, DiMaio D. 2003. Endogenous human papillomavirus E6 and E7 proteins differentially regulate proliferation, senescence, and apoptosis in HeLa cervical carcinoma cells. J Virol 77:1551-1563.
5. Goodwin E C, DiMaio D. 2000. Repression of human papillomavirus oncogenes in HeLa cervical carcinoma cells causes the orderly reactivation of dormant tumor suppressor pathways. Proc Natl Acad Sci USA 97:12513-12518.
6. Scheffner M, Werness B A, Huibregtse J M, Levine A J, Howley P M. 1990. The E6 oncoprotein encoded by human papillomavirus types 16 and 18 promotes the degradation of p53. Cell 63:1129-1136.
7. Hall A H, Alexander K A. 2003. RNA interference of human papillomavirus type 18 E6 and E7 induces senescence in HeLa cells. J Virol 77:6066-6069.
8. Cong L, Ran F A, Cox D, Lin S, Barretto R, Habib N, Hsu P D, Wu X, Jiang W, Marraffini L A, Zhang F. 2013. Multiplex genome engineering using CRISPR/Cas systems. Science 339:819-823.
9. Mali P, Yang L, Esvelt K M, Aach J, Guell M, DiCarlo J E, Norville J E, Church G M. 2013. RNA-guided human genome engineering via Cas9. Science 339:823-826.
10. Shalem O, Sanjana N E, Hartenian E, Shi X, Scott D A, Mikkelsen T S, Heckl D, Ebert B L, Root D E, Doench J G, Zhang F. 2014. Genome-scale CRISPR-Cas9 knockout screening in human cells. Science 343:84-87.
11. Ran F A, Hsu P D, Lin C Y, Gootenberg J S, Konermann S, Trevino A E, Scott D A, Inoue A, Matoba S, Zhang Y, Zhang F. 2013. Double nicking by RNA-guided CRISPR Cas9 for enhanced genome editing specificity. Cell 154: 1380-1389.
12. Malim M H, Bohnlein S, Hauber J, Cullen B R. 1989. Functional dissection of the HIV-1 Rev trans-activator—derivation of a trans-dominant repressor of Rev function. Cell 58:205-214.
13. Zhang J, Jima D D, Jacobs C, Fischer R, Gottwein E, Huang G, Lugar P L, Lagoo A S, Rizzieri D A, Friedman D R, Weinberg J B, Lipsky P E, Dave S S. 2009. Patterns of microRNA expression characterize stages of human B-cell differentiation. Blood 113:4586-4594.
14. Seedorf K, Oltersdorf T, Krammer G, Rowekamp W. 1987. Identification of early proteins of the human papilloma viruses type 16 (HPV 16) and type 18 (HPV 18) in cervical carcinoma cells. EMBO J 6:139-144.

Chen, Y., Sze, J., He, M. L., 2004. HBV cccDNA in patients' sera as an indicator for HBV reactivation and an early signal of liver damage. World J Gastroenterol 10, 82-85.

Gripon, P., Rumin, S., Urban, S., Le Seyec, J., Glaise, D., Cannie, I., Guyomard, C., Lucas, J., Trepo, C., Guguen-Guillouzo, C., 2002. Infection of a human hepatoma cell line by hepatitis B virus. Proc Natl Acad Sci USA 99, 15655-15660.

Hantz, O., Parent, R., Durantel, D., Gripon, P., Guguen-Guillouzo, C., Zoulim, F., 2009. Persistence of the hepatitis B virus covalently closed circular DNA in HepaRG human hepatocyte-like cells. J Gen Virol 90, 127-135.

King, R. W., Ladner, S. K., 2000. Hep AD38 Assay: A High-Throughput, Cell-Based Screen for the Evaluation of Compounds Against Hepatitis B Virus. Methods Mol Med 24, 43-50.

Ladner, S. K., Otto, M. J., Barker, C. S., Zaifert, K., Wang, G. H., Guo, J. T., Seeger, C., King, R. W., 1997. Inducible expression of human hepatitis B virus (HBV) in stably transfected hepatoblastoma cells: a novel system for screening potential inhibitors of HBV replication. Antimicrob Agents Chemother 41, 1715-1720.

Liu, M. C., Yu, M., Zhang, N. L., Gong, W. B., Wang, Y., Piao, W. H., Wang, Q. H., Wang, G. Q., 2004. Dynamic analysis of hepatitis B virus DNA and its antigens in 2.2.15 cells. J Viral Hepat 11, 124-129.

Lucifora, J., Xia, Y., Reisinger, F., Zhang, K., Stadler, D., Cheng, X., Sprinzl, M. F., Koppensteiner, H., Makowska, Z., Volz, T., Remouchamps, C., Chou, W. M., Thasler, W. E., Huser, N., Durantel, D., Liang, T. J., Munk, C., Heim, M. H., Browning, J. L., Dejardin, E., Dandri, M., Schindler, M., Heikenwalder, M., Protzer, U., 2014. Specific and nonhepatotoxic degradation of nuclear hepatitis B virus cccDNA. Science 343, 1221-1228.

Mali, P., Yang, L., Esvelt, K. M., Aach, J., Guell, M., DiCarlo, J. E., Norville, J. E., Church, G. M., 2013. RNA-guided human genome engineering via Cas9. Science 339, 823-826.

Malmstrom, S., Larsson, S. B., Hannoun, C., Lindh, M., 2012. Hepatitis B viral DNA decline at loss of HBeAg is mainly explained by reduced cccDNA load-down-regulated transcription of PgRNA has limited impact. PLoS One 7, e36349.

Pas, S. D., Fries, E., De Man, R. A., Osterhaus, A. D., Niesters, H. G., 2000. Development of a quantitative real-time detection assay for hepatitis B virus DNA and comparison with two commercial assays. J Clin Microbiol 38, 2897-2901.

Sells, M. A., Chen, M. L., Acs, G., 1987. Production of hepatitis B virus particles in Hep G2 cells transfected with cloned hepatitis B virus DNA. Proc Natl Acad Sci USA 84, 1005-1009.

Shalem, O., Sanjana, N. E., Hartenian, E., Shi, X., Scott, D. A., Mikkelsen, T. S., Heckl, D., Ebert, B. L., Root, D. E., Doench, J. G., Zhang, F., 2014. Genome-scale CRISPR-Cas9 knockout screening in human cells. Science 343, 84-87.

Stuyver, L. J., Lostia, S., Adams, M., Mathew, J. S., Pai, B. S., Grier, J., Tharnish, P. M., Choi, Y., Chong, Y., Choo, H., Chu, C. K., Otto, M. J., Schinazi, R. F., 2002. Antiviral activities and cellular toxicities of modified 2',3'-dideoxy-2',3'-didehydrocytidine analogues. Antimicrob Agents Chemother 46, 3854-3860.

Bowden, R J, Simas J P, Davis A J, Efstathiou S. 1997. Murine gammaherpesvirus 68 encodes tRNA-like sequences which are expressed during latency. J Gen Virol. 78 (7):1675-87.

We claim:

1. A recombinant Sau Cas9 construct comprising a promoter operably connected to a polynucleotide encoding a recombinant Sau Cas9 polypeptide, the polynucleotide comprising SEQ ID NO: 55.

2. The recombinant Sau Cas9 construct of claim 1, further comprising at least one of a poly (A) addition site, an intron and a nuclear localization signal.

3. The recombinant Sau Cas9 construct of claim 1, wherein the promoter is an RNA Polymerase II dependent promoter/enhancer selected from the group consisting of EFS, hCMV, mCMV, CBA, hSynapsin, HSV TK, SV40 early and LSP.

4. The recombinant Sau Cas9 construct of claim 1, having SEQ ID NO: 58.

5. A kit comprising the recombinant Sau Cas9 construct of claim 1.

6. A kit comprising a recombinant construct comprising a recombinant Sau Cas9 construct comprising a promoter operably connected to a polynucleotide encoding a recombinant Sau Cas9 polypeptide, the polynucleotide comprising SEQ ID NO: 55, the recombinant construct comprising a first polynucleotide encoding a mammalian or viral tRNA operably connected to a second polynucleotide encoding at least a second portion of a single guide RNA capable of interacting with a Cas9 polypeptide, wherein the mammalian or viral tRNA is selected from the group consisting of a Gln tRNA, Pro tRNA, Gly tRNA, Asn tRNA, Cys tRNA, Glu tRNA, and a mouse gamma herpesvirus-68 (MHV68) tRNA.

7. The recombinant Sau Cas9 construct of claim 1, further comprising an affinity tag.

8. The recombinant Sau Cas9 construct of claim 1, further comprising a second promoter operably connected to a second polynucleotide encoding a single guide RNA.

9. The recombinant Sau Cas9 construct of claim 8, wherein the single guide RNA comprises a first portion complementary to a strand of a target sequence of a DNA virus and a second portion capable of interacting with the Cas9 polypeptide.

10. The recombinant Sau Cas9 construct of claim 9, wherein the DNA virus is classified in a family selected from the group consisting of hepadnaviridae, herpesviridae, papillomaviridae, and retroviridae.

11. The recombinant Sau Cas9 construct of claim 10, wherein the DNA virus is a herpesviridae selected from the group consisting of herpes simplex virus type 1 (HSV-1), herpes simplex virus type 2 (HSV-2), Epstein Barr Virus (EBV), human cytomegalovirus (hCMV), Varicella zoster virus (VZV), and Kaposi's sarcoma associated herpesvirus (KSHV).

12. The recombinant Sau Cas9 construct of claim 10, wherein the DNA virus is hepatitis B virus (HBV).

13. The recombinant Sau Cas9 construct of claim 10, wherein the DNA virus is human immunodeficiency virus (HIV-1).

14. The recombinant Sau Cas9 construct of claim 9, wherein the target sequence is selected from a gene encoding a reverse transcriptase or a surface antigen.

15. The recombinant Sau Cas9 construct of claim 8, wherein the second promoter is a RNA Polymerase III promoter selected from the group consisting of a U6 promoter, a Gln tRNA, Pro tRNA, Gly tRNA, Asn tRNA, Cys tRNA, Glu tRNA, a mouse gamma herpesvirus-68 (MHV68) tRNA or any mammalian tRNA.

16. A viral vector comprising the recombinant Sau Cas9 construct of claim 1.

17. The viral vector of claim 16, wherein the viral vector is selected from the group consisting of a retrovirus, a lentivirus, an adenovirus or an adeno-associated virus.

18. The viral vector of claim 17, wherein the viral vector is an adeno-associated virus (AAV).

19. A viral vector comprising the recombinant Sau Cas9 construct of claim 8.

20. The viral vector of claim 19, wherein the viral vector is selected from the group consisting of a retrovirus, a lentivirus, an adenovirus or an adeno-associated virus.

21. The viral vector of claim 20, wherein the viral vector is an adeno-associated virus (AAV).

* * * * *

SEQUENCE LISTING

```
<160> NUMBER OF SEQ ID NOS: 68

<210> SEQ ID NO 1
<211> LENGTH: 20
<212> TYPE: DNA
<213> ORGANISM: Hepatitis B Virus
<220> FEATURE:
<221> NAME/KEY: misc_feature
<222> LOCATION: (1)..(20)
<223> OTHER INFORMATION: Reverse Transcriptase YMDD

<400> SEQUENCE: 1
gttcagttat atggatgatg                                          20

<210> SEQ ID NO 2
<211> LENGTH: 20
<212> TYPE: DNA
<213> ORGANISM: Hepatitis B Virus
<220> FEATURE:
<221> NAME/KEY: misc_feature
<222> LOCATION: (1)..(20)
<223> OTHER INFORMATION: Surface Antigen

<400> SEQUENCE: 2
gcctgtcctc caacttgtcc                                          20

<210> SEQ ID NO 3
<211> LENGTH: 20
<212> TYPE: DNA
<213> ORGANISM: Hepatitis B Virus
<220> FEATURE:
<221> NAME/KEY: misc_feature
<222> LOCATION: (1)..(20)
<223> OTHER INFORMATION: Core

<400> SEQUENCE: 3
gtaccgcctc agctctgtat                                          20

<210> SEQ ID NO 4
<211> LENGTH: 24
<212> TYPE: DNA
<213> ORGANISM: Hepatitis B Virus
<220> FEATURE:
<221> NAME/KEY: misc_feature
<222> LOCATION: (1)..(24)
<223> OTHER INFORMATION: Reverse Transcriptase sgRNA-1

<400> SEQUENCE: 4
gctgggcttt cggaaaattc ctat                                     24

<210> SEQ ID NO 5
<211> LENGTH: 24
```

```
<212> TYPE: DNA
<213> ORGANISM: Hepatitis B Virus
<220> FEATURE:
<221> NAME/KEY: misc_feature
<222> LOCATION: (1)..(24)
<223> OTHER INFORMATION: Surface Antigen sgRNA

<400> SEQUENCE: 5
ggctgaacat ggagaacatc acat                                        24

<210> SEQ ID NO 6
<211> LENGTH: 24
<212> TYPE: DNA
<213> ORGANISM: Hepatitis B Virus
<220> FEATURE:
<221> NAME/KEY: misc_feature
<222> LOCATION: (1)..(24)
<223> OTHER INFORMATION: Core

<400> SEQUENCE: 6
gttataaaga atttggagct actg                                        24

<210> SEQ ID NO 7
<211> LENGTH: 24
<212> TYPE: DNA
<213> ORGANISM: Hepatitis B Virus
<220> FEATURE:
<221> NAME/KEY: misc_feature
<222> LOCATION: (1)..(24)
<223> OTHER INFORMATION: Reverse Transcriptase sgRNA-2

<400> SEQUENCE: 7
gtgagtgatt ggaggttggg gact                                        24

<210> SEQ ID NO 8
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: E6 sgRNA 1

<400> SEQUENCE: 8
ggcgctttga ggatccaaca                                             20

<210> SEQ ID NO 9
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: E6 sgRNA 2

<400> SEQUENCE: 9
gaagctacct gatctgtgca                                             20

<210> SEQ ID NO 10
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: E7 sgRNA 1

<400> SEQUENCE: 10
```
ggagcaatta agcgactcag                                               20

<210> SEQ ID NO 11
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: E7 sgRNA 2

<400> SEQUENCE: 11
gaagaaaacg atgaaataga                                               20

<210> SEQ ID NO 12
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: HPV-16 E6t1

<400> SEQUENCE: 12
gcaacagtta ctgcgacgtg                                               20

<210> SEQ ID NO 13
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: HPV-16 E7t1

<400> SEQUENCE: 13
gccagctgga caagcagaac                                               20

<210> SEQ ID NO 14
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: E6

<400> SEQUENCE: 14
gagcttgtag ggtcgccgtg                                               20

<210> SEQ ID NO 15
<211> LENGTH: 20
<212> TYPE: DNA
<213> ORGANISM: Human Papilloma Virus-18
<220> FEATURE:
<221> NAME/KEY: misc_feature
<222> LOCATION: (1)..(20)
<223> OTHER INFORMATION: E7

<400> SEQUENCE: 15
gcgtgacata aaaggtcaac                                               20

<210> SEQ ID NO 16
<211> LENGTH: 24
<212> TYPE: DNA
<213> ORGANISM: Herpes Simplex Virus-1
<220> FEATURE:
<221> NAME/KEY: misc_feature

```
<222> LOCATION: (1)..(24)
<223> OTHER INFORMATION: ICP0 sgRNA 1

<400> SEQUENCE: 16
ggtccgtgct gtccgcctcg gagg                                              24

<210> SEQ ID NO 17
<211> LENGTH: 24
<212> TYPE: DNA
<213> ORGANISM: Herpes Simplex Virus-1
<220> FEATURE:
<221> NAME/KEY: misc_feature
<222> LOCATION: (1)..(24)
<223> OTHER INFORMATION: ICP0 sgRNA 2

<400> SEQUENCE: 17
gaattgcatc caggttttca tgca                                              24

<210> SEQ ID NO 18
<211> LENGTH: 24
<212> TYPE: DNA
<213> ORGANISM: Herpes Simplex Virus-1
<220> FEATURE:
<221> NAME/KEY: misc_feature
<222> LOCATION: (1)..(24)
<223> OTHER INFORMATION: ICP4 sgRNA 1

<400> SEQUENCE: 18
ggtgggggtg gtcggggtcg tggt                                              24

<210> SEQ ID NO 19
<211> LENGTH: 24
<212> TYPE: DNA
<213> ORGANISM: Herpes Simplex Virus-1
<220> FEATURE:
<221> NAME/KEY: misc_feature
<222> LOCATION: (1)..(24)
<223> OTHER INFORMATION: ICP4 sgRNA 2

<400> SEQUENCE: 19
cgtgggggtg gtcggggtcg tggt                                              24

<210> SEQ ID NO 20
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: Family of Repeats (FR)

<400> SEQUENCE: 20
gggaggtggc ggcatatgca                                                   20

<210> SEQ ID NO 21
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: Direct Symmetry (DS)

<400> SEQUENCE: 21
ttggtgtaag agcttcagcc                                                   20

<210> SEQ ID NO 22
```

```
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: EBNA1 sgRNA-1

<400> SEQUENCE: 22
gtggacctca aagaagaggg                                                     20

<210> SEQ ID NO 23
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: EBNA1 sgRNA-2

<400> SEQUENCE: 23
agatgagggt gaggaagggc                                                     20

<210> SEQ ID NO 24
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: Qp sgRNA-1

<400> SEQUENCE: 24
agaaattggg tgaccactga                                                     20

<210> SEQ ID NO 25
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: Qp sgRNA-2

<400> SEQUENCE: 25
ttgtctggtc gctagatggc                                                     20

<210> SEQ ID NO 26
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: Latent Membrane Protein-1 sgRNA-1

<400> SEQUENCE: 26
gcttagctga actgggccgt                                                     20

<210> SEQ ID NO 27
<211> LENGTH: 20
<212> TYPE: DNA
<213> ORGANISM: Epstein-Barr Virus
<220> FEATURE:
<221> NAME/KEY: misc_feature
<222> LOCATION: (1)..(20)
<223> OTHER INFORMATION: Latent Membrane Protein-1 sgRNA-2

<400> SEQUENCE: 27
```
cttctgaaga taaagatgat                                                    20

<210> SEQ ID NO 28
<211> LENGTH: 25
<212> TYPE: DNA
<213> ORGANISM: Artificial Sequence
<220> FEATURE:
<223> OTHER INFORMATION: Synthetic: Bacterial targets used in tRNA
      analysis, P9 (Nme)

<400> SEQUENCE: 28
gacatcctca gatttagtat tcaga                                              25

<210> SEQ ID NO 29
<211> LENGTH: 25
<212> TYPE: DNA
<213> ORGANISM: Artificial Sequence
<220> FEATURE:
<223> OTHER INFORMATION: Synthetic: Bacterial targets used in tRNA
      analysis, P25 (Nme)

<400> SEQUENCE: 29
gtcatgcgcg gcgcattacc tttac                                              25

<210> SEQ ID NO 30
<211> LENGTH: 20
<212> TYPE: DNA
<213> ORGANISM: Artificial Sequence
<220> FEATURE:
<223> OTHER INFORMATION: Synthetic: HIV target sequence, TAR sgRNA 1

<400> SEQUENCE: 30
ggttagacca gatctgagcc                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic: HIV target sequence, TAR sgRNA 2

<400> SEQUENCE: 31
gtctgagcct gggagctctc                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic: HIV target sequence, TAR sgRNA 3

<400> SEQUENCE: 32
ggagctccca ggctcagatc                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic: HIV target sequence, TAT sgRNAs 1

<400> SEQUENCE: 33
gtagagccct ggaagcatcc                                                    20

<210> SEQ ID NO 34

```
<211> LENGTH: 20
<212> TYPE: DNA
<213> ORGANISM: Artificial Sequence
<220> FEATURE:
<223> OTHER INFORMATION: Synthetic: HIV target sequence, TAT sgRNA  2

<400> SEQUENCE: 34
gagatcctag actagagccc                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic: HIV target sequence, TAT sgRNA  3

<400> SEQUENCE: 35
ggctctagtc taggatctac                                                   20

<210> SEQ ID NO 36
<211> LENGTH: 99
<212> TYPE: DNA
<213> ORGANISM: Artificial Sequence
<220> FEATURE:
<223> OTHER INFORMATION: Synthetic: Spy sgRNA

<400> SEQUENCE: 36
gggtcttcga agacctgt tttagagcta gaaatagcaa gttaaaataa ggctagtccg         60
ttatcaactt gaaaaagtgg caccgagtcg gtgcttttt                              99

<210> SEQ ID NO 37
<211> LENGTH: 130
<212> TYPE: DNA
<213> ORGANISM: Artificial Sequence
<220> FEATURE:
<223> OTHER INFORMATION: Synthetic: Nme sgRNA

<400> SEQUENCE: 37
gggtcttcga ggtctcagtt gtagctccca acgaaatga gaaccgttgc tacaataagg        60
ccgtctgaaa agatgtgccg caacgctctg ccccttaaag cttctgcttt aaggggcatc     120
gtttattttt                                                            130

<210> SEQ ID NO 38
<211> LENGTH: 97
<212> TYPE: DNA
<213> ORGANISM: Artificial Sequence
<220> FEATURE:
<223> OTHER INFORMATION: Synthetic: Sau sgRNA

<400> SEQUENCE: 38
ggagacggac gtctccgttt tagtactctg gaaacagaat ctactaaaac aaggcaaaat       60
gccgtgttta tctcgtcaac ttgttggcga gattttt                                97

<210> SEQ ID NO 39
<211> LENGTH: 98
<212> TYPE: DNA
<213> ORGANISM: Artificial Sequence
<220> FEATURE:
<223> OTHER INFORMATION: Synthetic: Variable sgRNA-1

<400> SEQUENCE: 39
ggagacggac gtctccgttt tagtactctg gaaacagaat ctactaaaac aaggcaaaat       60
gccgtgttta tctcgtcaac ttgttggcga gatttttt                               98
```

<210> SEQ ID NO 40
<211> LENGTH: 100
<212> TYPE: DNA
<213> ORGANISM: Artificial Sequence
<220> FEATURE:
<223> OTHER INFORMATION: Synthetic: Variable sgRNA-2

<400> SEQUENCE: 40
gggtcttcga gaagacccgt tttagtactc tggaaacaga atctactaaa acaaggcaaa    60
atgccgtgtt tatctcgtca acttgttggc gagatttttt    100

<210> SEQ ID NO 41
<211> LENGTH: 72
<212> TYPE: DNA
<213> ORGANISM: Artificial Sequence
<220> FEATURE:
<223> OTHER INFORMATION: Synthetic: tRNA-99 (Gln)

<400> SEQUENCE: 41
ggttccatgg tgtaatggtt agcactctgg actctgaatc cagcgatccg agttcaaatc    60
tcggtggaac ct    72

<210> SEQ ID NO 42
<211> LENGTH: 71
<212> TYPE: DNA
<213> ORGANISM: Artificial Sequence
<220> FEATURE:
<223> OTHER INFORMATION: Synthetic: tRNA-128 (Gly)

<400> SEQUENCE: 42
gcattggtgg ttcagtggta gaattctcgc ctgccacgcg ggaggcccgg gttcgattcc    60
cggccaatgc a    71

<210> SEQ ID NO 43
<211> LENGTH: 75
<212> TYPE: DNA
<213> ORGANISM: Artificial Sequence
<220> FEATURE:
<223> OTHER INFORMATION: Synthetic: tRNA-115 (Asn)

<400> SEQUENCE: 43
tgtctctgtg gcgcaatcgg ttagcgcgtt cggctgttaa ctgaaaggtt agtggttcga    60
gcccacccgg ggacg    75

<210> SEQ ID NO 44
<211> LENGTH: 72
<212> TYPE: DNA
<213> ORGANISM: Artificial Sequence
<220> FEATURE:
<223> OTHER INFORMATION: Synthetic: tRNA-7 (His)

<400> SEQUENCE: 44
gccgtgatcg tatagtggtt agtactctgc gttgtggccg cagcaacctc ggttcgaatc    60
cgagtcacgg ca    72

<210> SEQ ID NO 45
<211> LENGTH: 72
<212> TYPE: DNA
<213> ORGANISM: Artificial Sequence
<220> FEATURE:
<223> OTHER INFORMATION: Synthetic: tRNA-49 (Gln-2)

```
<400> SEQUENCE: 45
ggttccatgg tgtaatggtt agcactctgg actctgaatc cagcgatccg agttcaaatc      60
tcggtggaac ct                                                         72

<210> SEQ ID NO 46
<211> LENGTH: 72
<212> TYPE: DNA
<213> ORGANISM: Artificial Sequence
<220> FEATURE:
<223> OTHER INFORMATION: Synthetic: tRNA-87 (Glu)

<400> SEQUENCE: 46
tccctggtgg tctagtggtt aggattcggc gctctcaccg ccgcggcccg ggttcgattc      60
ccggtcaggg aa                                                         72

<210> SEQ ID NO 47
<211> LENGTH: 72
<212> TYPE: DNA
<213> ORGANISM: Artificial Sequence
<220> FEATURE:
<223> OTHER INFORMATION: Synthetic: tRNA-2 (Pro)

<400> SEQUENCE: 47
ggctcgttgg tctaggggta tgattctcgc ttagggtgcg agaggtcccg ggttcaaatc      60
ccggacgagc cc                                                         72

<210> SEQ ID NO 48
<211> LENGTH: 72
<212> TYPE: DNA
<213> ORGANISM: Artificial Sequence
<220> FEATURE:
<223> OTHER INFORMATION: Synthetic: tRNA-25 (Cys)

<400> SEQUENCE: 48
gggggtatag ctcaggggta gagcatttga ctgcagatca agaggtcccc agttcaaatc      60
tgggtgcccc ct                                                         72

<210> SEQ ID NO 49
<211> LENGTH: 73
<212> TYPE: DNA
<213> ORGANISM: Artificial Sequence
<220> FEATURE:
<223> OTHER INFORMATION: Synthetic: tRNA-5 (Tyr)

<400> SEQUENCE: 49
gtcagtgttg cacaacggtt aagtgaagag gctgtaaacc cagactggat gggttcaatt      60
cccatctctg ccg                                                        73

<210> SEQ ID NO 50
<211> LENGTH: 72
<212> TYPE: DNA
<213> ORGANISM: Artificial Sequence
<220> FEATURE:
<223> OTHER INFORMATION: Synthetic: MHV tRNA-5

<400> SEQUENCE: 50
gccagggtag ctcaattggt agagcatcag gctagtatcc tgtcggttcc ggttcaagtc      60
cgggccctgg tt                                                         72

<210> SEQ ID NO 51
<211> LENGTH: 255
```

<212> TYPE: DNA
<213> ORGANISM: Artificial Sequence
<220> FEATURE:
<223> OTHER INFORMATION: Synthetic: U6 Promoter

<400> SEQUENCE: 51

```
tctagagagg gcctatttcc catgattcct tcatatttgc atatacgata caaggctgtt    60
agagagataa ttggaattaa tttgactgta aacacaaaga tattagtaca aaatacgtga   120
cgtagaaagt aataatttct tgggtagttt gcagttttaa aattatgttt taaaatggac   180
tatcatatgc ttaccgtaac ttgaaagtat ttcgatttct tggctttata tcttgtgg    240
aaaggacgaa acacc                                                    255
```

<210> SEQ ID NO 52
<211> LENGTH: 298
<212> TYPE: DNA
<213> ORGANISM: Artificial Sequence
<220> FEATURE:
<223> OTHER INFORMATION: Synthetic: EFS Promoter

<400> SEQUENCE: 52

```
ctcgaggtcg gaggatccac aaaggctagc cggtctatgc attaggtctt gaaaggagtg    60
ggaattggct ccggtgcccg tcagtgggca gagcgcacat cgcccacagt ccccgagaag   120
ttgggggag gggtcggcaa ttgatccggt gcctagagaa ggtggcgcgg ggtaaactgg   180
gaaagtgatg tcgtgtactg gctccgcctt tttcccgagg gtgggggaga accgtatata   240
agtgcagtag tcgccgtgaa cgttctttt cgcaacgggt ttgccgccag aacacagg     298
```

<210> SEQ ID NO 53
<211> LENGTH: 185
<212> TYPE: DNA
<213> ORGANISM: Rattus sp.
<220> FEATURE:
<221> NAME/KEY: misc_feature
<222> LOCATION: (1)..(185)
<223> OTHER INFORMATION: Rat Preproinsulin II Intron

<400> SEQUENCE: 53

```
aagcttggta agtgaccagc tacagtcgga aaccatcagc aagcaggtat gtactctcca    60
gggtgggcct ggcttcccca gtcaagactc cagggatttg agggacgctg tgggctcttc   120
tcttacatgt accttttgct agcctcaacc ctgactatct tccaggtcat tgttccaacg   180
ccacc                                                               185
```

<210> SEQ ID NO 54
<211> LENGTH: 66
<212> TYPE: DNA
<213> ORGANISM: Artificial Sequence
<220> FEATURE:
<223> OTHER INFORMATION: Synthetic: NLS-1x flag

<400> SEQUENCE: 54

```
atggcacttg aagctcccaa gaagaagcgg aaagtgggaa gcgattacaa ggatgacgat    60
gacaag                                                               66
```

<210> SEQ ID NO 55
<211> LENGTH: 3159
<212> TYPE: DNA
<213> ORGANISM: S. aureus
<220> FEATURE:
<221> NAME/KEY: misc_feature
<222> LOCATION: (1)..(3159)

<223> OTHER INFORMATION: S. aureus Cas9

<400> SEQUENCE: 55

```
aagaggaatt acatcctcgg actggacatc ggcattacca gcgtcggcta cggcatcatc      60
gattacgaga caagggacgt gattgacgct ggcgtcaggc tgttcaagga ggccaacgtg     120
gagaataatg agggcaggag aagcaagagg ggcgccagga ggctgaagag gaggagaagg     180
cacagaatcc agagggtcaa gaagctcctg ttcgactaca acctgctgac cgaccatagc     240
gagctgagcg gcattaaccc ctacgaggct agggtcaaag gcctctccca gaaactgtcc     300
gaggaggagt ttagcgctgc tctcctgcac ctggccaaga ggaggggagt gcacaatgtg     360
aacgaggtcg aagaggacac cggcaatgag ctcagcacca aggagcagat tagcagaaac     420
agcaaagccc tggaggaaaa atatgtcgcc gagctacagc tggagagact caagaaggat     480
ggcgaggtca gaggctccat taacaggttc aagacctccg actacgtgaa agaagccaag     540
cagctgctga aggtgcaaaa ggcctatcat cagctggacc agagcttcat tgatacctat     600
atcgacctgc tcgaaaccag gagaacctac tatgagggcc ctggagaagg aagccccttc     660
ggatggaaag acattaagga gtggtacgaa atgctgatgg acactgcac ctacttcccc      720
gaggagctga ggagcgtgaa atatgcctac aacgccgatc tctacaacgc cctgaacgac     780
ctgaacaatc tcgtgattac aagggatgag aacgaaaagc tggaatatta cgaaaaattt     840
cagatcattg aaaacgtgtt taagcaaaag aagaagccca ccctgaagca gattgccaag     900
gagatcctgg tgaacgaaga ggacattaaa ggctacagag tgacctccac aggcaaaccc     960
gaatttacca atctgaaggt gtatcacgat atcaaagata tcacagctag aaaggagatc    1020
atcgagaatg ctgagctgct cgaccaaatc gccaagattc tcaccatcta ccagagcagc    1080
gaggacatcc aggaagaact gacaaacctg aactccgagc tcacccagga gaaaatcgag    1140
cagatttcca acctgaaagg ctacaccggc acccacaacc tgtccctgaa ggccatcaac    1200
ctgatcctcg atgaactctg gcacaccaat gacaatcaaa tcgctatctt caacagactg    1260
aagctcgtgc ccaagaaagt ggacctgagc cagcagaagg aaatccctac aaccctcgtg    1320
gacgatttca tcctcagccc cgtcgtgaag aggagcttca tccagtccat caaggtgatt    1380
aacgctatca tcaagaagta tggcctcccc aacgacatca tcatcgagct cgctagggaa    1440
aaaaactcca aggatgctca gaaaatgatc aacgagatgc agaaaaggaa cagacaaacc    1500
aacgaaagga ttgaggagat tatcaggacc accggcaagg agaatgctaa gtatctgatt    1560
gaaaaaatta aactccacga tatgcaggag ggcaagtgtc tctatagcct ggaagccatc    1620
cctctggagg atctcctgaa caatcctttt aactacgaag tggaccacat tatccccagg    1680
agcgtgtcct tcgataactc ctttaataat aaggtcctgg tcaaacagga ggagaactcc    1740
aagaagggaa acaggacacc cttccaatat ctctccagca gcgactccaa aataagctac    1800
gaaacctta aaaacacat tctgaacctg gccaagggca aggcaggat cagcaaaacc       1860
aaaaaggaat acctcctgga ggagagagac atcaacaggt tctccgtgca gaaagacttc    1920
atcaacagga acctggtgga caccaggtat gccaccaggg gcctgatgaa cctcctgagg    1980
tcctatttta gagtcaataa tctcgacgtg aaagtcaaat ccattaatgg cggctttacc    2040
agcttcctga ggagaaaatg gaagttcaag aaggagagaa acaaaggcta caaacaccac    2100
gccgaagatg ccctcatcat tgctaacgcc gacttcatct ttaaggagtg gaagaagctc    2160
gataaggcca agaagtcat ggagaatcaa atgttcgagg agaaacaagc cgaatccatg     2220
cccgagattg aaacggagca agagtacaag gaaatattca tcaccccctca ccagatcaaa    2280
```

```
cacatcaagg acttcaaaga ctacaaatat agccatagag tcgataagaa gcccaacagg    2340
gagctgatca acgacacact ctattccacc agaaaggatg ataagggcaa caccctgatt    2400
gtgaacaacc tgaacggcct ctacgataag gataacgaca agctgaagaa gctgattaac    2460
aagagccccg agaaactgct catgtaccac cacgaccccc aaacatacca gaaactgaag    2520
ctgatcatgg aacagtatgg cgacgagaaa accccctgt ataagtacta tgaagaaacc    2580
ggcaactacc tcaccaagta cagcaaaaag gataacggac ccgtgatcaa aaagattaag    2640
tattacggca ataagctgaa tgcccacctc gatatcaccg atgattaccc caactccaga    2700
aataaagtcg tgaaactgtc cctgaaacct tacaggtttg acgtgtacct ggacaatggc    2760
gtgtacaagt tcgtgaccgt gaagaacctc gacgtgatta agaaggagaa ttactatgag    2820
gtcaacagca atgctatga ggaagccaag aaactgaaga gatttccaa tcaggccgag    2880 ttcatcgcca gcttttataa caacgacctg attaagatca tggcgaact gtatagggtg    2940 atcggcgtca caacgacct cctgaacagg attgaggtca atatgatcga tattacctac    3000
agagagtacc tcgaaaacat gaatgacaag aggcccccca ggattatcaa aaccatcgcc    3060
agcaagaccc agagcattaa gaaatacagc accgacatcc tcggcaacct gtacgaggtc    3120
aagtccaaaa agcaccccca gattatcaaa aagggatga                          3159
```

<210> SEQ ID NO 56
<211> LENGTH: 56
<212> TYPE: DNA
<213> ORGANISM: Artificial Sequence
<220> FEATURE:
<223> OTHER INFORMATION: Synthetic: Synthetic Poly (A)

<400> SEQUENCE: 56

```
gtcgacaata aaatatcttt attttcatta catctgtgtg ttggtttttt gtgtgt    56
```

<210> SEQ ID NO 57
<211> LENGTH: 1074
<212> TYPE: PRT
<213> ORGANISM: Artificial Sequence
<220> FEATURE:
<223> OTHER INFORMATION: Synthetic: NLS-Flag-Sau Cas9 Protein

<400> SEQUENCE: 57

```
Met Ala Leu Glu Ala Pro Lys Lys Lys Arg Lys Val Gly Ser Asp Tyr
1               5                   10                  15

Lys Asp Asp Asp Asp Lys Lys Arg Asn Tyr Ile Leu Gly Leu Asp Ile
            20                  25                  30

Gly Ile Thr Ser Val Gly Tyr Gly Ile Ile Asp Tyr Glu Thr Arg Asp
        35                  40                  45

Val Ile Asp Ala Gly Val Arg Leu Phe Lys Glu Ala Asn Val Glu Asn
    50                  55                  60

Asn Glu Gly Arg Arg Ser Lys Arg Gly Ala Arg Arg Leu Lys Arg Arg
65                  70                  75                  80

Arg Arg His Arg Ile Gln Arg Val Lys Lys Leu Leu Phe Asp Tyr Asn
                85                  90                  95

Leu Leu Thr Asp His Ser Glu Leu Ser Gly Ile Asn Pro Tyr Glu Ala
            100                 105                 110

Arg Val Lys Gly Leu Ser Gln Lys Leu Ser Glu Glu Phe Ser Ala
        115                 120                 125

Ala Leu Leu His Leu Ala Lys Arg Arg Gly Val His Asn Val Asn Glu
    130                 135                 140
```

Val Glu Glu Asp Thr Gly Asn Glu Leu Ser Thr Lys Glu Gln Ile Ser
145                 150                 155                 160

Arg Asn Ser Lys Ala Leu Glu Glu Lys Tyr Val Ala Glu Leu Gln Leu
            165                 170                 175

Glu Arg Leu Lys Lys Asp Gly Glu Val Arg Gly Ser Ile Asn Arg Phe
        180                 185                 190

Lys Thr Ser Asp Tyr Val Lys Glu Ala Lys Gln Leu Leu Lys Val Gln
    195                 200                 205

Lys Ala Tyr His Gln Leu Asp Gln Ser Phe Ile Asp Thr Tyr Ile Asp
210                 215                 220

Leu Leu Glu Thr Arg Arg Thr Tyr Tyr Glu Gly Pro Gly Glu Gly Ser
225                 230                 235                 240

Pro Phe Gly Trp Lys Asp Ile Lys Glu Trp Tyr Glu Met Leu Met Gly
            245                 250                 255

His Cys Thr Tyr Phe Pro Glu Glu Leu Arg Ser Val Lys Tyr Ala Tyr
        260                 265                 270

Asn Ala Asp Leu Tyr Asn Ala Leu Asn Asp Leu Asn Asn Leu Val Ile
    275                 280                 285

Thr Arg Asp Glu Asn Glu Lys Leu Glu Tyr Tyr Glu Lys Phe Gln Ile
290                 295                 300

Ile Glu Asn Val Phe Lys Gln Lys Lys Pro Thr Leu Lys Gln Ile
305                 310                 315                 320

Ala Lys Glu Ile Leu Val Asn Glu Glu Asp Ile Lys Gly Tyr Arg Val
            325                 330                 335

Thr Ser Thr Gly Lys Pro Glu Phe Thr Asn Leu Lys Val Tyr His Asp
        340                 345                 350

Ile Lys Asp Ile Thr Ala Arg Lys Glu Ile Ile Glu Asn Ala Glu Leu
    355                 360                 365

Leu Asp Gln Ile Ala Lys Ile Leu Thr Ile Tyr Gln Ser Ser Glu Asp
370                 375                 380

Ile Gln Glu Glu Leu Thr Asn Leu Asn Ser Glu Leu Thr Gln Glu Glu
385                 390                 395                 400

Ile Glu Gln Ile Ser Asn Leu Lys Gly Tyr Thr Gly Thr His Asn Leu
            405                 410                 415

Ser Leu Lys Ala Ile Asn Leu Ile Leu Asp Glu Leu Trp His Thr Asn
        420                 425                 430

Asp Asn Gln Ile Ala Ile Phe Asn Arg Leu Lys Leu Val Pro Lys Lys
    435                 440                 445

Val Asp Leu Ser Gln Gln Lys Glu Ile Pro Thr Thr Leu Val Asp Asp
450                 455                 460

Phe Ile Leu Ser Pro Val Val Lys Arg Ser Phe Ile Gln Ser Ile Lys
465                 470                 475                 480

Val Ile Asn Ala Ile Ile Lys Lys Tyr Gly Leu Pro Asn Asp Ile Ile
            485                 490                 495

Ile Glu Leu Ala Arg Glu Lys Asn Ser Lys Asp Ala Gln Lys Met Ile
        500                 505                 510

Asn Glu Met Gln Lys Arg Asn Arg Gln Thr Asn Glu Arg Ile Glu Glu
    515                 520                 525

Ile Ile Arg Thr Thr Gly Lys Glu Asn Ala Lys Tyr Leu Ile Glu Lys
530                 535                 540

Ile Lys Leu His Asp Met Gln Glu Gly Lys Cys Leu Tyr Ser Leu Glu
545                 550                 555                 560

```
Ala Ile Pro Leu Glu Asp Leu Leu Asn Asn Pro Phe Asn Tyr Glu Val
            565                 570                 575

Asp His Ile Ile Pro Arg Ser Val Ser Phe Asp Asn Ser Phe Asn Asn
        580                 585                 590

Lys Val Leu Val Lys Gln Glu Glu Asn Ser Lys Lys Gly Asn Arg Thr
            595                 600                 605

Pro Phe Gln Tyr Leu Ser Ser Ser Asp Ser Lys Ile Ser Tyr Glu Thr
    610                 615                 620

Phe Lys Lys His Ile Leu Asn Leu Ala Lys Gly Lys Gly Arg Ile Ser
625                 630                 635                 640

Lys Thr Lys Lys Glu Tyr Leu Leu Glu Glu Arg Asp Ile Asn Arg Phe
            645                 650                 655

Ser Val Gln Lys Asp Phe Ile Asn Arg Asn Leu Val Asp Thr Arg Tyr
            660                 665                 670

Ala Thr Arg Gly Leu Met Asn Leu Leu Arg Ser Tyr Phe Arg Val Asn
        675                 680                 685

Asn Leu Asp Val Lys Val Lys Ser Ile Asn Gly Gly Phe Thr Ser Phe
    690                 695                 700

Leu Arg Arg Lys Trp Lys Phe Lys Lys Glu Arg Asn Lys Gly Tyr Lys
705                 710                 715                 720

His His Ala Glu Asp Ala Leu Ile Ile Ala Asn Ala Asp Phe Ile Phe
            725                 730                 735

Lys Glu Trp Lys Lys Leu Asp Lys Ala Lys Lys Val Met Glu Asn Gln
            740                 745                 750

Met Phe Glu Glu Lys Gln Ala Glu Ser Met Pro Glu Ile Glu Thr Glu
        755                 760                 765

Gln Glu Tyr Lys Glu Ile Phe Ile Thr Pro His Gln Ile Lys His Ile
    770                 775                 780

Lys Asp Phe Lys Asp Tyr Lys Tyr Ser His Arg Val Asp Lys Lys Pro
785                 790                 795                 800

Asn Arg Glu Leu Ile Asn Asp Thr Leu Tyr Ser Thr Arg Lys Asp Asp
            805                 810                 815

Lys Gly Asn Thr Leu Ile Val Asn Asn Leu Asn Gly Leu Tyr Asp Lys
            820                 825                 830

Asp Asn Asp Lys Leu Lys Lys Leu Ile Asn Lys Ser Pro Glu Lys Leu
        835                 840                 845

Leu Met Tyr His His Asp Pro Gln Thr Tyr Gln Lys Leu Lys Leu Ile
    850                 855                 860

Met Glu Gln Tyr Gly Asp Glu Lys Asn Pro Leu Tyr Lys Tyr Tyr Glu
865                 870                 875                 880

Glu Thr Gly Asn Tyr Leu Thr Lys Tyr Ser Lys Lys Asp Asn Gly Pro
            885                 890                 895

Val Ile Lys Lys Ile Lys Tyr Tyr Gly Asn Lys Leu Asn Ala His Leu
            900                 905                 910

Asp Ile Thr Asp Asp Tyr Pro Asn Ser Arg Asn Lys Val Val Lys Leu
        915                 920                 925

Ser Leu Lys Pro Tyr Arg Phe Asp Val Tyr Leu Asp Asn Gly Val Tyr
    930                 935                 940

Lys Phe Val Thr Val Lys Asn Leu Asp Val Ile Lys Lys Glu Asn Tyr
945                 950                 955                 960

Tyr Glu Val Asn Ser Lys Cys Tyr Glu Glu Ala Lys Lys Leu Lys Lys
            965                 970                 975

Ile Ser Asn Gln Ala Glu Phe Ile Ala Ser Phe Tyr Asn Asn Asp Leu
```

```
                980             985             990
Ile Lys Ile Asn Gly Glu Leu Tyr Arg Val Ile Gly Val Asn Asn Asp
            995            1000             1005

Leu Leu Asn Arg Ile Glu Val Asn Met Ile Asp Ile Thr Tyr Arg
       1010             1015            1020

Glu Tyr Leu Glu Asn Met Asn Asp Lys Arg Pro Pro Arg Ile Ile
    1025            1030            1035

Lys Thr Ile Ala Ser Lys Thr Gln Ser Ile Lys Lys Tyr Ser Thr
    1040            1045            1050

Asp Ile Leu Gly Asn Leu Tyr Glu Val Lys Ser Lys Lys His Pro
    1055            1060            1065

Gln Ile Ile Lys Lys Gly
    1070

<210> SEQ ID NO 58
<211> LENGTH: 4289
<212> TYPE: DNA
<213> ORGANISM: Artificial Sequence
<220> FEATURE:
<223> OTHER INFORMATION: Synthetic: AAV construct insert (2 sgRNAs;
      synthetic)

<400> SEQUENCE: 58
ggttccatgg tgtaatggtt agcactctgg actctgaatc cagcgatccg agttcaaatc      60
tcggtggaac ctggagacgg acgtctccgt tttagtactc tggaaacaga atctactaaa    120
acaaggcaaa atgccgtgtt tatctcgtca acttgttggc gagattttt tctagagagg    180 gcctatttcc catgattcct tcatatttgc atatacgata caaggctgtt agagagataa    240
ttggaattaa tttgactgta aacacaaaga tattagtaca aaatacgtga cgtagaaagt    300
aataatttct tgggtagttt gcagttttaa aattatgttt taaaatggac tatcatatgc    360
ttaccgtaac ttgaaagtat ttcgatttct tggctttata tatcttgtgg aaaggacgaa    420
acaccgggtc ttcgagaaga cccgttttag tactctggaa acagaatcta ctaaaacaag    480
gcaaaatgcc gtgtttatct cgtcaacttg ttggcgagat tttttctcga ggtcggagga    540
tccacaaagg ctagccggtc tatgcattag gtcttgaaag gagtgggaat tggctccggt    600
gcccgtcagt gggcagagcg cacatcgccc acagtccccg agaagttggg gggaggggtc    660
ggcaattgat ccggtgccta gagaaggtgg cgcggggtaa actgggaaag tgatgtcgtg    720
tactggctcc gcctttttcc cgagggtggg ggagaaccgt atataagtgc agtagtcgcc    780
gtgaacgttc ttttttcgcaa cgggtttgcc gccagaacac aggaagcttg gtaagtgacc    840
agctacagtc ggaaaccatc agcaagcagg tatgtactct ccagggtggg cctggcttcc    900
ccagtcaaga ctccagggat tgagggacg ctgtgggctc ttctcttaca tgtacctttt    960
gctagcctca accctgacta tcttccaggt cattgttcca acgccaccat ggcacttgaa   1020
gctcccaaga gaagcggaa agtgggaagc gattacaagg atgacgatga caagaagagg   1080
aattacatcc tcggactgga catcggcatt accagcgtcg gctacggcat catcgattac   1140
gagacaaggg acgtgattga cgctggcgtc aggctgttca aggaggccaa cgtggagaat   1200
aatgagggca ggagaagcaa gagggcgcc aggaggctga agaggaggag aaggcacaga   1260
atccagaggg tcaagaagct cctgttcgac tacaacctgc tgaccgacca tagcgagctg   1320
agcggcatta ccccctacga ggctagggtc aaaggcctct cccagaaact gtccgaggag   1380
gagtttagcg ctgctctcct gcacctggcc aagaggaggg gagtgcacaa tgtgaacgag   1440
```

```
gtcgaagagg acaccggcaa tgagctcagc accaaggagc agattagcag aaacagcaaa    1500
gccctggagg aaaaatatgt cgccgagcta cagctggaga gactcaagaa ggatggcgag    1560
gtcagaggct ccattaacag gttcaagacc tccgactacg tgaaagaagc caagcagctg    1620
ctgaaggtgc aaaaggccta tcatcagctg gaccagagct tcattgatac ctatatcgac    1680
ctgctcgaaa ccaggagaac ctactatgag ggccctggag aaggaagccc cttcggatgg    1740
aaagacatta aggagtggta cgaaatgctg atgggacact gcacctactt ccccgaggag    1800
ctgaggagcg tgaaatatgc ctacaacgcc gatctctaca cgccctgaa cgacctgaac     1860 aatctcgtga ttacaaggga tgagaacgaa aagctggaat attacgaaaa atttcagatc    1920
attgaaaacg tgtttaagca aaagaagaag cccaccctga gcagattgc caaggagatc     1980 ctggtgaacg aagaggacat taaaggctac agagtgacct ccacaggcaa acccgaattt    2040
accaatctga aggtgtatca cgatatcaaa gatatcacag ctagaaagga gatcatcgag    2100
aatgctgagc tgctcgacca aatcgccaag attctcacca tctaccagag cagcgaggac    2160
atccaggaag aactgacaaa cctgaactcc gagctcaccc aggaagaaat cgagcagatt    2220
tccaacctga aaggctacac cggcacccac aacctgtccc tgaaggccat caacctgatc    2280
ctcgatgaac tctggcacac caatgacaat caaatcgcta tcttcaacag actgaagctc    2340
gtgcccaaga agtggaccct gagccagcag aaggaaatcc ctacaaccct cgtggacgat    2400
ttcatcctca gccccgtcgt gaagaggagc ttcatccagt ccatcaaggt gattaacgct    2460
atcatcaaga gtatggcct ccccaacgac atcatcatcg agctcgctag ggaaaaaaac     2520
tccaaggatg ctcagaaaat gatcaacgag atgcagaaaa ggaacagaca aaccaacgaa    2580
aggattgagg agattatcag gaccaccggc aaggagaatg ctaagtatct gattgaaaaa    2640
attaaactcc acgatatgca ggagggcaag tgtctctata gcctggaagc catccctctg    2700
gaggatctcc tgaacaatcc tttttaactac gaagtggacc acattatccc caggagcgtg    2760
tccttcgata actcctttaa taataaggtc ctggtcaaac aggaggagaa ctccaagaag    2820
ggaaacagga caccctccca atatctctcc agcagcgact ccaaaataag ctacgaaacc    2880
tttaaaaaac acattctgaa cctggccaag ggcaaaggca ggatcagcaa aaccaaaaag    2940
gaatacctcc tggaggagag agacatcaac aggttctccg tgcagaaaga cttcatcaac    3000
aggaacctgg tggacaccag gtatgccacc aggggcctga tgaacctcct gaggtcctat    3060
tttagagtca ataatctcga cgtgaaagtc aaatccatta atggcggctt taccagcttc    3120
ctgaggagaa aatggaagtt caagaaggag agaaacaaag ctacaaaaca ccacgccgaa    3180
gatgccctca tcattgctaa cgccgacttc atctttaagg agtggaagaa gctcgataag    3240
gccaagaaag tcatggagaa tcaaatgttc gaggagaaac aagccgaatc catgcccgag    3300
attgaaacgg agcaagagta caaggaaata ttcatcaccc ctcaccagat caaacacatc    3360
aaggacttca agactacaa atatagccat agagtcgata agaagcccaa cagggagctg    3420
atcaacgaca cactctattc caccagaaag gatgataagg caacacccct gattgtgaac    3480
aacctgaacg gcctctacga taaggataac gacaagctga gaagctgat taacaagagc    3540 cccgagaaac tgctcatgta ccaccacgac ccccaaacat accagaaaact gaagctgatc    3600 atggaacagt atggcgacga gaaaaacccc ctgtataagt actatgaaga aaccggcaac    3660
tacctcacca gtacagcaa aaaggataac ggacccgtga tcaaaagat taagtattac    3720 ggcaataagc tgaatgccca cctcgatatc accgatgatt accccaactc cagaaataaa    3780
gtcgtgaaac tgtccctgaa accttacagg tttgacgtgt acctggacaa tggcgtgtac    3840
```

```
aagttcgtga ccgtgaagaa cctcgacgtg attaagaagg agaattacta tgaggtcaac    3900
agcaaatgct atgaggaagc caagaaactg aagaagattt ccaatcaggc cgagttcatc    3960
gccagctttt ataacaacga cctgattaag atcaatggcg aactgtatag ggtgatcggc    4020
gtcaacaacg acctcctgaa caggattgag gtcaatatga tcgatattac ctacagagag    4080
tacctcgaaa acatgaatga caagaggccc cccaggatta tcaaaaccat cgccagcaag    4140
acccagagca ttaagaaata cagcaccgac atcctcggca acctgtacga ggtcaagtcc    4200
aaaaagcacc cccagattat caaaaaggga tgagtcgaca ataaatatc tttattttca    4260 ttacatctgt gtgttggttt tttgtgtgt                                      4289
```

<210> SEQ ID NO 59
<211> LENGTH: 10
<212> TYPE: PRT
<213> ORGANISM: Artificial Sequence
<220> FEATURE:
<223> OTHER INFORMATION: Synthetic: Nuclear localization signal

<400> SEQUENCE: 59

Leu Glu Ala Pro Lys Lys Lys Arg Lys Val
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic: Nuclear localization signal

<400> SEQUENCE: 60

Ala Ala Pro Ala Ala Lys Lys Lys Leu Asp
1               5                   10

<210> SEQ ID NO 61
<211> LENGTH: 16
<212> TYPE: PRT
<213> ORGANISM: Artificial Sequence
<220> FEATURE:
<223> OTHER INFORMATION: Synthetic: Nuclear localization signal

<400> SEQUENCE: 61

Lys Arg Pro Ala Ala Thr Lys Lys Ala Gly Gln Ala Lys Lys Lys Lys
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: Synthetic: Nuclear localization signal

<400> SEQUENCE: 62

Pro Lys Lys Lys Arg Lys Val
1               5

<210> SEQ ID NO 63
<211> LENGTH: 24
<212> TYPE: DNA
<213> ORGANISM: Artificial Sequence
<220> FEATURE:
<223> OTHER INFORMATION: Synthetic: ICP4 (Nme)

<400> SEQUENCE: 63

```
<210> SEQ ID NO 64
<211> LENGTH: 24
<212> TYPE: DNA
<213> ORGANISM: Artificial Sequence
<220> FEATURE:
<223> OTHER INFORMATION: Synthetic: GFP (Nme)

<400> SEQUENCE: 64
gtcacgaggg tgggccaggg cacg                                          24

<210> SEQ ID NO 65
<211> LENGTH: 25
<212> TYPE: DNA
<213> ORGANISM: Artificial Sequence
<220> FEATURE:
<223> OTHER INFORMATION: Synthetic: G6P (Nme)

<400> SEQUENCE: 65
gatctggttc catcttaaag agact                                         25

<210> SEQ ID NO 66
<211> LENGTH: 23
<212> TYPE: DNA
<213> ORGANISM: Human papilloma virus
<220> FEATURE:
<221> NAME/KEY: misc_feature
<222> LOCATION: (1)..(23)
<223> OTHER INFORMATION: Wild-type E6 partial sequence

<400> SEQUENCE: 66
cgcgctttga ggatccaaca cgg                                           23

<210> SEQ ID NO 67
<211> LENGTH: 23
<212> TYPE: DNA
<213> ORGANISM: Artificial Sequence
<220> FEATURE:
<223> OTHER INFORMATION: Synthetic: Mutant E6 partial sequence

<400> SEQUENCE: 67
cgcgctttga ggaccccacg cgg                                           23

<210> SEQ ID NO 68
<211> LENGTH: 20
<212> TYPE: DNA
<213> ORGANISM: Artificial Sequence
<220> FEATURE:
<223> OTHER INFORMATION: Synthetic: oligonucleotide

<400> SEQUENCE: 68
gaaatcctgc agaaagacct                                               20
```